(12) United States Patent
Westwell et al.

(10) Patent No.: US 11,180,466 B2
(45) Date of Patent: *Nov. 23, 2021

(54) 2-BENZOYLAMINOBENZAMIDE DERIVATIVES AS BCL-3 INHIBITORS

(71) Applicant: University College Cardiff Consultants Limited, Cardiff (GB)

(72) Inventors: Andrew David Westwell, Cardiff (GB); Andrea Brancale, Cardiff (GB); Richard William Ernest Clarkson, Dinas Powys (GB); Jitka Soukupova, Novy Bor (CZ)

(73) Assignee: UNIVERSITY COLLEGE CARDIFF CONSULTANTS LIMITED, Cardiff (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/593,147

(22) Filed: Oct. 4, 2019

(65) Prior Publication Data

US 2020/0031787 A1  Jan. 30, 2020

Related U.S. Application Data

(63) Continuation of application No. 14/908,035, filed as application No. PCT/EP2014/066564 on Jul. 31, 2014, now Pat. No. 10,450,285.

(30) Foreign Application Priority Data

Jul. 31, 2013  (GB) ...................................... 1313664

(51) Int. Cl.
| | | |
|---|---|---|
| *C07D 295/13* | (2006.01) | |
| *A61K 31/495* | (2006.01) | |
| *A61K 31/5375* | (2006.01) | |
| *A61K 31/40* | (2006.01) | |
| *A61K 31/4453* | (2006.01) | |
| *A61K 31/4402* | (2006.01) | |
| *A61K 31/167* | (2006.01) | |
| *C07D 213/40* | (2006.01) | |
| *C07C 237/42* | (2006.01) | |

(52) U.S. Cl.
CPC .......... *C07D 295/13* (2013.01); *A61K 31/167* (2013.01); *A61K 31/40* (2013.01); *A61K 31/4402* (2013.01); *A61K 31/4453* (2013.01); *A61K 31/495* (2013.01); *A61K 31/5375* (2013.01); *C07C 237/42* (2013.01); *C07D 213/40* (2013.01)

(58) Field of Classification Search
CPC .... C07D 295/13; C07D 213/40; C07C 237/42
See application file for complete search history.

(56) References Cited

U.S. PATENT DOCUMENTS

| | | | |
|---|---|---|---|
| 6,218,393 B1 * | 4/2001 | Ryder | C07D 401/12 514/249 |
| 2004/0006011 A1 * | 1/2004 | Gour | C07K 7/06 702/27 |

OTHER PUBLICATIONS

Joensuu et al. in Annals of Oncology 23 (supplement 6):vi40-vi45 (2012) (Year: 2012).*
Moldonado et al. Molecular Cancer 2011; 10:152 (Year: 2011).*
Guan et al. International Journal of Cancer 2011, 128(10):2274-2283 (Year: 2011).*
Brenne et al. European Journal of Haematology 2009, 82(5):354-363 (Year: 2009).*
Puvvada et al. Oncology 2010, 78(3-4):181-188 (Year: 2010).*
Pratt et al. Molecular and Cellular Biology, 2003 23(19):6887-6900 (Year: 2003).*
Soukupova et al. Mol Cancer Ther 2021;20:775-86 (Year: 2021).*

* cited by examiner

*Primary Examiner* — Dennis Heyer
(74) *Attorney, Agent, or Firm* — Stites & Harbison, PLLC; Patrick M. Torre

(57) ABSTRACT

The invention relates to a compound of general formula (I):

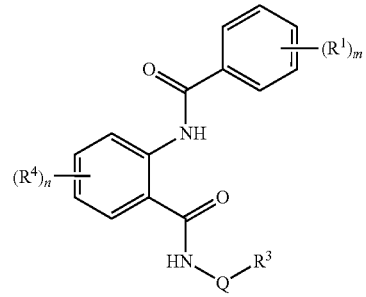

wherein $R^1$, $R^2$, $R^3$, $R^4$, Q, m and n are as defined herein. The compounds are inhibitors of Bcl-3 and are useful for the treatment of cancer, particularly metastatic cancer.

23 Claims, 11 Drawing Sheets

2-BENZOYLAMINOBENZAMIDE DERIVATIVES AS BCL-3 INHIBITORS

This application is a continuation of U.S. application Ser. No. 14/908,035 filed on Jan. 27, 2016, which is the national stage of international patent application no. PCT/EP2014/066564 filed on Jul. 31, 2014 which in turn claims priority from British Patent Application No. 1313664.3 filed on Jul. 31, 2013, the disclosures of all of which are incorporated herein by reference in their entirety.

TECHNICAL FIELD

The invention relates to novel inhibitors of B-cell Lymphoma 3 (Bcl-3); novel therapeutics or compositions comprising said inhibitors of B-cell Lymphoma 3 (Bcl-3); and the use of said therapeutics or compositions to treat cancer and particularly metastatic cancer or secondary cancers.

BACKGROUND

Cancer is a broad group of multiple diseases, all involving unregulated cell growth. In cancer, cells divide and grow uncontrollably, forming malignant tumours. In 2008 approximately 12.7 million cancers were diagnosed and 7.6 million people died of cancer worldwide. Cancers as a group account for approximately 13% of all deaths each year with the most common being: lung cancer (1.4 million deaths), stomach cancer (740,000 deaths), liver cancer (700,000 deaths), colorectal cancer (610,000 deaths), and breast cancer (460,000 deaths). This makes invasive cancer the leading cause of death in the developed world and the second leading cause of death in the developing world.

There are more than 100 different types of cancer, the name for each is derived from the tissue or organ from which it originates. Determining the causes of different cancer types is a complex process as it is generally acknowledged that cancer formation is a multi-faceted process. Cancers are primarily an environmental disease with 90-95% of cases attributed to environmental factors and 5-10% due to genetics. The chances of surviving the disease vary greatly according to the type and location of the cancer, and the extent of disease at the commencement of treatment.

Metastasis, or metastatic disease, is the spread of a cancer from an originating tissue or organ to another tissue or organ. The cells which constitute the primary cancerous tumour commonly undergo metaplasia, followed by dysplasia and then anaplasia, resulting in a malignant phenotype. This malignant phenotype allows for intravasation into the circulation, followed by extravasation to a second site for tumourigenesis. After the tumour cells have migrated to another site, they re-penetrate the vessel or walls and continue to multiply, eventually forming another clinically detectable tumour (secondary tumours). Whilst treatment regimens and therapies for primary tumours are much better understood, with improved efficacy and success rates, and whilst some types of metastatic cancer can be cured with such current treatments, most metastatic cancers show poor response. Treatments for metastatic disease do exist, such as systemic therapy (chemotherapy, biological therapy, targeted therapy, hormonal therapy), local therapy (surgery, radiation therapy), or a combination of these treatments. However, most often the primary goal of these treatments is to control the growth of the cancer or to relieve symptoms caused by same. It is therefore generally considered that most people who die of cancer die of metastatic disease.

For example, breast cancer is the most common cancer in the UK and the most prevalent cancer in women worldwide (there were 1.38 million new cases diagnosed worldwide in 2008 accounting for 23% of all new cancer cases). The relative survival of breast cancer patients has increased dramatically over the last 35 years, with localised disease largely considered to be curable, however, up to 20% of patients are likely to develop metastatic disease which has poor prognosis. Breast cancer tumours show distinct and reproducible subtypes of breast carcinoma associated with different clinical outcomes. ERBB (Her2)-positive breast cancers, which constitute around one third of all breast tumours, have a particularly poor prognosis, exhibiting resistance to first line anti-cancer drugs, and frequently developing metastatic disease—the most common cause of patient death. This particular clinical subtype is therefore an aggressive form of breast cancer with increased incidence of metastasis and consequently poor prognosis.

Therefore improved understanding of cancer progression towards aggressive metastatic forms and tumour cell-specific molecular pathways is necessary to improve and lead to new therapies. However, there are various difficulties associated with targeting metastases and discovering novel molecular targets. The differences between the early stages and metastases development require novel targeted therapy that will differ from targeted therapy for primary tumours. Moreover, the target gene has to be detectable in the disseminated tumour cells or in the primary tumour before metastases. Due to the potential latency period between primary tumour development and metastatic disease, targeted therapy requires administration for prolonged periods with fewer side effects than conventional cancer therapies.

NF-κB (nuclear factor kappa-light-chain-enhancer of activated B cells) is a protein complex that controls the transcription of DNA, and is involved in cellular responses to stimuli such as stress, cytokines, free radicals, ultraviolet irradiation, oxidized LDL, and bacterial or viral antigens. Members of the NF-κB family can both induce and repress gene expression through binding to DNA sequences, and regulate numerous genes that control programmed cell death, cell adhesion, proliferation, immunity and inflammation.

A connection between inflammation and carcinogenesis has been known for a long time, and it is therefore known that NF-κB provides a link between inflammation and cancer progression. Further, NF-κB is widely used by eukaryotic cells as a regulator of genes that control cell proliferation and cell survival. As such, many different types of human tumours have deregulated NF-κB: that is, NF-κB is constitutively active. Deregulated NF-κB has been documented in many cancers, including solid cancers such as breast, melanoma, lung, colon, pancreatic, oesophageal, and also haematological malignancies. For example, it has been shown that increased NF-κB activation was evident in 86% of HER2+/ER− breast cancers and in 33% of basal like cancers, which are associated with a shortened disease-free interval, poor survival and resistance to cancer therapy (1). Moreover, NF-κB activation in tumour cells, tumour-associated stromal and endothelial cells is thought to play a role in tumour progression and invasion (2).

In tumour cells, NF-κB is active either due to mutations in genes encoding the NF-κB transcription factors themselves or in genes that control NF-κB activity (such as IκB genes); in addition, some tumour cells secrete factors that cause NF-κB to become active. Blocking NF-κB can cause tumour cells to stop proliferating, to die, or to become more sensitive to the action of anti-tumour agents. Thus, NF-κB is the subject of much active research among pharmaceutical companies as a target for anti-cancer therapy, and numerous inhibitors of NF-κB and inducers of NF-κB are available.

B-cell Lymphoma 3 (Bcl-3) is a proto-oncogene modulating NF-κB signalling, which was first identified as a chromosome translocation in B-cell chronic lymphocytic leukaemia. Deregulated Bcl-3 over-expression has been reported in numerous tumours including several leukaemias and lymphomas, such as anaplastic large cell lymphomas (ALCLs), classic Hodgkin lymphomas (cHL) and non-Hodgkin's lymphoma (3&4). Additionally, deregulated expression has also been observed in solid tumour cancers, such as breast cancer, nasopharyngeal carcinoma, and hepatocarcinomas (5-7).

A role for NF-κB and Bcl-3 in metastatic colorectal cancer has also been shown, where it was observed that NF-κB activation occurs prior to metastatic spread (8). Notably, Bcl-3 expression was also observed in normal and tumour tissue, but a correlation between nuclear Bcl-3 and patient survival was observed. Bcl-3 expression has also been found to be increased in breast cancer cell lines and patient breast cancer samples versus non-tumorigenic cell lines and normal adjacent tissue, respectively (9). Cells overexpressing Bcl-3 also resulted in a significantly higher number of tumours which supports the role for Bcl-3 in breast cancer progression (10).

The underlying oncogenic function of Bcl-3 has never been fully elucidated. However, established thinking based on experiments performed on cancer cell lines in vitro is that it has a role in increased cellular proliferation and cell survival.

In contrast, we have previously shown that Bcl-3 specifically promotes the formation of metastasis of ErbB2 breast cancer driven tumours (11). Although primary tumour growth in the Bcl-3 deficient ErbB2 (MMTV/neu) murine model was not affected, it was shown that the occurrence of developed lung metastasis from a primary breast tumour was significantly reduced by 40%. Moreover, a significant reduction in mitotic index and apoptosis was observed in secondary tumour lesions but not in primary tumours. Furthermore, through gene expression knock down studies, it was shown that deletion of Bcl-3 resulted in an 80% decrease in lung metastases, which was attributed to loss of cell migration but importantly with no effect upon normal mammary function or overall systemic viability. The implication from these observations, and supported by leading thinkers in the field, is that specific targeting of individual NF-κB subunits or their co-activators may be a more beneficial therapeutic strategy than suppressing their upstream regulators which appear to exhibit detrimental systemic toxicity. This therefore suggests Bcl-3 may represent a suitable therapeutic target for preventing cancer metastasis and secondary tumour formation.

Bcl-3 modulates transcription through binding to the proteins p50 and p52 from the NF-κB family. We have found that Bcl-3 function can be inhibited by disruption of this binding and that Bcl-3 suppression results in a decrease in NF-κB activation, cell migration and proliferative capacity. Using molecular modelling of the Bcl3 protein bound to its cognate NF-κB protein partners, we have identified a novel pharmacophore on the Bcl3 protein, which influences its interaction with the NF-κB proteins.

We have identified compounds which are capable of suppressing Bcl3– NF-κB protein interactions, inhibiting NF-κB signalling and attenuating the cellular characteristics contributing to the metastatic phenotype observed in vivo.

These compounds are therefore useful for the treatment or prevention of cancer, especially metastatic disease and secondary tumour formation.

SUMMARY

According to a first aspect of the invention there is provided a compound of general formula (I):

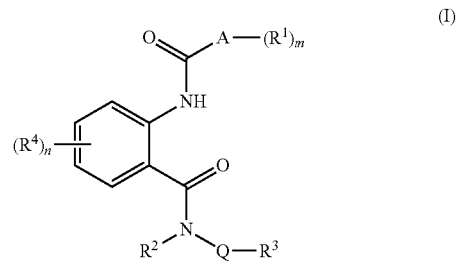

or a salt thereof, wherein:

A is phenyl or pyridyl;

each $R^1$ is independently hydrogen, halo, nitro, cyano, $C_{1-6}$ alkyl, $C_{2-6}$ alkenyl, $C_{1-6}$ haloalkyl, $OR^5$ or $N(R^5R^6)$;

each of $R^5$ and $R^6$ is independently hydrogen, $C_{1-6}$ alkyl or $C_{1-6}$ haloalkyl or, where two $OR^5$ substituents are attached to adjacent carbon atoms they may combine with the carbon atoms to which they are attached to form a 5- or 6-membered ring;

m is 1-5;

$R^2$ is hydrogen or $C_{1-6}$ alkyl;

Q is a bivalent linker comprising a $C_{1-6}$ alkylene group in which one or two —$CH_2$-moieties are optionally replaced by —O— or in which two hydrogen atoms are optionally replaced with a group $(CH_2)_p$, wherein p is 2-4, such that a cyclic group is formed, wherein the bivalent linker may optionally be substituted with one or more substituents selected from halo and OH;

$R^3$ is phenyl or a 5- or 6-membered heteroaryl group either of which may optionally be substituted with one or more substituents selected from $C_{1-4}$ alkyl, $C_{1-4}$ haloalkyl, or OH; or $R^3$ is $NR^7R^8$;

wherein each of $R^7$ and $R^8$ is independently hydrogen or $C_{1-6}$ alkyl or $R^7$ and $R^8$ together with the nitrogen atom to which they are attached may form a 5 to 7 membered heterocyclic ring optionally containing one or more other heteroatoms selected from N, O and S;

each $R^4$ is independently hydrogen, halo, nitro, cyano, $C_{1-6}$ alkyl, $C_{2-6}$ alkenyl, $C_{1-6}$ haloalkyl, $OR^9$ or $N(R^9R^{10})$; and each of $R^9$ and $R^{10}$ is independently hydrogen, $C_{1-6}$ alkyl or $C_{1-6}$ haloalkyl or, where two $OR^9$ substituents are attached to adjacent carbon atoms they may combine with the carbon atoms to which they are attached to form a 5- or 6-membered heterocyclic ring;

n is 1-4, provided that the compound is not 2-[(2-fluorobenzoyl)amino-N-2-morpholin-4-ylethyl)benzamide.

In a further aspect of the invention there is provided a compound of general formula (I) include compounds of general formula (Ia):

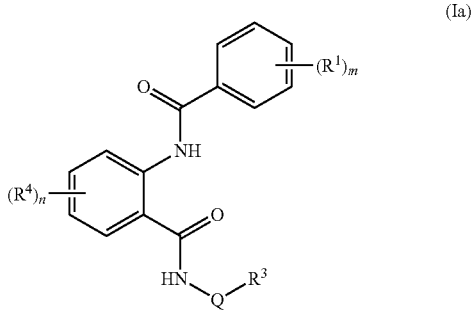

(Ia)

or a salt thereof, wherein:

each $R^1$ is independently halo, nitro, cyano, $C_{1-6}$ alkyl, $C_{2-6}$ alkenyl, $C_{1-6}$ haloalkyl, $OR^5$ or $N(R^5R^6)$;

each of $R^5$ and $R^6$ is independently hydrogen, $C_{1-6}$ alkyl or $C_{1-6}$ haloalkyl;

m is 0, 1 or 2;

Q is $(CH_2)_p$;

p is 1, 2, 3 or 4;

$R^3$ is morpholinyl, piperidinyl, piperazinyl, pyrrolidinyl, pyrazolidinyl, imidazolinyl, to pyridyl, pyrrolyl, pyrimidinyl, imdizolyl, triazolyl or amino;

each $R^4$ is independently nitro, cyano, $C_{1-6}$ alkyl, $C_{2-6}$ alkenyl, $C_{1-6}$ haloalkyl, $OR^9$ or $N(R^9R^{10})$;

each of $R^9$ and $R^{10}$ is independently hydrogen, $C_{1-6}$ alkyl or $C_{1-6}$ haloalkyl; and n is 0, 1 or 2, provided that the compound is not 2-[(2-fluorobenzoyl) amino-N-2-morpholin-4-ylethyl)benzamide.

As discussed above, these compounds are capable of suppressing Bcl3– NF-κB protein interactions, inhibiting NF-κB NF-κB signalling and attenuating the cellular characteristics contributing to the metastatic phenotype observed in vivo and therefore the compounds are suitable for the treatment of cancer, especially for the treatment or prevention of metastatic cancer or secondary tumours.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

In the present specification, references to compounds of general formula (I) or (Ia) includes amorphous and crystalline forms, including all polymorphs, as well as isotopic variants, for example compounds of formula (I) or (Ia) in which one or more hydrogen atoms is replaced by deuterium, one or more carbon atoms is replaced by $^{14}C$ or one or more nitrogen atoms is replaced by $^{15}N$.

In the present specification "$C_{1-6}$ alkyl" refers to a straight or branched saturated hydrocarbon chain having one to six carbon atoms. Examples include methyl, ethyl, n-propyl, isopropyl, t-butyl and n-hexyl.

The term "$C_{1-4}$ alkyl" has a similar meaning to the above except that it refers to a straight or branched saturated hydrocarbon chain having one to four carbon atoms. In the present specification, "halo" refers to fluoro, chloro, bromo or iodo.

The term "haloalkyl" refers to an alkyl group as defined above substituted with one or more halo atoms. The group may have a single halo substituent or it may be a perhalo group. Examples include chloromethyl, trifluoromethyl, 1,2-dichloroethyl, 1,1,1-tribromo-"propyl and perfluoro-"butyl.

The term "$C_{2-6}$ alkenyl" refers to a straight or branched hydrocarbon chain containing at least one carbon-carbon double bond and having two to six carbon atoms. Examples include ethenyl, propen-1-yl and propen-2-yl.

"$C_{1-6}$ alkylene" refers to a straight or branched divalent hydrocarbon linking group having from one to six carbon atoms. Examples include —$CH_2$—, —$CH_2CH_2$—, —$CH_2CH_2CH_2CH_2$, —$CH(CH_3)$— and —$CH(CH_2CH_3)$—.

The terms "heterocyclic" and "heterocyclyl" refer to a non-aromatic cyclic group in which one or more ring atoms is replaced by a hetero atom selected from N, O and S. Examples include aziridine, azetidine, pyrrolidine, pyrroline, imidazoline, piperidine, piperazine, morpholine, oxetane, tetrahydrofuran and oxazoline. Further examples include fused or bridged ring systems such as octahydroquinoline or nortropane.

The terms "heteroaromatic" and "heteroaryl" in the context of the specification refers to a ring system with aromatic character having from 5 to 10 ring atoms (unless otherwise specified), at least one of which is a heteroatom selected from N, O and S, and containing one ring or two fused rings. Where a heteroaryl group contains more than one ring, not all rings must be fully aromatic in character. Examples of monocyclic heteroaryl groups include pyridine, pyrimidine, furan, thiophene, pyrrole, pyrazole, imidazole, oxazole, isoxazole, thiazole and isothiazole. Examples of bicyclic fully aromatic heteroaryl groups include quinoline, isoquinoline, indole, benzofuran, benzimidazole and benzothiazole. Examples of bicyclic heteroaryl groups in which one ring is not fully aromatic in character include dihydroquinolines, tetrahydroquinoline, tetrahydroisoquinoline, chromene, chromane, benzimidazoline, benzomorpholine, isoindoline and indoline.

Salts of the compounds of the present invention include salts of organic acids, especially carboxylic acids, including but not limited to acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, pamoate, pectinate, 3-phenylpropionate, picrate, pivalate, proprionate, tartrate, lactobionate, pivolate, camphorate, undecanoate and succinate, organic sulfonic acids such as methanesulfonate, ethanesulfonate, 2-hydroxyethane sulfonate, camphorsulfonate, 2-naphthalenesulfonate, benzenesulfonate, p-chlorobenzenesulfonate and p-toluenesulfonate; and inorganic acids such as hydrochloride, hydrobromide, hydroiodide, sulfate, bisulfate, hemisulfate, thiocyanate, persulfate, phosphoric and sulfonic acids.

Where appropriate, pharmaceutically or veterinarily acceptable salts of the compounds of general formula (I) or (Ia) may also include basic addition salts salts such as sodium, potassium, calcium, aluminium, zinc, magnesium and other metal salts as well as choline, diethanolamine, ethanolamine, ethyl diamine and other well-known basic addition salts.

Salts will preferably be pharmaceutically or veterinarily acceptable but other salts may still be valuable as intermediates.

In suitable compounds of the present invention, each $R^1$ is independently hydrogen, halo, nitro, $C_{1-4}$ alkyl, $C_{1-4}$ haloalkyl or $OR^5$. $R^5$ is as defined above but is more suitably hydrogen, methyl or ethyl, either of which may optionally be substituted by one or more halo substituents.

In more suitable compounds of general formula (I), each $R^1$ is independently hydrogen, halo, nitro, methyl, trifluoromethyl, OH, methoxy or trifluoromethoxy.

Suitably m is 1, 2 or 3.

In suitable compounds of general formula (I), A is phenyl.

In some suitable compounds of the present invention, $R^2$ is hydrogen, methyl or ethyl. Compounds in which $R^2$ is hydrogen are particularly suitable.

The linker group Q is suitably a straight or branched $C_{1-6}$ alkylene group.

More suitably, Q is a group $(CH_2)_p$, where p is an integer of 1 to 4. In still more suitable compounds, p is 2 or 3.

In some suitable compounds of general formula (I), $R^3$ is phenyl or a 5- or 6-membered heteroaryl group either of which may optionally be substituted with one or more substituents selected from $C_{1-4}$ alkyl, $C_{1-4}$ haloalkyl, or OH.

More suitably, in this embodiment, $R^3$ is phenyl or a 5- or 6-membered nitrogen containing heteroaryl group such as pyridyl, pyrrolyl, pyrimidinyl, imdizolyl or triazolyl, any of which may optionally be substituted as set out above.

Still more suitably, $R^3$ is phenyl or pyridyl, especially pyridyl.

In other suitable compounds, $R^3$ is $NR^7R^8$, wherein each of $R^7$ and $R^8$ is independently hydrogen or $C_{1-6}$ alkyl or $R^7$ and $R^8$ together with the nitrogen atom to which they are attached may form a 5 to 7 membered heterocyclic ring optionally containing one or more other heteroatoms selected from N, O and S.

In more suitable compounds of this embodiment $R^7$ and $R^8$ together with the nitrogen atom to which they are attached may form a 5 to 7 membered heterocyclic ring optionally containing one or more other heteroatoms selected from N, O and S.

In particularly suitable compounds, $R^3$ is a group $NR^7R^8$, which is a 5- or 6-membered nitrogen containing heterocyclic ring. Examples of particularly suitable $R^3$ groups of this type include morpholine, piperidine, piperazine, pyrrolidine, pyrazolidine and imidazoline, with morpholine, piperidine, piperazine and pyrrolidine being especially suitable.

In some suitable compounds of general formula (I), each $R^4$ is independently hydrogen, halo, nitro, cyano, $0_{14}$ alkyl, $C_{1-4}$ haloalkyl or $OR^9$; where $R^9$ is hydrogen, $C_{1-4}$ alkyl or $C_{1-4}$ haloalkyl.

Still more suitably, each $R^4$ is independently hydrogen, halo or methyl or ethyl, either of which is optionally substituted by one or more halo substituents.

Suitably, n is 1, 2 or 3.

In suitable compounds of formula (Ia), each $R^1$ is independently halo, nitro, $C_{1-4}$ alkyl, $C_{1-4}$ haloalkyl or $OR^5$. $R^5$ is as defined above in formula (Ia) but is suitably hydrogen, or methyl or ethyl, either of which may optionally be substituted by one or more halo substituents.

In more suitable compounds of general formula (Ia), each $R^1$ is independently halo, nitro, methyl, trifluoromethyl, OH, methoxy or trifluoromethoxy. In still more suitable compounds of general formula (Ia), at least one $R^1$ is fluoro, and more suitably, 2-fluoro. In other more suitable compounds of general formula (Ia), at least one $R^1$ is $OR^5$. Suitably, $R^5$ is $C_{1-6}$ alkyl, and more suitably, methyl.

Suitably, in compounds of general formula (Ia), m is 1 or 2.

In some suitable compounds of general formula (Ia), $R^3$ is morpholinyl, piperidinyl, piperazinyl and pyrrolidinyl, with morpholinyl being especially suitable.

In some suitable compounds of general formula (Ia), p is 2 or 3.

In some suitable compounds of general formula (Ia), each $R^4$ is independently $C_{1-4}$ alkyl or $OR^9$. $R^9$ is as defined above in formula (Ia) but is suitably hydrogen, $C_{1-4}$ alkyl or $C_{1-4}$ haloalkyl. More suitably, each $R^4$ is independently methyl or methoxy.

Suitably, in compounds of general formula (Ia), n is 0 or 1, and more suitably, 0.

Particularly suitable compounds of general formula (I) or (Ia) include:

2-[(3-fluorobenzoyl)amino]-N-(2-morpholin-4-ylethyl)benzamide;

2-[(4-fluorobenzoyl)amino]-N-(2-morpholin-4-ylethyl)benzamide;

2-[(2-methoxybenzoyl)amino]-N-(2-morpholin-4-ylethyl)benzamide;

2-[(3-methoxybenzoyl)amino]-N-(2-morpholin-4-ylethyl)benzamide;

2-[(4-methoxybenzoyl)amino]-N-(2-morpholin-4-ylethyl)benzamide;

2-[(2-nitrobenzoyl)amino]-N-(2-morpholin-4-ylethyl)benzamide;

2-[(3-nitrobenzoyl)amino]-N-(2-morpholin-4-ylethyl)benzamide;

2-[(4-nitrobenzoyl)amino]-N-(2-morpholin-4-ylethyl)benzamide;

2-[(2-methylbenzoyl)amino]-N-(2-morpholin-4-ylethyl)benzamide;

2-benzamido-N-(2-morpholin-4-ylethyl)benzamide;

3,4-dimethoxy-N-(2-[(2-morpholin-4-ylethyl)carbamoyl]phenyl)benzamide;

3,5-dimethoxy-N-(2-[(2-morpholin-4-ylethyl)carbamoyl]phenyl) benzamide;

3,4,5-trimethoxy-N-(2-[(2-morpholin-4-ylethyl)carbamoyl]phenyl) benzamide;

3,5-difluoro-N-(2-[(2-morpholin-4-ylethyl)carbamoyl]phenyl)benzamide;

2,6-difluoro-N-(2-[(2-morpholin-4-ylethyl) carbamoyl]phenyl)benzamide;

2,4-difluoro-N-(2-[(2-morpholin-4-ylethyl)carbamoyl]phenyl)benzamide;

2-[(2-fluorobenzoyl)amino]-N-(2-morpholin-4-ylpropyl)benzamide;

2-[(4-fluorobenzoyl)amino]-N-(pyridin-3-ylmethyl)benzamide;

2-[(4-fluorobenzoyl)amino]-N-(pyrrolidin-3-ylmethyl)benzamide;

2-[(4-fluorobenzoyl)amino]-N-(piperidin-3-ylmethyl)benzamide;

2-[(4-fluorobenzoyl)amino]-N-(piperazin-3-ylmethyl)benzamide;

N-(2-aminoethyl)-2-(2-fluorobenzamido) benzamide;

2-[(2-fluorobenzoyl)amino]-3-methyl-N-(2-morpholin-4-ylethyl)benzamide;

2-[(2-fluorobenzoyl)amino]-3-methoxy-N-(2-morpholin-4-ylethyl)benzamide;

2-[(2-fluorobenzoyl)amino]-5-iodo-N-(2-morpholin-4-ylethyl)benzamide;

2-[(2-fluorobenzoyl)amino]-2-chloro-N-(2-morpholin-4-ylethyl)benzamide;

2-fluoro-N-(2-((2-morpholinoethyl)carbamoyl)phenyl)benzamide;

and their pharmaceutically or veterinarily acceptable salts.

Compounds of general formula (I) may be prepared by any suitable route. For example, compounds of general formula (I) may be prepared from compound of general formula (II):

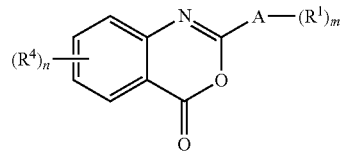
(II)

wherein A, $R^1$, m, $R^4$ and n are as defined for general formula (I);

by reaction with a compound of general formula (III):

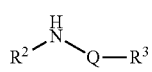
(III)

wherein Q, $R^2$ and $R^3$ are as defined for general formula (I).

Similarly, compounds of general formula (Ia) may be prepared by any suitable route. For example, compounds of general formula (Ia) may be prepared from compound of general formula (IIa):

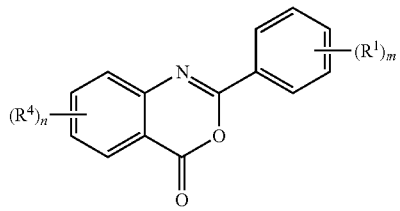
(IIa)

by reaction with a compound of general formula (IIIa):

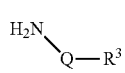
(IIIa)

wherein $R^1$, m, $R^3$, $R^4$ and n are as defined for general formula (Ia).

These processes form a further aspect of the invention.

These reactions are carried out in the presence of a base, typically a non-nucleophlic base, for example a tertiary amine such as N,N-diisopropylethylamine. These reactions may be conducted in an organic solvent such as N,N-dimethylformamide and at a temperature of 15-30° C., more typically at about 18-25° C. (room temperature).

Amines of general formula (III) or (IIIa) are well known and are readily available or may be prepared by literature methods well known to those of skill in the art.

Compounds of general formula (II) may be prepared from compounds of general formula (IV):

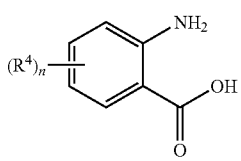
(IV)

wherein $R^4$ and n are as defined for general formula (I);
by reaction with compounds of general formula (V):

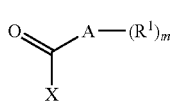
(V)

wherein A, $R^1$ and m are as defined for general formula (I) and X is a leaving group, typically a halo group such as chloro.

Similarly, compounds of general formula (IIa) may be prepared from compounds of general formula (IVa):

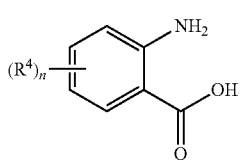
(IVa)

by reaction with compounds of general formula (Va):

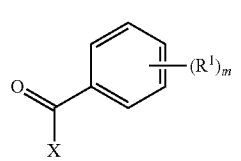
(Va)

wherein $R^1$, m, $R^4$ and n are as defined for general formula (Ia) and X is a leaving group, typically a halo group such as chloro.

These reactions may be carried out in an organic solvent such as pyridine and at a temperature of 15-30° C., more typically at about 18-25° C. (room temperature).

Compounds of general formulae (IV), (IVa), (V) and (Va) are well known and are readily available or may be prepared by literature methods well known to those of skill in the art.

As discussed above, the compounds of the present invention are Bcl3 inhibitors and are therefore of use in the treatment of cancer, for example leukaemias and lymphomas, such as anaplastic large cell lymphomas (ALCLs), classic Hodgkin lymphomas (cHL) and non-Hodgkin's lymphoma; and solid tumour cancers, such as breast cancer, melanoma, lung cancer, pancreatic cancer, oesophageal cancer, colorectal cancer, nasopharyngeal carcinoma, ovarian, prostate and hepatocarcinomas.

Therefore, in a further aspect of the invention there is provided a compound of general formula (I), (Ia) or 2-[(2-fluorobenzoyl)amino-N-2-morpholin-4-ylethyl)benzamide for use in medicine. In particular, there is provided a compound of general formula (I) or (Ia) for use in the treatment of cancer, for example leukaemias and lymphomas, such as anaplastic large cell lymphomas (ALCLs), classic Hodgkin lymphomas (cHL) and non-Hodgkin's lymphoma; and solid tumour cancers, such as breast cancer, melanoma, lung cancer, pancreatic cancer, oesophageal cancer, colorectal cancer, ovarian cancer, prostate cancer, nasopharyngeal carcinoma, and hepatocarcinomas.

In a further aspect of the invention, there is provided the use of a compound of general formula (I), (Ia) or 2-[(2-fluorobenzoyl)amino-N-2-morpholin-4-ylethyl)benzamide in the preparation of an agent for the treatment of cancer, for example leukaemias and lymphomas, such as anaplastic large cell lymphomas (ALCLs), classic Hodgkin lymphomas (cHL) and non-Hodgkin's lymphoma; and solid tumour cancers, such as breast cancer, melanoma, lung cancer, pancreatic cancer, oesophageal cancer, colorectal cancer, ovarian cancer, prostate cancer, nasopharyngeal carcinoma and hepatocarcinomas.

The compounds may be used either in human or in veterinary medicine and the patient may be any mammal but especially a human.

The invention also provides a method for the treatment of cancer, for example leukaemias and lymphomas, such as anaplastic large cell lymphomas (ALCLs), classic Hodgkin lymphomas (cHL) and non-Hodgkin's lymphoma; and solid tumour cancers, such as breast cancer, melanoma, lung cancer, pancreatic cancer, oesophageal cancer, colorectal cancer, ovarian cancer, prostate cancer, nasopharyngeal carcinoma, and hepatocarcinomas, the method comprising administering to a patient in need of such treatment an effective amount of a compound of general formula (I), (Ia) or 2-[(2-fluorobenzoyl)amino-N-2-morpholin-4-ylethyl) benzamide.

The compounds are particularly useful for the treatment or prevention of metastasis in cancers.

Suitably, the cancer is breast cancer, more particularly triple negative breast cancer or HER2 enriched breast cancer. The compounds of formula (I) or (Ia) have been shown to be particularly effective in preventing or treating metastasis in models of these breast cancer subtypes. However this does not preclude its relevance or efficacy in metastatic disease in other tumour types. Moreover, our experimental evidence in human cancer cell lines indicates that there may also be beneficial therapeutic effects of Bcl-3 suppression on tumour cell viability, as both genetic suppression of Bcl-3 and use of compounds of formula (I) or (Ia) partially but significantly reduce tumour cell numbers in vitro.

The compounds of the invention will generally be formulated for administration by a desired route.

Therefore, in a further aspect of the invention there is provided a pharmaceutical composition comprising a compound of general formula (I), (Ia) or 2-[(2-fluorobenzoyl) amino-N-2-morpholin-4-ylethyl)benzamide together with a pharmaceutically or veterinary acceptable excipient or carrier.

The carrier, or, if more than one be present, each of the carriers, must be acceptable in the sense of being compatible with the other ingredients of the formulation and not deleterious to the recipient.

The formulations include those suitable for oral, rectal, nasal, topical (including eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for parenteral administration.

Parenteral formulations will generally be sterile.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I), (Ia) or 2-[(2-fluorobenzoyl)amino-N-2-morpholin-4-ylethyl) benzamide into association with a pharmaceutically or veterinarily acceptable excipient or carrier.

Typically, the dose of the compound will be about 0.01 to 100 mg/kg; so as to maintain the concentration of drug in the plasma at a concentration effective to inhibit Bcl3. The precise amount of a compound of general formula (I), (Ia) or 2-[(2-fluorobenzoyl)amino-N-2-morpholin-4-ylethyl)benzamide which is therapeutically effective, and the route by which such compound is best administered, is readily determined by one of ordinary skill in the art by comparing the blood level of the agent to the concentration required to have a therapeutic effect.

The compound of general formula (I), (Ia) or 2-[(2-fluorobenzoyl)amino-N-2-morpholin-4-ylethyl)benzamide may be used in combination with one or more additional active agents which are useful in the treatment of cancer.

Without limitation, examples of such agents include first-line or adjuvant anti-hormone, radio- or chemo-therapeutics aimed at targeting the primary lesion or suppressing late stage disease progression; for example, anti-HER2 agents such as trastuzumab and pertuzumab and standard adjuvant therapy regimens such as 5-fluorouracil, doxorubicin, and cyclophosphamide (FAC); 5-fluorouracil, epirubicin, and cyclophosphamide (FEC); and doxorubicin and cyclophosphamide (AC); cyclophosphamide, methotrexate, and 5-fluorouracil (CMF); and docetaxel, doxorubicin, cyclophosphamide (TAC). Other suitable agents for use in combination with the compounds of the invention are anti-angiogenic/antimetastatic agents such as bevacizumab (Avastin).

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWINGS

The Invention will now be described by way of example only with reference to the Examples below and to the following Figures wherein.

DETAILED DESCRIPTION

EXAMPLES

Synthesis of Compounds

Figure 1:
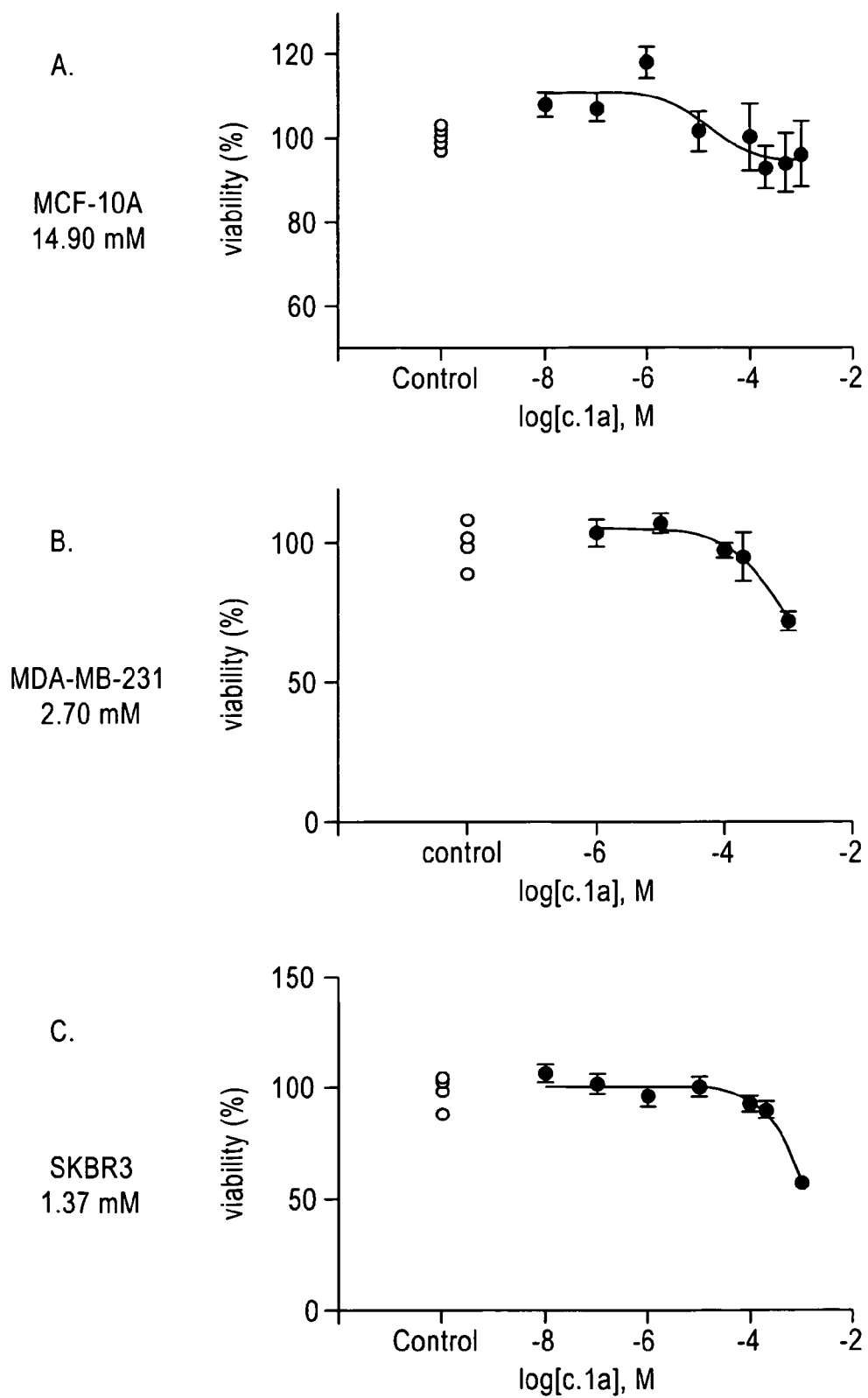
FIG. 1. Cell toxicity of Compound 1a. MCF-10A [A], MDA-MB-231 [B] and SKBR3 [C] breast cancer cells were cultivated with Compound 1a over a range of molarities in adherent growth conditions. Cell viability was determined after 24 hrs by the Cell Titre Blue viability assay and resulting fluorescence was normalised against fluorescence of control cells treated with DMSO in relevant concentration. Data represent average of six wells and error bars represent ±SEM. Dose response curves were generated using GraphPad software. The $IC_{50}$ for each cell line is shown to the left of each graph.

The compounds of the invention were synthesised according to the general method shown in Scheme 1.

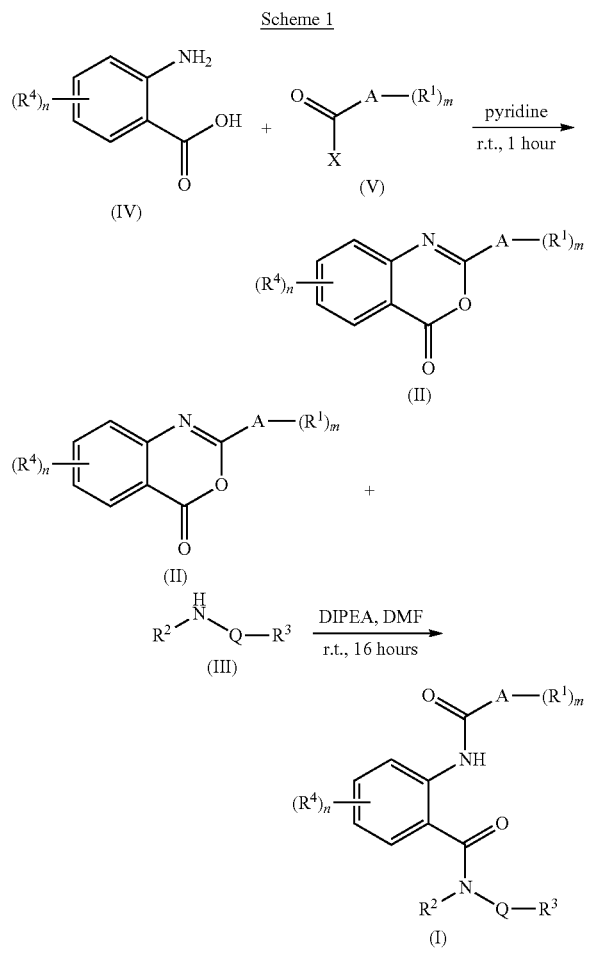

Scheme 1 illustrates the cyclocondensation reaction of the anthranilic acid derivative (IV) and compound (V) which gives rise to the Intermediate (II). In the second step the intermediate (II) was reacted with the amine (III) to give the final product (I).

All chemicals used in this investigation were obtained from commercial suppliers (Sigma Aldrich) and were used without further purification. All glassware were washed and dried before each experiment. Solvents were evaporated using the Buchi Rotavapor. Melting points were measured on a Griffin apparatus using a capillary method.

The $^1$H, $^{13}$C NMR spectra were recorded on a Bruker AVANCE 500 spectrometer at 500 and 126 MHz respectively, at 25° C. Chemical shifts (δ) are reported in parts per million (ppm). J values are reported in Hertz (Hz). Dimethyl sulfoxide (DMSO) was used as a solvent. Used abbreviations include s (singlet), d (doublet), t (triplet), q (quadruplet), m (multiplet), dd (doublet of doublets), dt (doublet of triplets), td (triplet of doublets).

TLC was performed using Merck TLC silica gel 60 plates F254 (40-60 μM) with detection by UV light (254-366 nm).

Mass spectrometry was run using electron ionisation (EI) and electrospray (ES) on a Waters GCT Premier or a Waters LCT Premier XE, respectively. The mass spectrometry was performed as a service by School of Chemistry, Cardiff University. Elemental analysis (CHN) microanalysis was performed as a service by MEDAC Ltd, Surrey. High resolution mass spectrometry was performed on LTQ Orkitrap XL by the EPSRC National Mass Spectrometry Service (Swansea, UK).

General Method for Step 1

In the first step, an anthranilic acid derivative (IV) was dissolved in pyridine (5 ml) and 2.2 equivalent of a substituted benzoyl chloride (V) and stirred at r.t. The reaction was monitored by TLC and stopped after approximately an hour after complete disappearance of the anthranilic acid (V). The reaction mixture was poured into 10% solution of sodium carbonate (3 g sodium carbonate, 27 ml distilled water). The formed precipitate was collected by filtration under reduced pressure as intermediate (II).

General Method for Step 2

In the second step, to a stirred solution of intermediate (II) DMF (10 ml) were added 2 equivalents of DIPEA and 2.2 equivalents of amine (III). The reaction mixture was stirred at r.t overnight. The complete disappearance of starting material (II) was monitored by TLC. The reaction mixture was dissolved in DCM and washed three times with water. The product was evaporated under reduced pressure and the obtained solid was recrystallized from ethanol. All synthesised compounds were analysed by $^1$H, $^{13}$C NMR spectra and mass spectrometry. The purity of final compounds was also confirmed by elemental analysis.

Example 1

Synthesis of Compounds of Series 1

The compounds of series 1 have the general formula

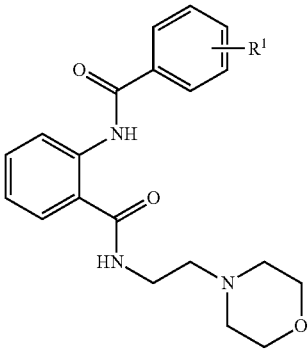

| Compound | R$^1$ |
|---|---|
| 1a | 2-F |
| 1b | 3-F |
| 1c | 4-F |
| 1d | 2-OCH$_3$ |
| 1e | 3-OCH$_3$ |
| 1f | 4-OCH$_3$ |
| 1g | 2-NO$_2$ |
| 1h | 3-NO$_2$ |
| 1i | 4-NO$_2$ |
| 1j | 2-CH$_3$ |
| 1k | H |
| 1l | 3,4-OCH$_3$ |
| 1m | 3,5-OCH$_3$ |
| 1n | 3,4,5-OCH$_3$ |
| 1o | 3,5-F |
| 1p | 2,6-F |
| 1q | 2,4-F |

Step 1—Synthesis of Intermediates

Synthesis of 2-(2-fluorophenyl)-4H-3,1-benzoxazin-4-one (Intermediate 1a)

Chemical Formula: C14H8FNO2, Molecular Weight: 241.22

The synthetic procedure followed the general method above using anthranilic acid (0.50 g, 3.65 mmol) dissolved in pyridine (5 ml) and 2.2 equivalent of 2-fluorobenzoyl chloride (0.96 ml, 8.02 mmol). Collected as a white solid, yield 85% (0.75 g), mp 97° C.

$^1$H NMR (500 MHz, DMSO-d6) δ 8.18 (dd, J=8.0, 1.5 Hz, 1H, ArH), 8.10 (td, J=7.8, 1.8 Hz, 1H, ArH), 7.98 (td, J=9.1, 2.2 Hz, 1H, ArH), 7.74 (d, J=7.9 Hz, 1H, ArH), 7.68 (td, J=7.6, 1.2 Hz, 2H, ArH), 7.47-7.40 (m, 2H, ArH).

$^{13}$C NMR (126 MHz, DMSO-d6) δ 160.48 (d, J$_{C-F}$=258.3 Hz, ArC—F), 158.66 (ArC=O), 154.23 (ArC), 146.03 (ArC), 136.88 (ArCH), 134.52 (d, J$_{C-F}$=8.8 Hz, ArCH), 131.10 (ArCH), 129.02 (ArCH), 127.98 (ArCH), 127.03 (ArCH), 124.83 (d, J$_{C-F}$=3.8 Hz, ArCH), 118.66 (d, J$_{C-F}$=10.1 Hz, ArC), 117.21 (d, J$_{C-F}$=21.4 Hz, ArCH), 116.92 (ArC).

MS (APCI$^+$): 242.05 [M+1].

Synthesis of 2-(3-fluorophenyl-4H-3,1-benzoxazin-4-one (Intermediate 1b)

Chemical Formula: C14H8FNO2, Molecular Weight: 241.22

The synthetic procedure followed the general method above using anthranilic acid (0.50 g, 3.65 mmol) dissolved in pyridine (5 ml) and 2.2 equivalent of 3-fluorobenzoyl chloride (0.98 ml, 8.02 mmol). Collected as a white solid, yield 80% (0.71 g), mp 96° C.

$^1$H NMR (500 MHz, DMSO-d6) δ 8.48 (d, J=8.3 Hz, 1H, ArH), 8.17 (d, J=7.9 Hz, 1H, ArH), 8.06-7.93 (m, 2H, ArH), 7.87 (d, J=10.4 Hz, 1H, ArH), 7.81 (d, J=10.1 Hz, 1H, ArH), 7.77-7.48 (m, 1H, ArH), 7.27 (t, J=7.7 Hz, 1H, ArH).

$^{13}$C NMR (126 MHz, DMSO-d6) δ 162.17 (d, J$_{C-F}$=245.7 Hz, ArC—F), 158.56 (ArC=O), 145.93 (ArC), 139.71 (ArC), 136.89 (ArCH), 134.20 (ArCH), 131.28 (d, J J$_{C-F}$=8.2 Hz, ArCH), 130.64 (ArCH), 128.90 (ArCH), 127.00 (ArCH), 123.69 (d, J$_{C-F}$=2.8 Hz, ArCH), 121.14 (ArC), 119.35 (d, J$_{C-F}$=88.2 Hz, ArCH), 117.37 (d, J$_{C-F}$=85.7 Hz, ArC).

MS (APCI$^+$): 242.06 [M+1]. O N O F

Synthesis of 2-(4-fluorophenyl)-4H-3,1-benzoxazin-4-one (Intermediate 1c)

Chemical Formula: C14H8FNO2 Molecular Weight: 241.22

The synthetic procedure followed the general method above using anthranilic acid (0.50 g, 3.65 mmol) dissolved in pyridine (5 ml) and 2.2 equivalent of 4-fluorobenzoyl chloride (0.95 ml, 8.02 mmol). Collected as a white solid, yield 91% (0.80 g), mp 159° C.

$^1$H NMR (500 MHz, DMSO-d6) δ 8.26 (td, J=14.1, 5.4 Hz, 2H, ArH), 8.16 (dd, J=8.0, 1.5 Hz, 1H, ArH), 7.96 (t, J=15.8 Hz, 1H, ArH), 7.72 (d, J=8.1 Hz, 1H, ArH), 7.63 (td, J=7.6, 1.2 Hz, 1H, ArH), 7.48-7.40 (m, 2H, ArH).

$^{13}$C NMR (126 MHz, DMSO-d6) δ 164.74 (d, J$_{C-F}$=251.4 Hz, ArC—F), 158.72 (ArC=O), 155.58 (ArC), 146.18 (ArC), 136.87 (ArCH), 130.53 (d, J$_{C-F}$=9.4 Hz, ArCH), 128.57 (ArCH), 128.05 (ArCH), 126.83 (d, J$_{C-F}$=3.8 Hz, ArCH), 126.61 (ArC), 116.81 (ArC), 116.17 (d, J$_{C-F}$=22.3 Hz, ArCH).

MS (APCI$^+$): 242.06 [M+1].

Synthesis of 2-(2-methoxyphenyl)-4H-3,1-benzoxazin-4-one (Intermediate 1d)

Chemical Formula: C15H11NO3 Molecular Weight: 253.25

The synthetic procedure followed the general method above using anthranilic acid (0.50 g, 3.65 mmol) dissolved in dry pyridine (5 ml) under anhydrous conditions in nitrogen atmosphere and 2.2 equivalent of 2-methoxybenzoyl chloride (1.19 ml, 8.02 mmol). Collected as a white solid, yield 98% (0.91 g), mp 107° C.

$^1$H NMR (500 MHz, DMSO-d6) δ 8.17 (dd, J=7.9, 1.6 Hz, 1H, ArH), 7.97 (td, 16.0, 1.1 Hz, 1H, ArH), 7.78 (dd, J=7.7, 1.8 Hz, 1H, ArH), 7.71 (d, J=7.9 Hz, 1H, ArH), 7.66 (td, J=7.6, 1.2 Hz, 1H, ArH), 7.60 (td, J=8.8, 1.8 Hz, 1H, ArH), 7.24 (d, J=8.4 Hz, 1H, ArH), 7.12 (t, J=7.5 Hz, 1H, ArH), 3.88 (s, 3H, OCH3).

$^{13}$C NMR (126 MHz, DMSO-d6) δ 159.15 (ArC=O), 157.89 (ArC), 157.16 (ArC), 146.31 (ArC), 136.88 (ArCH), 133.24 (ArCH), 130.97 (ArCH), 128.81 (ArCH), 127.90 (ArCH), 126.89 (ArCH), 120.36 (ArCH), 120.27 (ArC), 116.53 (ArC), 112.56 (ArCH), 55.66 (OCH3).

MS (APCI$^+$): 254.07 [M+1].

Synthesis of 2-(3-methoxyphenyl)-4H-3,1-benzoxazin-4-one (Intermediate 1e)

Chemical Formula: C15H11NO3 Molecular Weight: 253.25

The synthetic procedure followed the general method above using anthranilic acid (0.50 g, 3.65 mmol) dissolved in dry pyridine (5 ml) under anhydrous conditions in nitrogen atmosphere and 2.2 equivalent of 3-methoxybenzoyl chloride (1.13 ml, 8.02 mmol). Collected as a white solid, yield 97% (0.90 g), mp 103° C.

$^1$H NMR (500 MHz, DMSO-d6) δ 8.14 (dd, J=7.9, 1.5 Hz, 1H, ArH), 7.94 (t, J=7.9 Hz, 1H, ArH), 7.76 (d, J=7.7, Hz, 1H, ArH), 7.71 (d, J=8.1 Hz, 1H, ArH), 7.66-7.58 (m, 2H, ArH), 7.50 (t, J=8.0 Hz, 1H, ArH), 7.21 (dd, J=8.4, 2.6 Hz, 1H, ArH), 3.85 (s, 3H, OCH3).

$^{13}$C NMR (126 MHz, DMSO-d6) δ 159.42 (ArC=O), 158.79 (ArC), 156.10 (ArC), 146.09 (ArC), 136.86 (ArCH), 131.27 (ArC), 130.16 (ArCH), 128.64 (ArCH), 128.01 (ArCH), 126.90 (ArCH), 120.15 (ArCH), 118.72 (ArCH), 116.79 (ArC), 112.36 (ArCH), 55.35 (OCH3).

MS (APCI$^+$): 254.07 [M+1].

Synthesis of 2-(4-methoxyphenyl)-4H-3,1-benzoxazin-4-one (Intermediate 1f)

Chemical Formula: Cl 5H11NO3 Molecular Weight: 253.25

The synthetic procedure followed the general method above using anthranilic acid (0.50 g, 3.65 mmol) dissolved in dry pyridine (5 ml) under anhydrous conditions in nitrogen atmosphere and 2.2 equivalent of 4-methoxybenzoyl chloride (1.09 ml, 8.02 mmol). Collected as a white solid, yield 71% (0.66 g), mp 121° C.

$^1$H NMR (500 MHz, DMSO-d6) δ 8.14 (td, J=17.8, 1.8 Hz, 3H, ArH), 7.93 (td, J=8.5, 1.6 Hz, 1H, ArH), 7.68 (d, J=7.9 Hz, 1H, ArH), 7.59 (td, J=7.4, 1.2 Hz, 1H, ArH), 7.14 (d, J=9.0 Hz, 2H, ArH), 3.88 (s, 3H, OCH3).

$^{13}$C NMR (126 MHz, DMSO-d6) δ 162.88 (ArC=O), 158.95 (ArC), 156.39 (ArC), 146.59 (ArC), 136.80 (ArCH), 132.66 (ArCH), 129.80 (ArCH), 126.61 (ArCH), 122.10 (ArCH), 120.18 (ArC), 116.55 (ArC), 114.45 (ArCH), 55.56 (OCH3).

MS (APCI$^+$): 254.08 [M+1].

Synthesis of 2-(2-nitrophenyl)-4H-3,1-benzoxazin-4-one (Intermediate 1g)

Chemical Formula: C14H8N2O4 Molecular Weight: 268.22

The synthetic procedure followed the general method above using anthranilic acid (0.50 g, 3.65 mmol) dissolved in pyridine (5 ml) and 2.2 equivalent of 2-nitrobenzoyl chloride (1.06 ml, 8.02 mmol). Collected as a yellow solid, yield 77% (0.75 g), mp 169° C.

$^1$H NMR (500 MHz, DMSO-d6) δ 8.22 (dd, J=7.8, 1.5 Hz, 1H, ArH), 8.17 (dd, J=8.0, 1.3 Hz, 1H, ArH), 8.10 (dd, J=7.6, 1.5 Hz, 1H, ArH), 8.02 (td, J=7.7, 1.6 Hz, 1H, ArH), 7.96 (td, J=7.6, 1.3 Hz, 1H, ArH), 7.91 (td, J=7.8, 1.6 Hz, 1H, ArH), 7.76-7.69 (m, 2H, ArH).

$^{13}$C NMR (126 MHz, DMSO-d6) δ 158.20 (ArC=O), 154.50 (ArC), 148.15 (ArC), 145.58 (ArC), 137.26 (ArCH), 133.60 (ArCH), 132.97 (ArCH), 131.16 (ArCH), 129.61 (ArCH), 128.22 (ArCH), 127.04 (ArCH), 124.98 (ArC), 124.57 (ArCH), 116.68 (ArC).

MS (APCI$^+$): 269.05 [M+1].

Synthesis of 2-(3-nitrophenyl)-4H-3,1-benzoxazin-4-one (Intermediate 1h)

Chemical Formula: C14H8N2O4 Molecular Weight: 268.22

The synthetic procedure followed the general method above using anthranilic acid (0.50 g, 3.65 mmol) dissolved in pyridine (5 ml) and 2.2 equivalent of 3-nitrobenzoyl chloride (1.06 ml, 8.02 mmol). Collected as a yellow solid, yield 96% (0.94 g), mp 115° C.

$^1$H NMR (500 MHz, DMSO-d6) δ 8.74 (t, J=2.0 Hz, 1H, ArH), 8.48 (dd, J=8.3, 1.1 Hz, 1H, ArH), 8.37 (dd, J=8.5, 1.3 Hz, 2H, ArH), 7.99 (dd, J=7.9, 1.6 Hz, 1H, ArH), 7.91 (t, J=8.0 Hz, 1H, ArH), 7.70 (td, J=8.5, 1.7 Hz, 1H, ArH), 7.30 (td, J=7.6, 1.3 Hz, 1H, ArH).

$^{13}$C NMR (126 MHz, DMSO-d6) δ 167.70 (ArC=O), 162.76 (ArC), 148.00 (ArC), 139.20 (ArC), 135.84 (ArC), 133.98 (ArCH), 133.23 (ArCH), 130.69 (ArCH), 126.53 (ArCH, 124.09 (ArCH), 122.02 (ArCH), 118.95 (ArC).

MS (APCI$^+$): 269.06 [M+1].

Synthesis of 2-(3-nitrophenyl)-4H-3,1-benzoxazin-4-one (Intermediate 1i)

Chemical Formula: C14H8N2O4 Molecular Weight: 268.22

The synthetic procedure followed the general method above using anthranilic acid (0.50 g, 3.65 mmol) dissolved in pyridine (5 ml) and 2.2 equivalent of 4-nitrobenzoyl chloride (1.49 g, 8.02 mmol). Collected as a yellow solid, yield 96% (0.94 g), mp 169° C.

$^1$H NMR (500 MHz, DMSO-d6) δ 8.19 (t, J=7.8 Hz, 2H, ArH), 8.00 (t, J=7.8 Hz, 2H, ArH), 7.79 (d, J=8.1 Hz, 2H, ArH), 7.69 (t, J=7.6 Hz, 2H, ArH).

$^{13}$C NMR (126 MHz, DMSO-d6) δ 158.43 (ArC=O), 154.74 (ArC), 149.62 (ArC), 145.77 (ArC), 136.98 (ArCH), 135.81 (ArC), 129.37 (ArCH), 129.13 (ArCH), 128.13 (ArCH), 127.24 (ArCH), 124.08 (ArCH), 117.20 (ArC).

MS (APCI$^+$): 269.08 [M+1].

Synthesis of 2-(o-tolyl)-4H-3,1-benzoxazin-4-one (Intermediate 1j)

Chemical Formula: C15H11NO2 Molecular Weight: 237.25

The synthetic procedure followed the general method above using anthranilic acid (0.50 g, 3.65 mmol) dissolved in pyridine (5 ml) and 2.2 equivalent of 2-methyl benzoyl chloride (1.05 ml, 8.02 mmol). Collected as a yellow solid, yield 99% (0.86 g), mp 102° C.

$^1$H NMR (500 MHz, DMSO-d6) δ 8.17 (d, J=8.0 Hz, 1H, ArH), 7.99-7.90 (m, 2H, ArH), 7.71 (d, J=8.1 Hz, 1H, ArH), 7.65 (t, J=7.6 Hz, 1H, ArH), 7.51 (t, J=7.5 Hz, 1H, ArH), 7.40 (t, J=6.9 Hz, 2H, ArH), 2.66 (s, 3H, CH3).

$^{13}$C NMR (126 MHz, DMSO-d6) δ 159.07 (ArC=O), 157.59 (ArC), 146.17 (ArC), 138.32 (ArC), 136.74 (ArCH), 131.69 (ArCH), 131.48 (ArCH), 129.88 (ArC), 129.79 (ArCH), 128.69 (ArCH), 127.84 (ArCH), 126.93 (ArCH), 126.07 (ArCH), 116.68 (ArC), 21.31 (CH3).

MS (APCI$^+$): 238.07 [M+1].

Synthesis of 2-phenyl-4H-3,1-benzoxazin-4-one (Intermediate 1k)

Chemical Formula: C14H9NO2 Molecular Weight: 223.23

The synthetic procedure followed the general method above using anthranilic acid (0.50 g, 3.65 mmol) dissolved in pyridine (5 ml) and 2.2 equivalent of benzoyl chloride (0.93 ml, 8.02 mmol). Collected as a yellow solid, yield 95% (0.77 g), mp 91° C.

$^1$H NMR (500 MHz, DMSO-d6) δ 8.22 (dd, J=7.3, 1.7 Hz, 1H, ArH), 8.03 (dd, J=7.9, 1.6 Hz, 1H, ArH), 7.98 (dd, 8.1, 1.6 Hz, 2H, ArH), 7.72-7.64 (m, 2H, ArH), 7.62 (dd, J=8.1, 6.6 Hz, 3H, ArH).

$^{13}$C NMR (126 MHz, DMSO-d6) δ 168.04 (ArC=O), 164.76 (ArC), 140.25 (ArC), 136.87 (ArCH), 134.33 (ArCH), 132.19 (ArCH), 130.69 (ArCH), 129.00 (ArCH), 127.03 (ArCH), 123.34 (ArCH), 120.75 (ArCH), 116.99 (ArC).

MS (APCI$^+$): 224.08 [M+1].

Synthesis of 2-(3,4-dimethoxyphenyl)-4H-3,1-benzoxazin-4-one (Intermediate 1l)

Chemical Formula: C16H13NO4 Molecular Weight: 283.28

The synthetic procedure followed the general method above using anthranilic acid (0.50 g, 3.65 mmol) dissolved in pyridine (5 ml) and 2.2 equivalent of 3,4-dimethoxybenzoyl chloride (1.61 g, 8.02 mmol). Collected as a white solid, yield 83% (0.86 g), mp 166° C.

$^1$H NMR (500 MHz, DMSO-d6) δ 8.15 (dd, J=7.8, 1.6 Hz, 1H, ArH), 7.94 (td, J=8.4, 1.6 Hz, 1H, ArH), 7.83 (dd, J=8.5, 2.1 Hz, 1H, ArH) 7.71 (dd, J=6.8, 1.7 Hz, 2H, ArH), 7.60 (td, J=8.3, 1.1 Hz, 1H, ArH), 7.18 (d, J=8.6 Hz, 1H, ArH), 3.89 (d, J=4.7 Hz, 6H, OCH3).

$^{13}$C NMR (126 MHz, DMSO-d6) δ 159.35 (ArC=O), 158.95 (ArC), 152.82 (ArC), 148.79 (ArC), 146.56 (ArC), 136.84 (ArCH), 128.09 (ArCH), 126.65 (ArCH), 122.07 (ArC), 121.86 (ArCH), 116.65 (ArC), 111.56 (ArCH), 110.19 (ArCH), 55.77 (OCH3), 55.63 (OCH3).

MS (EI$^+$): 283.1.

Synthesis of 2-(3,5-dimethoxyphenyl)-4H-3,1-benzoxazin-4-one (Intermediate 1m)

Chemical Formula: C16H13NO4 Molecular Weight: 283.28

The synthetic procedure followed the general method above using anthranilic acid (0.50 g, 3.65 mmol) dissolved in pyridine (5 ml) and 2.2 equivalent of 3,5-dimethoxybenzoyl chloride (1.61 g, 8.02 mmol). Collected as a white solid, yield 93% (0.97 g), mp 165° C.

$^1$H NMR (500 MHz, DMSO-d6) δ 8.71 (dd, J=7.8, 1.6 Hz, 1H, ArH), 7.97 (t, J=7.6 Hz, 1H, ArH), 7.75 (dd, J=8.0, 2.1 Hz, 1H, ArH), 7.65 (t, J=7.6 Hz, 1H, ArH), 7.31 (d, J=2.5 Hz, 2H, ArH), 6.81 (d, J=2.3 Hz, 1H, ArH), 3.86 (s, 6H, OCH$_3$)

$^{13}$C NMR (126 MHz, DMSO-d6) δ 160.72 (ArC=O), 158.76 (ArC), 152.82 (ArC), 146.11 (ArC), 145.80 (ArC), 136.84 (ArCH), 132.01 (ArC), 131.55 (ArCH), 128.73 (ArCH), 128.08 (ArCH), 126.99 (ArCH), 116.96 (ArC), 105.49 (ArCH), 104.83 (ArCH), 55.59 (OCH$_3$).

MS (EI$^+$): 283.1.

Synthesis of 2-(3,4,5-trimethoxyphenyl)-4H-3,1-benzoxazin-4-one (Intermediate 1n)

Chemical Formula: C17H15NO5 Molecular Weight: 313.30

The synthetic procedure followed the general method above using anthranilic acid (0.50 g, 3.65 mmol) dissolved in pyridine (5 ml) and 2.2 equivalent of 3,4,5-dimethoxybenzoyl chloride (1.85 g, 8.02 mmol). Collected as a white solid, yield 91% (1.04 g), mp 165° C.

$^1$H NMR (500 MHz, DMSO-d6) δ 8.17 (dd, J=9.3, 1.8 Hz, 1H, ArH), 7.98-7.94 (m, 1H, ArH), 7.75 (d, J=2.9 Hz, 1H, ArH), 7.63 (td, J=15.7, 1.2 Hz, 1H, ArH), 7.49 (s, 2H, ArH), 3.92 (s, 6H, OCH3), 3.80 (s, 3H, OCH$_3$).

$^{13}$C NMR (126 MHz, Chloroform) δ 159.61 (ArC=O), 156.82 (ArC), 153.34 (ArC), 147.07 (ArC), 142.21 (ArC), 136.58 (ArCH), 128.64 (ArCH), 128.09 (ArCH), 127.09 (ArCH), 125.23 (ArC), 116.78 (ArC), 105.60 (ArCH), 61.01 (OCH$_3$), 56.42 (OCH$_3$).

MS (EI$^+$): 313.1.

Syntheiss of 2-(3,5-difluorophenyl)-4H-3,1-benzoxazin-4-one (Intermediate 1o)

Chemical Formula: C14H7F2NO2 Molecular Weight: 259.21

The synthetic procedure followed the general method above using anthranilic acid (0.50 g, 3.65 mmol) dissolved in pyridine (5 ml) and 2.2 equivalent of 3,5-difluorobenzoyl chloride (0.95 ml, 8.02 mmol). Collected as a white solid, yield 94% (0.89 g), mp 122° C.

$^1$H NMR (500 MHz, Chloroform) δ 8.28 (dd, J=9.4, 1.6 Hz, 1H, ArH), 7.88 (m, 3H, ArH), 7.74 (dd, 8.1, 0.6 Hz, 1H, ArH), 7.60 (tt, 15.3, 1.4 Hz, 1H, ArH), 7.05 (m, 1H, ArH).

$^{13}$C NMR (126 MHz, Chloroform) δ 164.11 (d, $J_{C-F}$=10.1 Hz, ArC—F), 162.12 (d, $J_{C-F}$=18.1 Hz, ArC—F), 158.78 (ArC=O), 146.35 (ArC), 136.78 (ArCH), 133.75 (ArC), 128.98 (ArCH), 128.78 (ArCH), 127.49 (ArCH), 117.14 (ArC), 111.40 (d, $J_{C-F}$=7.7 Hz, ArCH), 111.23 (d, $J_{C-F}$=7.2 Hz, ArCH), 107.93 (ArCH), 105.93 (ArC).

MS (EI$^+$): 259.1.

Synthesis of 2-(2,6-difluorophenyl)-4H-3,1-benzoxazin-4-one (Intermediate 1p)

Chemical Formula: C14H7F2NO2 Molecular Weight: 259.21

The synthetic procedure followed the general method above using anthranilic acid (0.50 g, 3.65 mmol) dissolved in pyridine (5 ml) and 2.2 equivalent of 2,6-difluorobenzoyl chloride (1.01 ml, 8.02 mmol). Collected as a white solid, yield 97% (0.92 g), mp 119° C.

$^1$H NMR (500 MHz, Chloroform-d) δ 8.31 (dd, J=7.8, 2.0 Hz, 1H, ArH), 7.92-7.88 (m, 1H, ArH), 7.76 (dd, J=8.1, 1.7 Hz, 1H, ArH), 7.64 (td, J=7.3, 1.2 Hz, 1H, ArH), 7.52 (tt, J=8.5, 6.2 Hz, 1H, ArH), 7.08 (tt, J=7.1, 4.5 Hz, 2H, ArH).

$^{13}$C NMR (126 MHz, DMSO-d6) δ 161.85 (d, $J_{C-F}$=6.2 Hz, ArC—F), 159.75 (d, $J_{C-F}$=7.4 Hz, ArC—F), 158.91 (C=O), 150.95 (ArC), 146.19 (ArC), 136.68 (ArCH), 133.55 (ArC), 133.03 (t, $J_{C-F}$=21.1 Hz, ArCH), 129.38 (ArCH), 128.68 (ArCH), 127.49 (ArCH), 117.26 (ArC), 112.25 (d, $J_{C-F}$=4.2 Hz, ArCH), 112.07 (d, $J_{C-F}$=4.4 Hz, ArCH).

MS (EI$^+$): 259.1.

Synthesis of 2-(2,4-difluorophenyl)-4H-3,1-benzoxazin-4-one (Intermediate 1q)

Chemical Formula: C14H7F2NO2 Molecular Weight: 259.21

The synthetic procedure followed the general method above using anthranilic acid (0.50 g, 3.65 mmol) dissolved in pyridine (5 ml) and 2.2 equivalent of 2,4-difluorobenzoyl chloride (0.99 ml, 8.02 mmol). Collected as a white solid, yield 81% (0.76 g), mp 102° C.

$^1$H NMR (500 MHz, Chloroform-d) δ 8.28 (dd, J=7.9, 0.6 Hz, 1H, ArH), 8.20 (td, J=8.6, 6.4 Hz, 1H, ArH), 7.91-7.84 (m, 1H, ArH), 7.73 (dd, J=8.2, 0.6 Hz, 1Hz, ArH), 7.59 (td, J=7.8, 1.2 Hz, 1H, ArH), 7.08 (m, 2H, ArH).

$^{13}$C NMR (126 MHz, DMSO-d6) δ 164.50 (d, $J_{C-F}$=252.9 Hz, ArC—F), 162.20 (d, $J_{C-F}$=289.0 Hz, ArC—F), 158.99 (ArC=O), 146.63 (ArC), 136.68 (ArCH), 132.85 (ArCH), 128.78 (ArCH), 128.62 (ArCH), 127.48 (ArCH), 116.97 (ArC), 113.95 (ArC), 112.00 (d, $J_{C-F}$=21.9 Hz), 107.25 (ArC), 105.63 (ArCH).

MS (EI$^+$): 259.0.

Step 2—Synthesis of Example Compounds

Synthesis of 2-[(2-fluorobenzoyl)amino]-N-(2-morpholin-4-ylethyl)benzamide (Compound 1a)

Chemical Formula: C20H22FN3O3 Molecular Weight: 371.41

The synthetic procedure followed the general method for step 2 above using Intermediate 1a (1.00 g, 4.15 mmol) in DMF (10 ml), 2 equivalents of DIPEA (1.19 ml, 8.29 mmol) and 2.2 equivalents of 2-morpholinoethanamine (1.44 ml, 9.12 mmol). The product was recrystallized from ethanol as a white solid. Yield 47% (0.73 g), mp 131° C.

$^1$H NMR (500 MHz, DMSO-d6) δ 12.00 (s, 1H, NH), 8.72 (s, 1H, NH), 8.57 (d, J=8.3 Hz, 1H, ArH), 7.89 (td, J=7.7, 1.9 Hz, 1H, ArH), 7.76 (dd, J=8.0, 1.5 Hz, 1H, ArH), 7.68-7.64 (m, 1H, ArH), 7.57 (td, J=8.6, 1.5 Hz, 1H, ArH), 7.46-7.35 (m, 2H, ArH), 7.24 (td, J=7.6, 1.2 Hz, 1H, ArH), 3.53 (t, J=4.6 Hz, 4H, CH$_2$), 3.40 (q, J=6.4 Hz, 2H, CH$_2$), 2.51 (t, J=6.7 Hz, 2H, CH$_2$), 2.47 (t, J=4.7 Hz, 4H, CH$_2$).

$^{13}$C NMR (126 MHz, DMSO-d6) δ 168.03 (C=O), 160.86 (d, $J_{C-F}$=146.2 Hz, ArC—F), 158.28 (C=O), 138.32 (ArC), 133.77 (d, $J_{C-F}$=8.8 Hz, ArCH), 131.83 (ArCH), 130.62 is (d, $J_{C-F}$=1.3 Hz, ArCH), 128.02 (ArCH), 125.04 (d, $J_{C-F}$=3.8 Hz, ArCH), 123.30 (ArCH), 122.94 (d, $J_{C-F}$=13.9 Hz, ArC) 121.73 (ArC), 120.96 (ArCH), 116.57 (d, $J_{C-F}$=22.7 Hz, ArCH), 66.15 (CH$_2$), 56.98 (CH$_2$), 53.18 (CH$_2$), 36.43 (CH$_2$).

MS (ES+): 372.19 [M+1].

Synthesis of Hydrochloride Salt of Compound 1a

Compound 1a (0.31 g, 0.81 mmol) was dissolved in 150 ml of methanol. Hydrogen chloride in methanol (1.2 ml, 1.25M) was added and the mixture was stirred at r.t. for an hour. Methanol was evaporated from the mixture, followed by addition and evaporation of hexane. DCM (2 ml) was added to the mixture followed by addition of hexane and the formed white precipitate was filtered under reduced pressure. Yield 79%, (0.26g), mp 145° C.

$^1$H NMR (500 MHz, Chloroform) δ 11.61 (s, 1H, NH), 9.00 (s, 1H, NH), 8.65 (d, J=8.2 Hz, 1H, ArH), 8.00 (td, J=7.6, 2.0 Hz, 2H, ArH), 7.50-7.43 (m, 2H, ArH), 7.25 (t, J=7.5 Hz, 1H, ArH), 7.15 (t, J=5.3 Hz, 1H, ArH), 7.12 (d, J=7.0 Hz, 1H, ArH), 4.06 (t, J=12.2 Hz, 2H, CH$_2$), 3.93-3.78 (m, 4H, CH$_2$) 3.56 (d, J=11.8 Hz, 2H, CH$_2$), 3.20 (s, 2H, CH$_2$), 3.01 (s, 1H, NH$^+$), 2.87 (t, J=8.3, 7.6 Hz, 2H, CH$_2$).

$^{13}$C NMR (126 MHz, DMSO-d6) δ 169.51 (C=O), 162.15 (ArC—F), 162.16 (ArC), 161.23 (ArC), 159.24 (ArC), 139.50 (ArC), 133.25 (d, $J_{C-F}$=8.8 Hz, ArC), 132.85 (ArCH), 131.70 (d, $J_{C-F}$=2.2 Hz, ArCH), 128.40 (ArCH), 124.69 (d, $J_{C-F}$=3.4 Hz, ArCH), 123.73 (ArCH), 122.04 (ArCH), 120.17 (ArC), 116.35 (d, $J_{C-F}$=23.9 Hz, ArCH), 63.53 (CH$_2$), 58.72 (CH$_2$), 53.11 (CH$_2$), 34.00 (CH$_2$).

Calculated analysis for C20H22FN3O3 (371.41): C, 64.68; H, 5.97; N, 11.31. Found C, 64.49; H, 6.08; N, 11.29.

MS (EI$^+$): 372.2

Synthesis of 2-[(4-fluorobenzoyl)amino]-N-(2-morpholin-4-ylethyl)benzamide (Compound 1c)

Chemical Formula: C20H22FN3O3 Molecular Weight: 371.41

The synthetic procedure followed the general method for step 2 above using Intermediate 1c (0.50 g, 2.06 mmol) in DMF (8 ml), 2 equivalents of DIPEA (0.72 ml, 4.12 mmol) and 2.2 equivalents of 2-morpholinoethanamine (0.60 ml, 4.54 mmol). The product was recrystallized from ethanol as a white solid. Yield 8% (0.05 g), mp 129° C.

$^1$H NMR (500 MHz, DMSO-d6) δ 12.52 (s, 1H, NH), 8.80 (s, 1H, NH), 8.61 (d, J=8.3 Hz, 1H, ArH), 8.0 (td, J=14.1, 2.1 Hz, 2H, ArH), 7.83 (dd, J=7.9, 1.5 Hz, 1H, ArH), 7.58 (td, J=8.2, 7.8, 1.5 Hz, 1H, ArH), 7.45 (t, J=17.6 Hz, 2H, ArH), 7.23 (t, J=7.6, 1H, ArH), 3.55 (t, J=4.6 Hz, 4H, CH$_2$), 3.44 (q, J=6.5 Hz, 2H, CH$_2$), 2.51 (q, J=6.3 Hz, 6H, CH$_2$).

$^{13}$C NMR (126 MHz, DMSO-d6) δ 168.50 (C=O), 164.29 (d, $J_{C-F}$=253.3 Hz, ArC—F), 158.31 (C=O), 139.17 (ArC), 132.15 (ArCH), 131.05 (d, $J_{C-F}$=3.8 Hz, ArC), 129.61 (d, $J_{C-F}$=10.1 Hz, ArCH), 128.10 (ArCH), 122.94 (ArCH), 120.58 (ArC), 120.38 (ArCH), 115.98 (d, $J_{C-F}$=20.2 Hz, ArCH), 66.17 (CH$_2$), 56.96 (CH$_2$), 53.20 (CH$_2$), 36.55 (CH$_2$).

MS (ES+): 372.20 [M+1].

Calculated analysis for C20H22FN3O3 (371.41): C, 64.62; H, 6.09; N, 11.32.

Found C, 64.49; H, 6.08; N, 11.29.

Synthesis of 2-[(3-methoxybenzoyl)amino]-N-(2-morpholin-4-ylethyl)benzamide (Compound 1e)

Chemical Formula: C21H25N3O4 Molecular Weight: 383.44

The synthetic procedure followed the general method for step 2 above using Intermediate 1e (0.50 g, 1.97 mmol) in DMF (8 ml), 2 equivalents of DIPEA (0.69 ml, 3.94 mmol) and 2.2 equivalents of 2-morpholinoethanamine (0.57 ml, 4.34 mmol). The product was recrystallized from ethanol as a white solid. Yield 0.33 g (44%), mp 105° C.

$^1$H NMR (500 MHz, DMSO-d6) δ 12.49 (s, 1H, NH), 8.80 (s, 1H, NH), 6 8.63 (d, J=8.5 Hz, 1H, ArH), 7.82 (dd, J=7.9, 1.6 Hz, 1H, ArH), 7.58 (td, J=17.0, 1.2 Hz, 1H, ArH), 7.52 (d, J=6.5, Hz, 2H, ArH), 7.48 (t, J=3.2 Hz, 1H, ArH), 7.25-7.16 (m, 2H, ArH), 3.86 (s, 3H, CH$_3$), 3.54 (t, J=4.7 Hz, 4H, CH$_2$), 3.44 (q, J=6.5 Hz, 2H, CH$_2$), 2.50 (d, J=15.1 Hz, 2H, CH$_2$), 2.42 (t, J=4.7 Hz, 4H, CH$_2$). $^{13}$C NMR (126 MHz, DMSO-d6) 6 168.50 (C=O), 164.09 (C=O), 159.52 (ArC), 139.19 (ArC), 136.01 (ArC), 132.14 (ArCH), 130.13 (ArCH), 128.10 (ArCH), 122.87 (ArCH), 120.55 (ArC), 120.27 (ArCH), 118.80 (ArCH), 117.63 (ArCH), 112.46 (ArCH), 66.17 (CH$_2$), 56.99 (CH$_2$), 55.28 (0 CH$_3$), 53.18 (CH$_2$), 36.53 (CH$_2$).

MS (ES+): 384.19 [M+1].
Calculated analysis for C21H25N3O4 (383.44): C, 65.78; H, 6.57; N, 10.95. Found C, 65.71; H, 6.77; N, 10.98.

Synthesis of 2-[(4-methoxybenzoyl)amino]-N-(2-morpholin-4-ylethyl)benzamide (Compound 1f)

Chemical Formula: C21H25N3O4 Molecular Weight: 383.44

The synthetic procedure followed the general method for step 2 above using Intermediate 1f (0.50 g, 1.97 mmol) in DMF (8 ml), 2 equivalents of DIPEA (0.69 ml, 3.94 mmol) and 2.2 equivalents of 2-morpholinoethanamine (0.57 ml, 4.34 mmol). The product was recrystallized from ethanol as a white solid. Yield 32% (0.24 g), mp 110° C.

$^1$H NMR (500 MHz, DMSO-d6) δ 12.44 (s, 1H, NH), 8.78 (s, 1H, NH), 8.65 (d, J=8.3 Hz, 1H, ArH), 7.92 (d, J=8.9 Hz, 2H, ArH), 7.81 (dd, J=8.0, 1.5 Hz, 1H, ArH), 7.56 (td, J=8.7, 1.5 Hz, 1H, ArH), 7.19 (d, J=15.5, 1.3 Hz, 3H, ArH), 3.86 (s, 3H, OCH$_3$), 3.55 (t, J=4.6 Hz, 4H, CH$_2$), 3.45 (q, J=6.4 Hz, 2H, CH$_2$), 2.51 (m, 3H, CH$_2$), 2.43 (d, J=9.1 Hz, 3H, CH$_2$).
$^{13}$C NMR (126 MHz, DMSO-d6) δ 168.60 (C=O), 163.87 (C=O), 162.20 (ArC), 140.73 (ArC), 132.10 (ArCH), 128.80 (ArCH), 128.06 (ArCH), 126.63 (ArC), 122.50 (ArCH), 120.23 (ArC), 120.18 (ArCH), 114.18 (ArCH), 66.18 (CH$_2$), 56.98 (CH$_2$), 55.45 (OCH$_3$), 53.21 (CH$_2$), 36.54 (CH$_2$).
MS (ES+): 384.19 [M+1].
Calculated analysis for C21H25N3O4 (383.44): C, 65.78; H, 6.57; N, 10.95. Found C, 65.63; H, 6.62; N, 10.95.

Synthesis of 2-[(2-nitrobenzoyl)amino]-N-(2-morpholin-4-ylethyl)benzamide (Compound 1g)

Chemical Formula: C20H22N4O5 Molecular Weight: 398.16

The synthetic procedure followed the general method for step 2 above using Intermediate 1g (0.50 g, 1.87 mmol) in DMF (8 ml), 2 equivalents of DIPEA (0.65 ml, 3.74 mmol) and 2.2 equivalents of 2-morpholinoethanamine (0.54 ml, 4.11 mmol). The product was recrystallized from ethanol as a white solid. Yield 49% (0.37 g), mp 139° C.

$^1$H NMR (500 MHz, DMSO-d6) δ 12.02 (s, 1H, NH), 8.75 (s, 1H, NH), 8.41 (d, J=8.2 Hz, 1H, ArH), 8.13 (d, J=8.3, 1H, ArH), 7.91 (d, J=15.2 Hz, 1H, ArH), 7.82 (m, 3H, ArH), 7.59 (t, J=8.2 Hz, 1H, ArH), 7.27 (td, J=7.6, 1.3 Hz, 1H, ArH), 3.53 (t, J=4.6 Hz, 4H, CH$_2$), 3.37 (q, J=6.5 Hz, 2H, CH$_2$), 2.46 (t, J=6.8 Hz, 2H, CH$_2$), 2.39 (t, J=4.7 Hz, 4H, CH$_2$)
$^{13}$C NMR (126 MHz, DMSO-d6) δ 168.01 (C=O), 163.35 (C=O), 147.02 (ArC), 138.23 (ArC), 134.11 (ArCH), 132.02 (ArC), 131.58 (ArCH), 131.68 (ArCH), 128.38 (ArCH), 128.11 (ArCH), 124.57 (ArCH), 123.67 (ArCH), 121.76 (ArC), 120.89 (ArCH), 66.14 (CH$_2$), 56.95 (CH$_2$), 53.19 (CH$_2$), 36.48 (CH$_2$). MS (ES+): 399.19 [M+1].
Calculated analysis for C20H22N4O5 (398.16): C, 60.29; H, 5.57; N, 14.06. Found C, 60.34; H, 5.61; N, 13.97.

Synthesis of 2-[(4-nitrobenzoyl)amino]-N-(2-morpholin-4-ylethyl) benzamide (Compound 1i)

Chemical Formula: C20H22N4O5 Molecular Weight: 398.16

The synthetic procedure followed the general method for step 2 above using Intermediate 1 i (0.50 g, 1.87 mmol) in DMF (8 ml), 2 equivalents of DIPEA (0.65 ml, 3.74 mmol) and 2.2 equivalents of 2-morpholinoethanamine (0.54 ml, 4.11 mmol). The product was recrystallized from ethanol as a white solid. Yield 51% (0.38 g), mp 148° C.

$^1$H NMR (500 MHz, DMSO-d6) δ 12.70 (s, 1H, NH), 8.83 (s, 1H, NH), 8.59 (d, J=8.4 Hz, 1H, ArH), 8.44 (d, 8.9 Hz, 2H, ArH), 8.16 (d, 8.9 Hz, 2H, ArH), 7.85 (dd, J=8.0, 1.5 Hz, 1H, ArH), 7.60 (td, J=8.6, 1.5 Hz, 1H, ArH), 7.27 (td, J=7.5, 1.2 Hz, 1H, ArH), 3.54 (t, J=4.6 Hz, 4H, CH$_2$), 3.44 (q, J=6.5 Hz, 2H, CH$_2$), 2.44 (m, 6H, CH$_2$).
$^{13}$C NMR (126 MHz, DMSO-d6) δ 68.38 (C=O), 162.69 (C=O), 149.41 (ArC), 140.10 (ArC), 138.76 (ArC), 132.21 (ArCH), 128.43 (ArCH), 128.15 (ArCH), 124.13 (ArCH), 123.47 (ArCH), 120.92 (ArC), 120.64 (ArCH), 66.17 (CH$_2$), 56.93 (CH$_2$), 53.20 (CH$_2$), 36.58 (CH$_2$).
MS (ES+): 399.21 [M+1].

Calculated analysis for C20H22N4O5 (398.16): C, 60.29; H, 5.57; N, 14.06. Found C, 60.36; H, 5.54; N, 14.05.

Synthesis of 2-[(2-methylbenzoyl)amino]-N-(2-morpholin-4-ylethyl) benzamide (Compound 1j)

Chemical Formula: C21H25N3O3 Molecular Weight: 367.44

The synthetic procedure followed the general method for step 2 above using Intermediate 1j (0.50 g, 2.11 mmol) in DMF (8 ml), 2 equivalents of DIPEA (0.61 ml, 4.64 mmol) and 2.2 equivalents of 2-morpholinoethanamine (0.74 ml, 4.22 mmol). The product was recrystallized from ethanol as a white solid. Yield 14% (0.11 g), mp 76° C.

$^1$H NMR (500 MHz, DMSO-d6) δ 11.78 (s, 1H, NH), 8.72 (s, 1H, NH), 8.59 (d, J=8.3 Hz, 1H, ArH), 7.78 (dd, J=7.8, 1.5 Hz, 1H, ArH), 7.56 (q, J=23.6 Hz, 2H, ArH), 7.43 (td, J=7.5, 1.4 Hz, 1H, ArH), 7.34 (dt, J=7.3, 3.4 Hz, 2H, ArH), 7.22 (td, J=7.6, 1.2 Hz, 1H, ArH), 3.53 (t, J=4.6 Hz, 4H, CH$_2$), 3.37 (q, J=6.5 Hz, 2H, CH$_2$), 2.45 (d, J=3.9 Hz, 5H, CH$_{2/3}$), 2.39 (t, J=4.7 Hz, 4H, CH$_2$).
$^{13}$C NMR (126 MHz, DMSO-d6) δ 168.22 (C=O), 167.10 (C=O), 138.96 (ArC), 136.44 (ArC), 135.82 (ArC), 131.96 (ArCH), 131.14 (ArCH), 130.24 (ArCH), 128.04 (ArCH), 126.75 (ArCH), 126.07 (ArCH), 122.92 (ArCH), 121.00 (ArC), 120.32 (ArCH), 66.14 (CH$_2$), 56.99 (CH$_2$), 53.19 (CH$_2$), 36.43 (CH$_2$), 19.59 (CH$_3$). MS (ES+): 368.22 [M+1].
Calculated analysis for C21H25N3O3 (367.44): C, 68.64; H, 6.86; N, 11.44. Found C, 68.27; H, 6.71; N, 11.28.

Synthesis of 3,4-dimethoxy-N-(2-[(2-morpholin-4-ylethyl) carbamoyl]phenyl) benzamide (Compound 1l)

Chemical Formula: C22H27N3O5 Molecular Weight: 413.47

The synthetic procedure followed the general method for step 2 above using Intermediate 1l (0.25 g, 0.88 mmol) in DMF (8 ml), 2 equivalents of DIPEA (0.31 ml, 1.77 mmol) and 2.2 equivalents of 2-morpholinoethanamine (0.26 ml, 1.94 mmol). The product was recrystallized from ethanol as a white solid. Yield 22% (0.19 g), mp 106° C.

$^1$H NMR (500 MHz, DMSO-d6) δ 12.47 (s, 1H, NH), 8.79 (s, 1H, NH), 8.64 (d, J=8.4 Hz, 1H, ArH), 7.81 (d, J=7.8 Hz, 1H, ArH), 7.60-7.50 (m, 3H, ArH), 7.23-7.13 (m, 2H, ArH), 3.86 (s, 6H, OCH$_3$), 3.55 (t, J=4.6 Hz, 4H, CH$_2$), 3.45 (q, J=6.5 Hz, 2H, CH$_2$), 2.42 (t, J=4.6 Hz, 6H, CH$_2$).
$^{13}$C NMR (126 MHz, DMSO-d6) δ 168.62 (C=O), 163.98 (ArC), 151.93 (ArC), 148.69 (ArC), 139.52 (ArC), 132.12 (ArCH), 128.06 (ArCH), 126.83 (ArC), 122.50 (ArCH), 120.26 (ArC), 120.07 (ArCH), 119.86 (ArCH), 111.38 (ArCH), 110.45 (ArCH), 66.17 ($CH_2$), 56.98 ($CH_2$), 55.70 ($OCH_3$), 55.45 ($OCH_3$), 53.20 ($CH_2$), 36.52 ($CH_2$).

MS (EI+): 413.2.

Calculated analysis for $C_{22}H_{27}N_3O_5$ (413.47): C, 63.91; H, 6.58; N, 10.16. Found C, 63.54; H, 6.86; N, 10.11

Synthesis of 3,5-dimethoxy-N-(2-[(2-morpholin-4-ylethyl) carbamoyl]phenyl) benzamide (Compound 1m)

Chemical Formula: $C_{22}H_{27}N_3O_5$ Molecular Weight: 413.47

The synthetic procedure followed the general method for step 2 above using Intermediate 1m (0.25 g, 0.88 mmol) in DMF (8 ml), 2 equivalents of DIPEA (0.31 ml, 1.77 mmol) and 2.2 equivalents of 2-morpholinoethanamine (0.26 ml, 1.94 mmol). The product was recrystallized from ethanol as a white solid. Yield 58% (0.21 g), mp 120° C.

$^1$H NMR (500 MHz, DMSO-d6) δ 12.46 (s, 1H, NH), 8.79 (s, NH), 8.61 (dd, J=8.4, 1.2 Hz, 1H, ArH), 7.81 (dd, J=7.9 Hz, 1H, ArH), 7.57 (t, J=7.6 Hz, 1H, ArH), 7.22 (td, J=7.5, 1.3 Hz, 1H, ArH), 7.07 (d, J=2.2 Hz, 2H, ArH), 6.77 (t, J=2.2 Hz, 1H, ArH), 3.84 (d, J=1.5 Hz, 6H, $OCH_3$), 3.54 (t, J=4.6 Hz, 4H, $CH_2$), 3.44 (q, J=6.4 Hz, 2H, $CH_2$), 2.49 (t, J=6.8 Hz, 2H, $CH_2$), 2.42 (t, J=4.7 Hz, 4H, $CH_2$)

$^{13}$C NMR (126 MHz, DMSO-d6) δ 168.49 (C=O), 163.95 (ArC), 160.70 (ArC), 139.12 (ArC), 136.72 (ArC), 132.13 (ArCH), 128.09 (ArCH), 122.89 (ArCH), 120.59 (ArC), 120.22 (ArCH), 104.99 (ArCH), 103.43 (ArCH), 66.16 ($CH_2$), 56.99 ($CH_2$), 55.44 ($OCH_3$), 53.21 ($CH_2$), 36.52 ($CH_2$).

MS (EI+): 413.2.

Calculated analysis for $C_{22}H_{27}N_3O_5$ (413.47): C, 63.91; H, 6.58; N, 10.16. Found C, 63.66; H, 6.43; N, 10.03.

Synthesis of 3,4,5-trimethoxy-N-(2-[(2-morpholin-4-ylethyl) carbamoyl]phenyl) benzamide (Compound 1n)

Chemical Formula: $C_{23}H_{29}N_3O_6$ Molecular Weight: 443.21

The synthetic procedure followed the general method for step 2 above using Intermediate 1n (0.25 g, 0.80 mmol) in DMF (8 ml), 2 equivalents of DIPEA (0.28 ml, 1.60 mmol) and 2.2 equivalents of 2-morpholinoethanamine (0.23 ml, 1.76 mmol). The product was recrystallized from ethanol as a white solid. Yield 52% (0.18 g), mp 117° C.

$^1$H NMR (500 MHz, DMSO-d6) δ 11.78 12.49 (s, 1H, NH), 8.80 (s, 1H, NH), 8.59 (dd, J=8.3, 1.3 Hz, 1H, ArH), 7.81 (dd, J=7.9, 1.5 Hz, 1H, ArH), 7.57 (td, J=8.8, 2.0 Hz, 1H, ArH), 7.26 (s, 2H, ArH), 7.21 (td, J=8.8, 1.4 Hz, 1H, ArH), 3.89 (s, 6H, $OCH_3$), 3.77 (s, 3H, $OCH_3$), 3.54 (t, J=4.7 Hz, 4H, $CH_2$), 3.43 (q, J=6.5 Hz, 2H, $CH_2$), 2.49 (d, J=6.8 Hz, 2H, $CH_2$), 2.41 (t, J=7.3 Hz, 4H, $CH_2$).

$^{13}$C NMR (126 MHz, DMSO-d6) δ 168.54 (C=O), 163.92 (ArC), 152.90 (ArC), 140.63 (ArC), 139.25 (ArC), 132.12 (ArCH), 129.91 (ArC), 128.08 (ArCH), 122.77 (ArCH), 120.62 (ArC), 120.14 (ArCH), 104.56 (ArCH), 66.15 ($CH_2$), 60.13 ($OCH_3$), 56.99 ($CH_2$), 55.94 ($OCH_3$), 53.20 ($CH_2$), 36.49 ($CH_2$).

MS (EI+): 443.2.

Calculated analysis for $C_{23}H_{29}N_3O_6$ (443.21): C, 62.29; H, 6.59; N, 9.47. Found C, 62.29; H, 6.46; N, 9.49.

Synthesis of 3,5-difluoro-N-(2-[(2-morpholin-4-ylethyl) carbamoyl]phenyl) benzamide (Compound 1o)

Chemical Formula: $C_{20}H_{21}F_2N_3O_3$ Molecular Weight: 389.40

The synthetic procedure followed the general method for step 2 above using Intermediate 1o (0.25 g, 0.96 mmol) in DMF (8 ml), 2 equivalents of DIPEA (0.33 ml, 1.92 mmol) and 2.2 equivalents of 2-morpholinoethanamine (0.28 ml, 2.11 mmol).

The product was recrystallized from ethanol as a white solid. Yield 40% (0.15 g), mp 116° C.

$^1$H NMR (500 MHz, DMSO-d6) δ 12.54 (s, 1H, NH), 8.81 (s, 1H, NH), 8.52 (dd, J=8.4, 1.2 Hz, 1H, ArH), 7.83 (dd, J=7.9, 1.5 Hz, 1H, ArH), 7.61-7.59 (m, 1H, ArH), 7.59-7.55 (m, 3H, ArH), 7.26 (td, J=7.6, 1.3 Hz, 2H, ArH), 3.55 (t, J=4.6 Hz, 4H, $CH_2$), 3.44 (q, J=6.1 Hz, 2H, $CH_2$), 2.49 (d, J=6.8 Hz, 1H, $CH_2$), 2.42 (t, J=6.5 Hz, 4H, $CH_2$).

$^{13}$C NMR (126 MHz, DMSO-d6) δ 168.33 (C=O), 163.50 (d, $J_{C-F}$=13.1 Hz, ArC—F), 161.50 (d, $J_{C-F}$=11.2 Hz, ArC—F), 150.10 (ArC), 143.55 (ArC), 138.5 (d, $J_{C-F}$=37.7 Hz, ArC), 132.15 (ArCH), 128.16 ArCH), 123.47 (ArCH), 121.16 (ArC), 120.69 (ArCH), 110.50 (d, $J_{C-F}$=7.04 Hz, ArCH), 110.29 (d, $J_{C-F}$=6.7 Hz, ArCH), 107.50 (ArCH), 66.15 ($CH_2$), 56.98 ($CH_2$), 53.21 ($CH_2$), 36.56 ($CH_2$).

MS (EI+): 389.2.

Calculated analysis for $C_{20}H_{21}F_2N_3O_3$ (389.40): C, 61.69; H, 5.44; N, 10.79.

Found C, 61.56; H, 5.27; N, 10.68.

Synthesis of 2,6-difluoro-N-(2-[(2-morpholin-4-ylethyl) carbamoyl]phenyl) benzamide (Compound 1p)

Chemical Formula: $C_{20}H_{21}F_2N_3O_3$ Molecular Weight: 389.40

The synthetic procedure followed the general method for step 2 above using Intermediate 1p (0.25 g, 0.96 mmol) in DMF (8 ml), 2 equivalents of DIPEA (0.33 ml, 1.92 mmol) and 2.2 equivalents of 2-morpholinoethanamine (0.28 ml, 2.11 mmol). The product was recrystallized from ethanol as a white solid. Yield 61% (0.25 g), mp 136° C.

$^1$H NMR (500 MHz, DMSO-d6) δ 12.03 (s, 1H, NH), 8.76 (s, 1H, NH), 8.52 (dd, J=8.3, 1.2 Hz, 1H, ArH), 7.79 (dd, J=8.0, 1.6 Hz, 1H, ArH), 7.66-7.62 (m, 1H, ArH), 7.62-7.57 (m, 1H, ArH), 7.28 (td, J=7.9, 6.2 Hz, 3H, ArH), 3.53 (t, J=4.7 Hz, 4H, $CH_2$), 3.37 (q, J=6.4 Hz, 2H, $CH_2$), 2.46 (t, J=6.8 Hz, 2H, $CH_2$), 2.39 (t, J=5.0 Hz, 4H, $CH_2$).

$^{13}$C NMR (126 MHz, DMSO-d6) δ 167.96 (C=O), 159.76 (d, $J_{C-F}$=7.1 Hz, ArC—F), 157.72 (d, $J_{C-F}$=5.5 Hz, ArC—F), 137.98 (ArC), 132.79 (t, $J_{C-F}$=20.4 Hz, ArCH), 132.13 (ArCH), 128.14 (ArCH), 127.75 (ArC), 123.77 (ArCH), 121.32 (ArC), 120.54 (ArCH), 112.52 (d, $J_{C-F}$=3.8 Hz, ArCH), 112.34 (d, $J_{C-F}$=4.2 Hz, ArCH), 111.50 (ArC), 66.13 ($CH_2$), 56.92 ($CH_2$), 53.18 ($CH_2$), 36.45 ($CH_2$).

MS (EI+): 389.2.

Calculated analysis for $C_{20}H_{21}F_2N_3O_3$ (389.40): C, 61.69; H, 5.44; N, 10.79.

Found C, 61.68; H, 5.31; N, 10.82.

Synthesis of 2,4-difluoro-N-(2-[(2-morpholin-4-ylethyl) carbamoyl]phenyl) benzamide (Compound 1q)

Chemical Formula: C20H21F2N3O3 Molecular Weight: 389.40

The synthetic procedure followed the general method for step 2 above using Intermediate 1q (0.25 g, 0.96 mmol) in DMF (8 ml), 2 equivalents of DIPEA (0.33 ml, 1.92 mmol) and 2.2 equivalents of 2-morpholinoethanamine (0.28 ml, 2.11 mmol). The product was recrystallized from ethanol as a white solid. Yield 55% (0.21 g), mp 121° C.

$^1$H NMR (500 MHz, DMSO-d6) δ 12.00 (s, 1H, NH), 8.72 (s, 1H, NH), 8.55 (d, J=8.3 Hz, 1H, ArH), 7.98 (tt, J=8.8, 6.6 Hz, 1H, ArH), 7.76 (dd, J=7.9, 1.6 Hz, 1H, ArH), 7.57 (td, J=8.5, 1.5 Hz, 1H, ArH), 7.49 (td, J=11.6, 2.5 Hz, 1H, ArH), 7.30 (td, J=8.4, 3.8 Hz, 1H, ArH), 7.24 (td, J=7.6, 1.2 Hz, 1H, ArH), 3.53 (t, J=5.6 Hz, 4H, CH$_2$), 3.39 (q, J=6.3 Hz, 2H, CH$_2$), 2.48 (t, J=6.7 Hz, 2H, CH$_2$), 2.41 (t, J=4.6 Hz, 4H, CH$_2$).

$^{13}$C NMR (126 MHz, DMSO-d6) δ 168.02 (C=O), 163.20 (d, J$_{C-F}$=5.3 Hz, ArC—F), 158.10 (d, J$_{C-F}$=10.5 Hz, ArC—F), 138.24 (d, J$_{C-F}$=5.4 Hz, ArC), 132.69 (d, J$_{C-F}$ 14.9 Hz, ArC), 131.83 (ArCH), 128.02 (ArCH), 123.38 (ArCH), 121.80 (ArC), 121.04 (ArCH), 119.75 (ArC), 112.57 (d, J$_{C-F}$=3.3 Hz, ArCH), 112.41 (d, J$_{C-F}$=3.7 Hz, ArCH), 104.99 (ArCH), 66.16 (CH$_2$), 56.98 (CH$_2$), 53.18 (CH$_2$), 36.44 (CH$_2$). MS (EI+): 389.2.

Calculated analysis for C20H21F2N3O3 (389.40): C, 61.69; H, 5.44; N, 10.79.

Found C, 61.59; H, 5.24; N, 10.70.

Example 2

Synthesis of Compounds of Series 2

The compounds of series 2 have the general formula

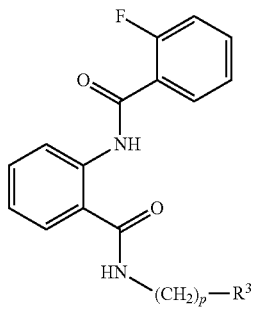

| Compound | R$^1$ |
|---|---|
| 2a | —N(morpholine) |
| 2b | —(pyridin-2-yl) |
| 2c | —N(pyrrolidine) |
| 2d | —N(piperidine) |
| 2e | —N(piperazine)NH |
| 2f | —NH$_2$ |

Step 1—Synthesis of Example Compounds

Synthesis of 2-[(2-fluorobenzoyl)amino]-N-2-morpholin-4-ylpropyl)benzamide (Compound 2a)

Chemical Formula: C21H24FN3O3 Molecular Weight: 385.43

The synthetic procedure followed the general method for step 2 above using Intermediate 1a (0.50 g, 2.07 mmol) in DMF (8 ml), 2 equivalents of DIPEA (0.72 ml, 4.14 mmol) and 2.2 equivalents of 3-morpholinopropan-1-amine (0.67 ml, 4.56 mmol). The product was recrystallized from ethanol as a white solid. Yield 17% (0.14 g), mp 108° C.

$^1$H NMR (500 MHz, DMSO-d6) δ 12.06 (s, 1H, NH), 8.82 (s, 1H, NH), 8.58 (d, J=8.3 Hz, 1H, ArH), 7.89 (td, J=7.7, 1.9 Hz, 1H, ArH), 7.77 (dd, J=7.9, 1.5 Hz, 1H, ArH), 7.69-7.61 (m, 1H, ArH), 7.57 (td, J=8.6, 1.5 Hz, 1H, ArH), 7.44-7.36 (m, 2H, ArH), 7.23 (td, J=7.6, 1.2 Hz, 1H, ArH), 3.55 (t, J=4.6 Hz, 4H, CH$_2$), 3.30 (dd, J=7.0 Hz, 2H, CH$_2$), 2.32 (t, J=6.6 Hz, 6H, CH$_2$), 1.69 (p, J=7.0 Hz, 2H, CH$_2$).

$^{13}$C NMR (126 MHz, DMSO-d6) δ 168.01 (C=O), 160.86 (d, J$_{C-F}$=146.2 Hz, ArC—F), 158.29 (C=O), 138.37 (ArC), 133.76 (d, J$_{C-F}$=8.8 Hz, ArCH), 131.78 (ArCH), 130.64 (d, J$_{C-F}$=1.3 Hz, ArCH), 128.01 (ArCH), 125.01 (d, J$_{C-F}$=3.8 Hz, ArCH), 123.24 (ArCH), 122.91 (ArC), 121.70 (ArC), 120.94 (ArCH), 116.64 (d, J$_{C-F}$=22.9 Hz, ArCH), 66.16 (CH$_2$), 55.99 (CH$_2$), 53.30 (CH$_2$), 37.75 (CH$_2$), 25.59 (CH$_2$).

MS (ES+): 386.18 [M+1].

Calculated analysis for C21H24FN3O3 (385.43): C, 65.44; H, 6.28; N, 10.09. Found C, 65.44; H, 6.39; N, 10.94.

Synthesis of 2-[(4-fluorobenzoyl)amino]-N-(pyridin-3-ylmethyl)benzamide (Compound 2b)

Chemical Formula: C21H18FN3O2 Molecular Weight: 363.38

The synthetic procedure followed the general method for step 2 above using Intermediate 1a (0.50 g, 2.07 mmol) in DMF (8 ml), 2 equivalents of DIPEA (0.72 ml, 4.14 mmol) and 2.2 equivalents of 2-(pyridin-2-yl) ethanamine (0.55 ml, 4.56 mmol). The product was recrystallized from ethanol as a brown solid. Yield 44% (0.34 g), mp 88° C.

$^1$H NMR (500 MHz, DMSO-d6) δ 11.99 (s, 1H, NH), 8.89 (s, 1H, NH), 8.57 (d, J=8.4 Hz, 1H, ArH), 8.48 (d, J=6.6 Hz, 1H, ArH), 7.88 (td, J=7.8, 1.8 Hz, 1H, ArH), 7.72 (dd, J=7.8, 1.6 Hz, 1H, ArH), 7.68 (m, 2H, ArH), 7.56 (td, J=17.4, 1.3 Hz, 1H, ArH), 7.41 (m, 2H, ArH), 7.27 (d, J=7.7 Hz, 1H, ArH), 7.22 (td, J=7.6, 1.3 Hz, 1H, ArH), 7.16 (td, J=7.5, 1.2 Hz, 1H, ArH), 3.63 (m, 2H, CH$_2$), 3.00 (t, J=7.2 Hz, 2H, CH$_2$).

$^{13}$C NMR (126 MHz, DMSO-d6) δ 168.03 (C=O), 160.88 (d, $J_{C-F}$=144.9 Hz, ArC—F), 158.94 (ArC), 158.30 (ArC), 148.97 (ArCH), 138.37 (ArC), 136.33 (ArCH), 133.76 (d, $J_{C-F}$=8.8 Hz, ArCH), 131.81 (ArCH), 130.60 (d, $J_{C-F}$=1.3 Hz, ArCH), 127.99 (ArCH), 125.02 (d, $J_{C-F}$=2.6 Hz, ArCH), 123.23 (ArCH), 123.12 (ArCH), 121.60 (ArC), 121.42 (ArCH), 120.89 (ArCH), 116.49 (d, $J_{C-F}$=22.7 Hz, ArCH), 36.98 (CH$_2$).

MS (ES+): 362.13 [M+1]. High resolution MS: 364.1456 [M−1]—Composition to C21H19FN3O2 (delta ppm 0.1) or C18H21F5O2 (delta ppm −0.1).

Synthesis of 2-[(4-fluorobenzoyl)amino]-N-(pyrrolidin-3-ylmethyl)benzamide (Compound 2c)

Chemical Formula: C20H22FN3O2 Molecular Weight: 355.17

The synthetic procedure followed the general method for step 2 above using

Intermediate 1a (0.50 g, 2.07 mmol) in DMF (8 ml), 2 equivalents of DIPEA (0.72 ml, 4.14 mmol) and 2.2 equivalents of 2-(pyrrolidin-1-yl) ethanamine (0.58 ml, 4.56 mmol). The product was recrystallized from ethanol as a yellow/brown solid. Yield 41% (0.30 g), mp 89° C.

$^1$H NMR (500 MHz, DMSO-d6) δ 12.04 (s, 1H, NH), 8.74 (s, 1H, NH), 8.58 (d, J=8.4 Hz, 1H, ArH), 7.88 (td, J=7.7, 1.9 Hz, 1H, ArH), 7.77 (dd, J=7.9, 1.5 Hz, 1H, ArH), 7.66 (m, 1 H, ArH), 7.57 (td, J=8.6, 1.5 Hz, 1H, ArH), 7.41 (m, 2H, ArH), 7.23 (td, J=7.6, 1.2 Hz, 1H, ArH), 3.38 (q, J=6.5 Hz, 2H, CH$_2$), 2.57 (t, J=6.8 Hz, 2H, CH$_2$), 2.47 (t, J=6.6, Hz, 4H, CH$_2$), 1.71-1.60 (m, 4H, CH$_2$).

$^{13}$C NMR (126 MHz, DMSO-d6) δ 167.98 (C=O), 161.44 (d, $J_{C-F}$=144.9 Hz, ArC—F), 158.29 (C=O), 138.38 (ArC), 133.77 (d, $J_{C-F}$=8.6 Hz, ArCH), 131.83 (ArCH), 130.60 (ArCH), 128.04 (ArCH), 125.03 (d, $J_{C-F}$=3.8 Hz, ArCH), 123.27 (ArCH), 122.91 (d, $J_{C-F}$=12.6 Hz, ArC), 121.59 (ArCH), 120.93 (ArCH), 116.58 (d, $J_{C-F}$=22.7 Hz, ArC), 54.49 (CH$_2$), 53.56 (CH$_2$), 38.58 (CH$_2$), 23.12 (CH$_2$).

MS (ES+): 356.15 [M+1].

Calculated analysis for C20H22FN3O2 (355.17): C, 67.59; H, 6.24; N, 11.82. Found C, 67.66; H, 6.19; N, 11.67.

Synthesis of 2-[(4-fluorobenzoyl)amino]-N-(piperidin-3-ylmethyl)benzamide (Compound 2d)

Chemical Formula: C21H24FN3O2 Molecular Weight: 369.43

The synthetic procedure followed the general method for step 2 above using Intermediate 1a (0.50 g, 2.07 mmol) in DMF (8 ml), 2 equivalents of DIPEA (0.72 ml, 4.14 mmol) and 2.2 equivalents of 2-(piperidin-1-yl) ethanamine 16d (0.65 ml, 4.56 mmol). The product was recrystallized from ethanol as a white solid. Yield 51% (0.39 g), mp 94° C.

$^1$H NMR (500 MHz, DMSO-d6) δ 11.99 (s, 1H, NH), 8.69 (s, 1H, NH), 8.57 (d, J=8.3 Hz, 1H, ArH), 7.88 (td, J=17.1, 1.7 Hz, 1H, ArH), 7.76 (d, J=9.1 Hz, 1H, ArH), 7.67-7.62 (m, 1H, ArH), 7.56 (t, J=16.4 Hz, 1H, ArH), 7.42-7.37 (m, 1H, ArH), 7.23 (t, J=15.4 Hz, 2H, ArH), 3.36 (q, J=19.6 Hz, 2H, CH$_2$), 2.43 (t, J=14.1 Hz, 2H, CH$_2$), 2.35 (t, J=18.6 Hz, 4H, CH$_2$), 1.44 (q, J=22.6 Hz, 4H, CH$_2$), 1.34 (d, J=15.1 Hz, 2H, CH$_2$).

$^{13}$C NMR (126 MHz, DMSO-d6) δ 167.99 (C=O), 160.89 (d, $J_{C-F}$=155.0 Hz, ArC—F), 158.31 (C=O), 154.28 (ArC), 138.39 (ArC), 133.76 (d, $J_{C-F}$=8.8 Hz, ArCH), 131.77 (ArCH), 130.60 (d, $J_{C-F}$=1.8 Hz, ArCH), 128.01 (ArCH), 125.00 (d, $J_{C-F}$=3.7 Hz, ArCH), 123.26 (ArCH), 121.81 (ArC), 120.97 (ArCH), 116.56 (d, $J_{C-F}$=22.8 Hz, ArCH), 57.31 (CH$_2$), 53.96 (CH$_2$), 36.87 (CH$_2$), 25.56 (CH$_2$), 23.99 (CH$_2$).

MS (EI+): 369.19.

Calculated analysis for C21H24FN3O2 (369.43): C, 68.27; H, 6.55; N, 11.37. Found C, 67.95; H, 6.82; N, 11.44.

Synthesis of N-(2-aminoethyl)-2-(2-fluorobenzamido) benzamide (Compound 2f)

Chemical Formula: C16H16FN3O2 Molecular Weight: 301.32

The synthetic procedure followed the general method for step 2 above using Intermediate 1a (0.50 g, 2.07 mmol) in DMF (8 ml), 2 equivalents of DIPEA (0.72 ml, 4.14 mmol) and 2.2 equivalents of ethane-1,2-diamine (0.31 ml, 4.56 mmol). The product was recrystallized from ethanol as a yellow solid. Yield 43% (0.27 g), mp 96° C.

$^1$H NMR (500 MHz, DMSO-d6) δ 12.51 (s, 1H, NH), 11.62 (s, 2H, NH$_2$), 8.80 (s, 1H, NH), 8.60 (dd, J=9.4, 1.1 Hz, 1H, ArH), 8.03 (dd, J=9.4, 1.6 Hz, 1H, ArH), 7.98 (dd, J=9.7, 1.6 Hz, 2H, ArH), 7.72-7.64 (m, 2H, ArH), 7.62 (td, J=16.6, 1.9 Hz, 1H, ArH), 7.26 (td, J=16.4, 1.1 Hz, 1H, ArH), 3.91 (s, 4H, CH$_2$).

$^{13}$C NMR (126 MHz, DMSO-d6) δ 168.24 (C=O), 160.87 (d, $J_{C-F}$=151.5 Hz, ArC—F), 158.29 (C=O), 154.31 (ArC), 138.41 (ArC), 133.74 (d, $J_{C-F}$=9.5 Hz, ArCH), 131.80 (ArCH), 130.61 (d, $J_{C-F}$=1.8 Hz, ArCH), 128.21 (ArCH), 125.02 (d, $J_{C-F}$=3.6 Hz, ArCH), 123.22 (ArCH), 121.65 (ArC), 120.86 (ArCH), 116.57 (d, $J_{C-F}$=22.5 Hz, ArCH), 42.79 (CH$_2$), 40.88 (CH$_2$).

MS (EI+): 301.12. High resolution MS: 302.1301 [M−1]. Composition: C21H18O2 (delta ppm −0.1), C13H19O2F5 (delta ppm 0.4), C16H17O2N3F1 (delta ppm 0.6).

Example 3

Synthesis of Compounds of Series 3

The compounds of series 3 have the general formula

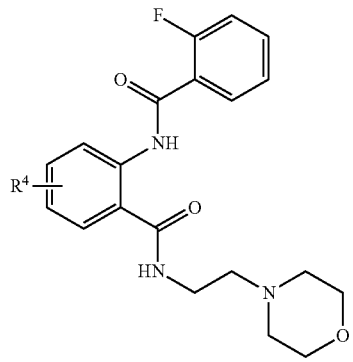

| Compound | R$^4$ |
|---|---|
| 3a | 3-OCH$_3$ |
| 3b | 3-CH$_3$ |
| 3c | 5-I |
| 3d | 6-Cl |

Step 1—Synthesis of Intermediates

Synthesis of 2-(2-fluorophenyl)-8-methoxy-3,1-benzoxazin-4-one (Intermediate 3a)

Chemical Formula: C15H10FNO3 Molecular Weight: 271.24

The synthetic procedure followed the general method set out above for step 1 using 2-amino-3-methoxybenzoic acid (0.50 g, 2.99 mmol) dissolved in pyridine (5 ml) and 2.2 equivalent of 2-fluorobenzoyl chloride (0.79 ml, 6.58 mmol). Collected as a white solid, yield 92% (0.75 g), mp 131° C.

$^1$H NMR (500 MHz, DMSO-d6) δ 8.08 (td, J=7.7, 1.8 Hz, 1H, ArH), 7.72 (d, J=1.6 Hz, 1H, ArH), 7.71 (d, J=1.6 Hz, 1H, ArH), 7.63-7.54 (m, 2H, ArH), 7.42 (m, 2H, ArH), 3.97 (s, 3H, OCH$_3$).

13C NMR (126 MHz, DMSO-d6) δ 160.31 (d, $J_{C-F}$=257.0 Hz, ArC—F), 158.73 (ArC=O), 154.15 (ArC), 152.92 (ArC), 135.83 (ArC), 134.31 (d, $J_{C-F}$=8.8 Hz, ArCH), 131.14 (ArCH), 129.48 (ArCH), 124.79 (d, $J_{C-F}$=3.8 Hz, ArCH), 118.90 (d, $J_{C-F}$=10.1 Hz, ArC), 118.78 (ArCH), 118.32 (ArCH), 117.22 (d, $J_{C-F}$=21.4 Hz, ArCH), 56.34 (OCH3).

MS (APCI+): 272.07 [M+1].

Synthesis of 2-(2-fluorophenyl)-8-methoxy-3,1-benzoxazin-4-one (Intermediate 3b)

Chemical Formula: C15H10FNO2 Molecular Weight: 255.21

The synthetic procedure followed the general method set out above for step 1 using 2-amino-3-methylbenzoic acid (0.50 g, 3.31 mmol) dissolved in pyridine (5 ml) and 2.2 equivalent of 2-fluorobenzoyl chloride (0.87 ml, 7.28 mmol). Collected as a white solid, yield 97% (0.81 g), mp 106° C.

$^1$H NMR (500 MHz, DMSO-d6) δ 8.13 (td, J=7.7, 1.9 Hz, 1H, ArH), 8.0 (d, J=8.8Hz, 1H, ArH), 7.84 (d, J=8.8, 1H, ArH), 7.75-7.67 (m, 1H, ArH), 7.55 (t, J=7.7 Hz, 1H, ArH), 7.47-7.40 (m, 2H, ArH), 2.58 (s, 3H, CH$_3$).

$^{13}$C NMR (126 MHz, DMSO-d6) δ 160.51 (d, $J_{C-F}$=259.6 Hz, ArC—F), 159.01 (ArC=O), 153.06 (ArC), 144.29 (ArC), 137.40 (ArCH), 135.61 (ArC), 134.44 (d, $J_{C-F}$=8.82 Hz, ArCH), 131.07 (ArCH), 128.42 (ArCH), 125.54 (ArCH), 124.82 (d, $J_{C-F}$=3.8 Hz, ArCH), 118.93 (d, $J_{C-F}$=1.3 Hz, ArC), 117.32 (d, $J_{C-F}$=21.4 Hz, ArC), 116.78 (ArCH), 16.50 (CH$_3$).

MS (APCI+): 256.07 [M+1].

Synthesis of 2-(2-fluorophenyl)-8-methoxy-3,1-benzoxazin-4-one (Intermediate 3c)

Chemical Formula: C14H7FINO2 Molecular Weight: 367.11

The synthetic procedure followed the general method set out above for step 1 using 2-amino-5-iodobenzoic acid (0.50 g, 1.90 mmol) dissolved in pyridine (5 ml) and 2.2 equivalent of 2-fluorobenzoyl chloride (0.50 ml, 4.18 mmol). Collected as a white solid, yield 90% (0.63 g), mp 159° C.

$^1$H NMR (500 MHz, DMSO-d6) δ 8.41 (d, J=2.0 Hz, 1H, ArH), 8.26 (dd, J=8.4, 2.0 Hz, 1H, ArH), 8.09 (td, J=7.8, 1.8 Hz, 1H, ArH), 7.75-7.69 (m, 1H, ArH), 7.50 (d, J=8.4 Hz, 1H, ArH), 7.44 (m, 2H, ArH).

$^{13}$C NMR (126 MHz, DMSO-d6) δ 160.48 (d, $J_{C-F}$=258.3 Hz, ArC—F), 157.35 (ArC=O), 154.59 (ArC), 145.39 (ArC), 145.12 (ArCH), 135.85 (ArCH), 134.74 (d, $J_{C-F}$=8.8 Hz, ArCH), 131.10 (ArCH), 128.95 (ArCH), 124.86 (d, $J_{C-F}$=3.8 Hz, ArCH), 118.82 (ArC), 118.45 (d, $J_{C-F}$=8.8 Hz, ArC), 117.28 (d, $J_{C-F}$=21.4 Hz, ArCH), 93.91 (ArC—I).

Synthesis of 5-chloro-2-(2-fluorophenyl)-3,1-benzoxazin-4-one (Intermediate 3d)

Chemical Formula: C14H7ClFNO2 Molecular Weight: 275.66

The synthetic procedure followed the general method set out above for step 1 using 2-amino-6-chlorobenzoic acid (0.50 g, 2.91 mmol) dissolved in pyridine (5 ml) and 2.2 equivalent of 2-fluorobenzoyl chloride (0.76 ml, 6.41 mmol). Collected as a white solid, yield 89% (0.71 g), mp 104° C.

1H NMR (500 MHz, DMSO-d6) δ 8.01 (td, J=17.6, 1.8 Hz, 1H, ArH), 7.90 (t, J=16.1 Hz, 1H, ArH), 7.71 (dd, J=9.1, 1.2 Hz, 2H, ArH), 7.67 (dd, J=9.1, 1.2 Hz, 1H, ArH), 7.46-7.42 (m, 2H, ArH), $^{13}$C NMR (126 MHz, DMSO-d6) δ 160.53 (d, $J_{C-F}$=256.9 Hz, ArC—F), 155.43 (ArC=O), 148.53 (ArC), 144.39 (ArC), 136.6 (ArCH), 134.81 (d, $J_{C-F}$=10.1 Hz, ArCH), 134.01 (ArC), 131.09 (ArCH), 130.93 (ArCH), 126.44 (ArCH), 124.86 (d, $J_{C-F}$=3.9 Hz, ArCH), 118.18 (d, $J_{C-F}$=10.3 Hz, ArC), 117.28 (d, $J_{C-F}$=22.3 Hz, ArCH), 114.77 (ArC—Cl).

MS (EI+): 275.01.

Step 2—Synthesis of Example Compounds

Synthesis of 2-[(2-fluorobenzoyl)amino]-3-methoxy-N-(2-morpholin-4-ylethyl) benzamide (Compound 3a)

Chemical Formula: C21H24FN3O4 Molecular Weight: 401.43

The synthetic procedure followed the general method for step 2 using Intermediate 3a (0.50 g, 1.84 mmol) in DMF (8 ml), 2 equivalents of DIPEA (0.64 ml, 3.69 mmol) and 2.2 equivalents of 2-morpholinoethanamine (0.53 ml, 4.06 mmol). The product was recrystallized from ethanol as a white solid. Yield 14% (0.27 g), mp 131° C.

$^1$H NMR (500 MHz, DMSO-d6) δ 9.53 (s, 1H, NH), 8.02 (s, 1H, NH), 7.79 (t, J=15.1 Hz, 1H, ArH), 7.60 (q, J=7.0 Hz, 1H, ArH), 7.38-7.30 (m, 3H, ArH), 7.21 (d, J=8.2 Hz, 1H, ArH), 7.12 (d, J=7.7 Hz, 1H, ArH), 3.81 (s, 3H, OCH$_3$), 3.31 (t, J=10.1 Hz, 6H, CH$_2$), 2.33 (m, 6H, CH$_2$).

$^{13}$C NMR (126 MHz, DMSO-d6) δ 166.71 (C=O), 159.56 (d, $J_{C-F}$=249.5 Hz, ArC—F), 154.59 (C=O), 144.51 (ArC), 138.35 (ArC), 134.90 (d, $J_{C-F}$=1.3 Hz, ArC), 133.09 (d, $J_{C-F}$=1.3 Hz, ArCH), 130.62 (ArCH), 127.27 (ArCH), 124.50 (ArCH), 119.74 (ArCH), 118.6 (ArC), 116.34 (d, $J_{C-F}$=22.7 Hz, ArCH), 113.45 (ArCH), 66.05 (CH$_2$), 57.03 (CH$_2$), 56.04 (OCH$_3$), 53.14 (CH$_2$), 36.23 (CH$_2$).

MS (ES+): 402.21 [M+1].

Calculated analysis for C21H24FN3O4 (401.43): C, 62.83; H, 6.03; N, 10.47. Found C, 62.76; H, 6.17; N, 10.53.

Synthesis of 2-[(2-fluorobenzoyl)amino]-3-methyl-N-(2-morpholin-4-ylethyl) benzamide (Compound 3b)

Chemical Formula: C21H24FN3O3, Molecular Weight: 385.43

The synthetic procedure followed the general method for Step 2 using 2-(2-fluorophenyl)-8-methyl-3,1-benzoxazin-4-one (0.50 g, 1.96 mmol) in DMF (8 ml), 2 equivalents of DIPEA (0.68 ml, 3.91 mmol) and 2.2 equivalents of 2-morpholinoethanamine (0.57 ml, 4.31 mmol). The product was recrystallized from ethanol as a white solid. Yield 42% (0.32 g), mp 165° C.

$^1$H NMR (500 MHz, DMSO-d6) δ 9.96 (s, 1H, NH), 8.12 (s, 1H, NH), 7.80 (td, J=7.6, 1.9 Hz, 1H, ArH), 7.61 (td, J=7.4, 1.9 Hz, 1H, ArH), 7.37 (m, 4H, ArH), 7.30 (t, J=7.6 Hz, 1H, ArH), 3.32 (d, J=5.4 Hz, 4H, CH$_2$), 2.39 (t, J=6.8 Hz, 2H, CH$_2$), 2.32 (m, 6H, CH$_2$), 2.27 (s, 3H, CH$_3$).

$^{13}$C NMR (126 MHz, DMSO-d6) δ 167.43 (C=O), 162.08 (d, $J_{C-F}$=206.6 Hz, ArC—F), 158.45 (C=O), 135.89 (ArC), 133.90 (ArC), 133.42 (ArC), 133.04 (d, $J_{C-F}$=8.8 Hz, ArCH), 131.88 (ArCH), 130.36 (d, $J_{C-F}$=1.3 Hz, ArCH), 126.37 (ArCH), 125.59 (ArCH), 125.10 (ArCH), 124.62 (d, $J_{C-F}$=2.5 Hz, ArC), 116.30 (d, $J_{C-F}$=22.7 Hz, ArCH), 66.08 (CH$_2$), 57.04 (CH$_2$), 53.16 (CH$_2$), 36.30 (CH$_2$), 18.22 (CH$_3$).

MS (ES+): 386.22 [M+1].

Calculated analysis for C21H24FN3O3 (385.43): C, 65.44; H, 6.28; N, 10.90. Found C, 65.66; H, 6.27; N, 10.96.

Synthesis of 2-[(2-fluorobenzoyl)amino]-2-chloro-N-(2-morpholin-4-ylethyl) benzamide (Compound 3d)

Chemical Formula: C20H21FClN3O3 Molecular Weight: 405.85

The synthetic procedure followed the general method for Step 2 using 2-(2-fluorophenyl)-5-chloro-3,1-benzoxazin-4-one (0.50 g, 1.83 mmol) in DMF (8 ml), 2 equivalents of DIPEA (0.64 ml, 3.65 mmol) and 2.2 equivalents of 2-morpholinoethanamine (0.53 ml, 4.02 mmol). The product was recrystallized from ethanol as a yellow solid. Yield 33% (0.25 g), mp 121° C.

$^1$H NMR (500 MHz, DMSO-d6) δ 9.60 (s, 1H, NH), 8.60 (s, 1H, NH), 7.97 (dd, J=8.6 Hz, 1H, ArH), 7.87 (td, J=15.6, 1.8 Hz, 1H, ArH), 7.67-7.63 (m, 1H, ArH), 7.48 (t, 16.5 Hz, 1H, ArH), 7.42-7.36 (m, 3H, ArH), 3.48 (t, J=9.3 Hz, 4H, CH$_2$), 3.38 (q, J=19.5 Hz, 2H, CH$_2$), 2.43 (t, J=13.7 Hz, 2H, CH$_2$), 2.33 (s, 4H, CH$_2$).

$^{13}$C NMR (126 MHz, DMSO-d6) δ 164.21 (C=O), 162.52 (d, $J_{C-F}$=114.8 Hz, ArC—F), 158.45 (C=O), 155.98 (ArC), 142.8 (ArC), 136.0 (ArC), 133.97 (d, $J_{C-F}$=9.4 Hz, ArCH), 130.87 (ArCH), 130.24 (ArCH), 130.20 (d, $J_{C-F}$=19.9 Hz, ArC), 125.94 (ArCH), 124.99 (d, $J_{C-F}$=3.4 Hz, ArCH), 122.60 (ArCH), 116.44 (d, $J_{C-F}$=23.0 Hz, ArCH), 66.08 (CH$_2$), 56.74 (CH$_2$), 53.16 (CH$_2$), 36.47 (CH$_2$).

MS (EI+): 405.12.

Calculated analysis for C20H21FClN3O3 (405.85): C, 59.19; H, 5.22; N, 10.35.

Found C, 59.40; H, 5.21; N, 10.38.

Biological Examples

Materials and Methods

Cloning Procedures

NF-κB Luciferase Reporter Plasmid

NF-κB luciferase assays were carried out using the 3×κB luciferase reporter plasmid, which was a kind gift from Professor Ron Hay (University of St. Andrews). A pcDNA3.1 plasmid containing the LacZ sequence was used as a control for transfection efficiency (gift from Professor Trevor Dale, School of Biosciences, Cardiff University). For positive and negative controls pGL3 luciferase reporter vectors (Promega) were used, pGL3control and pGL3basic, respectively.

Cell Culture Maintenance and Storage

Experimental Cell Lines

The human embryonic kidney cells (HEK-293) were a gift from Prof. Vladimir Buchman (School of Biosciences, Cardiff University). The human breast cancer cell lines, MDA-MB-231, SKBR3 and ZR-7S-1 were a gift from Dr. Julia Gee (Department of Pharmacy and Pharmaceutical Sciences, Cardiff University). The human normal breast cancer cell line MCF-10A was a gift from Dr. Torsten Stein (Division of Cancer Sciences and Molecular Pathology, University of Glasgow). Descriptions of the main cell lines used are outlined below:

HEK-293 is a non-tumorigenic cell line derived from human embryonic kidney cells. HEK-293 cells are convenient for our investigation, because they are easily transfected and have undetectable basal level of Bcl-3 protein.

MDA-MB-231 is a highly metastatic, human basal epithelial cell line isolated from the pleural effusion of an adenocarcinoma. The cells are 'triple negative' as they lack estrogen, progesterone and ERBB2 receptor and they strongly over-express EGFR. The expression of receptors in this line has been confirmed by the host laboratory.

SKBR3 cell line is a poorly metastatic human luminal epithelial cell line derived from a pleural effusion. SKBR3 cells are estrogen and progesterone receptor negative, over-express the ERBB2 receptor and have very low levels of the EGFR receptor.

The ZR-7S-1 cell line is a moderately metastatic human luminal epithelial cell line derived from a malignant ascitic effusion with infiltrating ductal carcinoma. ZR-7S-1 cells are oestrogen and progesterone receptor positive. They express very low levels of the ErbB2 receptor and over-express EGFR.

MCF-10A is a mammary epithelial cell line and is considered as a model of non-tumorigenic mammary cells. MCF-10 cells were derived from a mammary tissue from a 36-year-old woman in a good health and the immortalized MCF-10A line can grow in culture and has a stable, near-diploid karyotype with modest genetic modifications typical of culture-adapted breast epithelial cells.

Maintenance of Cell Lines

The HEK-293 cell line was maintained in Dulbecco's modified Eagle's medium (DMEM, Invitrogen) supplemented with 10% v/v foetal bovine serum (FBS, Sigma, Dorset, UK), penicillin (50 u/ml, Invitrogen), streptomycin (50 u/ml, Invitrogen) and L-glutamine (2 mM, Invitrogen). The MDA-MB-231, ZR-75-1 and SKBR3 cell lines were maintained in RPMI medium (Invitrogen) supplemented with 10% v/v FBS, penicillin (50 u/ml Invitrogen) streptomycin (50 u/ml, Invitrogen) and L-glutamine (2 mM, Invitrogen). MCF-10A cell line was maintained in Dulbecco's modified Eagle's medium nutrient mixture F-12 (DMEM/F-12, Invitrogen) supplemented with 5% v/v horse serum (Sigma, Dorset, UK), penicillin (50 u/ml, Invitrogen), streptomycin (50 u/ml, Invitrogen), epidermal growth factor (EGF, 20 ng/ml, Sigma), hydrocortisone (0.5 mg/ml, Sigma), cholera toxin (100 mg/ml, Sigma) and insulin (10 μg/ml, Sigma).

All cell lines were incubated at 37° C. and 5% $CO_2$ in T25 or T80 tissue culture flasks (Nunc, Leics, UK) and were routinely passaged every 3-8 days at a split ratio of 1:4-1:12, when they became 80-90% confluent.

Cell Based Assays

Cell Titre Blue Viability Assay

The viability of cells at experimental endpoints for particular assays was determined using the Cell Titre Blue reagent (Promega, Southampton, UK). This reagent measures the cellular metabolic activity using resazurin as an indicator dye. Viable cells, therefore metabolically active, will reduce resazurin into highly fluorescent resofurin. The resulting fluorescence levels are measured and indicate cell viability.

Cells were plated at low confluency into 96 well plates in 100 μl of complete growth media in triplicates and were incubated at 37° C. in 5% $CO_2$ for the desired test exposure period. For each 100 μl of media in 96 well plates, 20 μl Cell Titre Blue reagent was added followed by incubation for an hour at 37° C. in 5% $CO_2$. Fluorescence was then measured by setting excitation/emission wavelengths to 560/590 nm on a Flurostar Optima plate reader (BMG tabtech, Bucks, UK).

Cell Count

To establish cell viability over time period of three days, respective cells were seeded at low confluency into 96 well plates in 100 μl of complete growth media in triplicates and were incubated at 37° C. in 5% $CO_2$. After 24 hrs, cells from triplicate wells for the first time point were detached using 0.25% Trypsin/EDTA (Invitrogen) and resuspended in complete growth media and individually counted. The same was done for each cell line at 48 hrs and 72 hrs post-seeding.

Determination of NF-κB Activity in Cells

For NF-κB luciferase assays, cells were seeded into clear bottom black 96-well plates (Corning Inc., Lowell, US) in antibiotic free culture media in appropriate density. After 24 hrs, cells were transfected with 10 ng of 3×κB luciferase plasmid and 10 ng of pcDNA3.1-LacI plasmid per well. Empty pcDNA3.1 plasmid was also included to normalize the total weight of DNA transfected to 100 ng. For positive and negative controls respectively, 10 ng of pGL3control or pGL3basic were transfected in place of 3×κB luciferase plasmid. Transfection was carried out using Lipofectamine LTX reagents (Invitrogen, Paisley, UK).

After 48 hrs post-transfection with luciferase reporter plasmid, the media was aspirated and cells were lyzed using 50 μl/well of Glo-lysis buffer (Promega, Southampton, UK). The plate was left on a rocker for 20 min to facilitate complete cell lysis. Then, 20 μl of lysate from each well was removed and transferred into a new clear bottom black well plate for measuring LacZ activity as a transfection efficiency control and followed by addition of 20 ul/well of Beta-Glo substrate (Promega, Southampton, UK) and cultivation at room temperature for at least 20 min. Subsequently, 30 μl/well of Bright-Glo luciferase substrate (Promega, Southampton, UK) was added to the original plate and assess immediately for luminescence activity. The luminescence produced from either reaction was read using a Flurostar Optima plate reader (BMG tabtech, Bucks, UK). The resulting luciferase activity was then normalized against lacZ activity obtained from Beta-glo measurement and is displayed as relative light units (R.t.U).

Boyden Chamber Migration Assay

The migratory or invasive capacity of human mammary cancer cell lines was assessed by the Boyden chamber assay. Cells were seeded in low serum media in a chamber with porous membrane (transparent polyethylene terephthalate (PET) membranes with 8 μm pores) as a solid support for motility assays or with a porous membrane coated with Matrigel Basement Membrane Matrix (BD BioCoat Growth factor reduced invasion chambers) for invasion assay. The cell insert was placed into a well with complete growth media, therefore cells are stimulated by a serum gradient to migrate or invade across the membrane through pores.

Total of 750 μl of complete growth media containing 10% of serum was added to appropriate wells of a 24 well cell culture insert companion plate (BD Biosciences, Oxford, UK). A cell culture insert (BD Biosciences, Oxford, UK) was then carefully placed into each well of the insert companion plate using tweezers. Cells were is detached from tissue culture plates using 0.25% w/v Trypsin/EDTA (Invitrogen) and centrifuged at 13000 rpm for 5 min. Cells were washed twice in serum free media by resuspension and centrifugation. The appropriate number of cells ($2 \times 10^5$ cells/ml for MDA-MB-231 cells) was resuspended in normal growth media containing only 0.1% serum. 350 μl of the cell suspension was added to the appropriate upper chambers of the cell culture inserts and plates were incubated for 24 hrs at 37° C. and 5% $CO_2$.

After incubation, cells on membranes were fixed by replacing the media in the top and bottom sections of the chamber with 70% ice-cold ethanol (Fisher Scientific). Plates were incubated at −20° C. for at least an hour. After fixation, inserts were immersed in a tap water using tweezers to ensure all ethanol was removed. A moistened cotton wool bud was then used to mechanically remove all cells fixed on the upper side of the membranes. Cells were stained by individually immersing the inserts into filtered Harris' Haematoxylin (Sigma, Dorset, UK) for 1 min. Following this, inserts were washed in a beaker of tap water to remove the dye and immersed in 0.5% filtered Eosin (Sigma, Dorset, UK) for 2 min. Stained inserts were then washed again in a tap water.

Glycerol Gelatin (Sigma, Dorset, UK) was heated in a beaker of boiling water and once liquefied, a drop was placed onto an appropriately labelled microscope slide (R. A. Lamb, Loughborough, UK). Membranes were cut out of the insert and transferred onto the corresponding slide with tweezers. Glycerol Gelatin was added to the top of the membranes and a cover slip was placed on the slide under firm pressure. Mounted slides were left to air dry before being analysed.

Protein Analysis

Protein Extraction From Cells

Proteins were extracted from cells in order to be analyzed by ELISA assay. The media from tissue culture flask was removed and cells were rinsed with ice cold PBS (Sigma, Dorset, UK). Appropriate volume of PBS (5 ml for T25, 10 ml for T80) was added into the flask and cells were removed with a cell scraper (Nunc, Leics, UK). The cell suspension was then transferred to 15 ml tubes and centrifuged at 11000 rpm for 5 min at room temperature. Resulting pellet was used for protein extraction immediately or stored at −20° C. prior use.

Non-denatured protein extract was prepared using non-denaturing lysis buffer (Table 1) and used to analyze protein-protein interaction.

TABLE 1

Composition of buffers for whole cell protein extraction

| RIPA buffer pH 7.4 | Non-denaturing buffer |
|---|---|
| 50 mM Tris pH 8 (Sigma) | 20 mM Tris pH 7.5 (Sigma) |
| 150 mM sodium chloride (Sigma) | 150 mM sodium chloride (Sigma) |
| 1% v/v Nonidet-P40 (Roche) | 1% v/v Nonidet-P40 (Roche) |
| 0.1% w/v sodium dodecyl sulphate (SDS, Sigma) | 1 mM EDTA pH 8.0 (Fischer Scientific) |
| 0.5% w/v sodium deoxycholate (Sigma) | 1 mM EGTA pH 8.0 (Fluka Biochemika) |

Complete mini protease inhibitor tablets (Roche, Welwyn Garden City, UK), 10 mM sodium fluoride (Fluka Biochemika), 1 mM sodium pyrophospate and 1 mM sodium orthovanadate (Sigma, Dorset, UK) were added to the buffer prior use. Cell pellets were resuspended in appropriate volume of non-denaturing buffer (50-200 µl) and cultivated on ice 5 min. Cell suspensions were transferred to microcentrifuge tubes and sonicated on ice (3 times 5 s) and centrifuged at 10000 rpm for 10 min at 4° C. The resultant supernatant was used immediately or stored at −20° C. until required.

ELISA Assay

In our case, ELISA assay was used to detect either the amount of Flag-Bcl-3 protein alone or Flag-Bcl-3 in complex with p50, using indirect or sandwich ELISA respectively.

For Indirect and sandwich ELISA assay, Non-denaturing cell lysate (above) was diluted with TBS/T [tris buffer saline (TBS, Calbiochem, Merck) supplemented with 0.5% v/v Tween (Sigma, Dorset, UK)] to a concentration of 0.5-1 µg/µl and 100 µl was added onto ANTI-Flag coated flat bottom ELISA plates (Sigma, Dorset, UK). Samples were added in triplicates, while TBS/T was used as a negative control. The plate was cultivated at 37° C. for an hour followed by 3×200 µl washes with TBS/T. Primary antibodies, either Bcl-3 (Santa Cruz Biotech) for indirect ELISA and p50 for sandwich ELISA (Abcam) were added in known volumes (125 µl) and concentrations to each well, cultivated covered from light for an hour at room temperature. Another three 200 µl washes with TBS/T were performed before cultivation with alkaline phospatase (AP) conjugated secondary antibody. Meanwhile, para-nitrophenylphosphate solution (pNPP, Santa Cruz Biotechnology, California, USA) was prepared according to manufacturer's instructions (5 mg of pNPP disodium salt in 5 ml of pNPP substrate buffer). The solution was mixed well and covered from light prior to use. pNPP is a substrate of choice for use with alkaline phosphatase and produces a soluble end product that is yellow in colour. Therefore colour changes can be measured and represent the amount of AP present. After cultivation with secondary antibody, the wells were washed 3×200 µl. TBS/T, pNPP solution was added (50 µl/well) and cultivated for an hour covered from light at room temperature. The reaction was stopped by addition of 3N NaOH (20 µl/well) and the colorimetric changes were measured at 405 nm using a plate reader.

Statistical Analysis

The Student's T-test was used to determine statistical differences between normally distributed data sets and between data sets with sample sizes of n=3. This test was performed using Excel 2008 software.

Example 4

Characterization of Example Compound 1a

We established that the solubility of Compound 1a in most commonly used solvents is very low (Table 2) which represents an issue for biological evaluation. Therefore a hydrochloric salt of Compound 1a was synthesised and the solubility was analysed. The obtained salt had improved solubility in water and methanol (Table 2), however it was not soluble (<0.1 g/100 ml) in Phosphate Buffered Saline (PBS). PBS is a water-based salt solution containing sodium chloride, sodium phosphate, potassium chloride and potassium phosphate, while the buffer's phosphate groups help to maintain a constant pH. PBS is non-toxic and is commonly used as an isotonic is buffered solution for cell-based assays and animal studies.

TABLE 2

Solubility of the lead compound in organic solvents

| | Solubility (g/100 ml) | |
|---|---|---|
| Solvent | Compound 1a | Compound 1a hydrochloride salt |
| Water | <0.01 | 0.95 |
| Methanol | 0.20 | 0.59 |
| Ethanol | 0.09 | 0.19 |
| DMSO | 3.71 | <0.01 |
| Ethyl acetate | 0.34 | 0.02 |
| Dichloromethane | 2.91 | 0.90 |
| Diethyl ether | 0.09 | <0.01 |

Example 5

Cell Toxicity of Compound 1a In Vitro

The toxicity of Compound 1a was evaluated in vitro using human breast cancer cell lines. To compare the toxicity in tumorigenic as well as in non-tumorigenic breast cancer cells, we selected MCF-10A as a non-tumorigenic human breast cancer cell line and MDA-MB-231 and SKBR3 as cell models of tumorigenic human breast cancer cell line.

MCF-10 cells were derived from a mammary tissue from a 36-year-old woman in a good health and the immortalized MCF-10A line can grow in culture and has a stable, near-diploid karyotype with modest genetic modifications typical of culture-adapted breast epithelial cells, including loss of p16 locus. The cells express normal p53 and they do not grow in immuno-compromised mice.

Compound 1a was dissolved in DMSO and diluted in media in a highest concentration of 1mM ($10^{-3}$M). Cell toxicity was evaluated using the Cell Titre Blue viability assay over a range of molarities for 24 hrs. The effect of Compound 1a on cell viability was always normalised against DMSO control and the dose-response curve was generated using GraphPad software (FIG. 1).

$IC_{50}$ values could not be established in any of the cell lines, as even the highest concentration did not cause a 50% decrease in cell viability. We could, however, see a difference in cell toxicity between non-tumorigenic and tumorigenic cell lines. At the highest concentration of 1 mM, the viability in MCF-10A cell line was 96%, 72% in MDA-MB-231 and 57% in SKBR3 compared to DMSO control (100%). This low toxicity was expected of a specific inhibitor of Bcl-3 as previous studies had shown that genetic inhibition of Bcl-3 had only a modest effect on cell viability of cancer cell lines in vitro and little or no effect on non-tumourgenic lines (11).

The $IC_{50}$ was calculated using GraphPad software by extrapolating the dose-response curve, giving $IC_{50}$ values of 14.9 mM for MCF-10A, 2.70 mM for MDA-MB-231 and 1.37 mM for SKBR3.

Example 6

Establishing Biological Effects of Compound 1a In Vitro

A. Establishing Effect on Protein Binding by Indirect Sandwich ELISA

Figure 2:
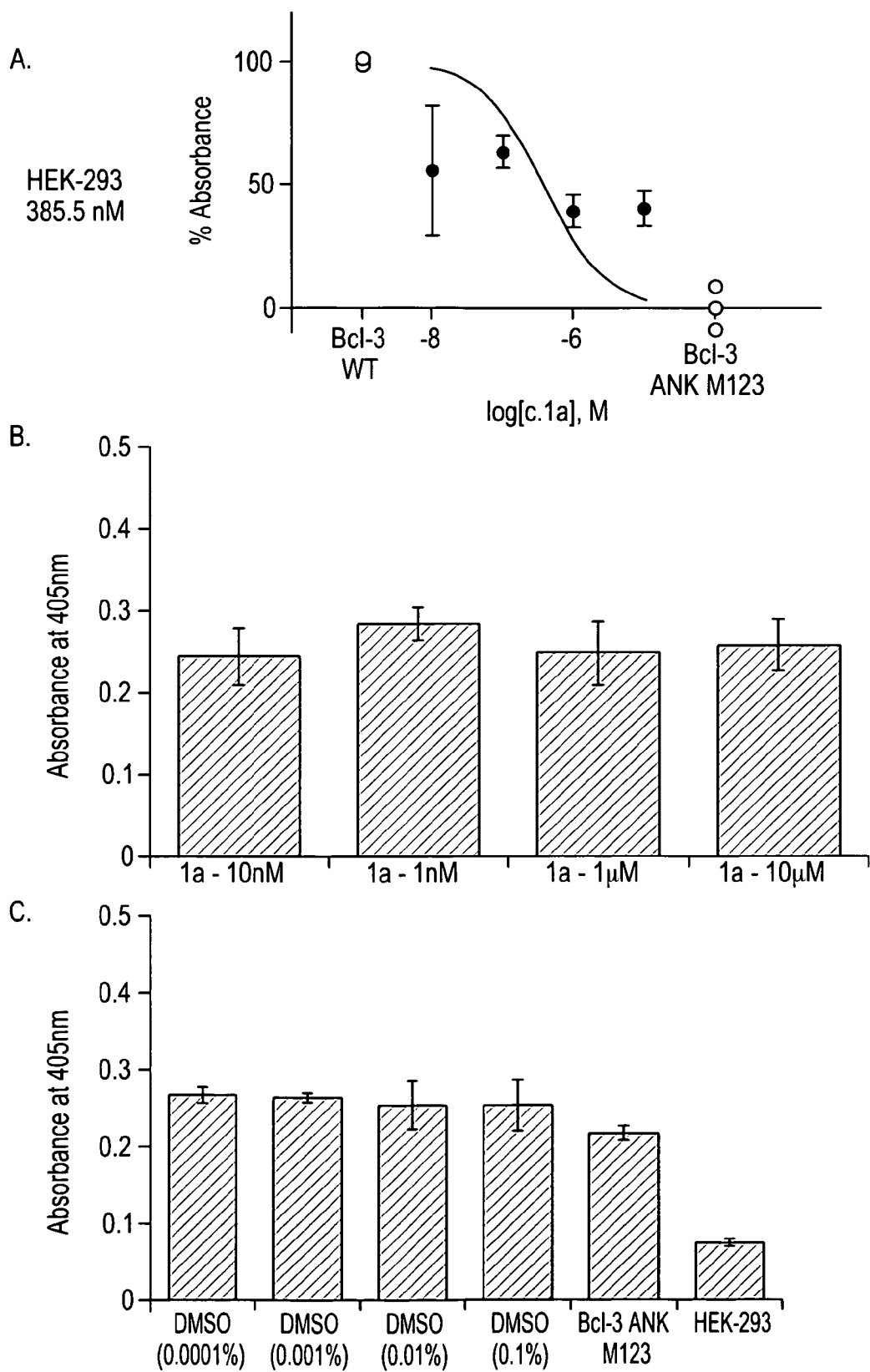
FIG. 2. Establishing the ability of Compound 1a to inhibit Bcl3 binding to its cognate protein partner NFKB1 (p50) by Indirect Sandwich ELISA assay. HEK-293 cells over-expressing FLAG-tagged Bcl-3 were cultivated with compound 1a or DMSO in a range of molarities in normal adherent growth conditions for 24 hrs. Cell lysates were prepared under non-denaturing conditions. [A] Indirect sandwich ELISA assay was performed on anti-FLAG coated ELISA plates using p50 antibody. Absorbance was measured at 405 nm and normalised to that of DMSO control. Error bars represent ±SEM of three independent wells. The dose response curve was generated using GraphPad software. The $IC_{50}$ for Compound 1a is shown inset. [B] and [C] Indirect ELISA assay was performed on FLAG coated ELISA plates using Bcl-3 antibody. Absorbance was measured at 405 nm. Error bars represent ±SEM of three independent wells.

HEK-293 cells overexpressing Bcl-3 were cultivated with Compound 1a over a range of molarities for 24 hrs before cell lysates were obtained under non-denaturing conditions. The dose response curve was generated using GraphPad software (FIG. 2A). The determined $IC_{50}$ was 385.5 nM. Indirect ELISA assay was performed using Bcl-3 antibody to show an equal loading across samples treated with compound 1a (FIG. 2B) and controls (FIG. 2C).

B. Establishing the Effect on Intra-Cellular NF-κB Activity

Figure 3:
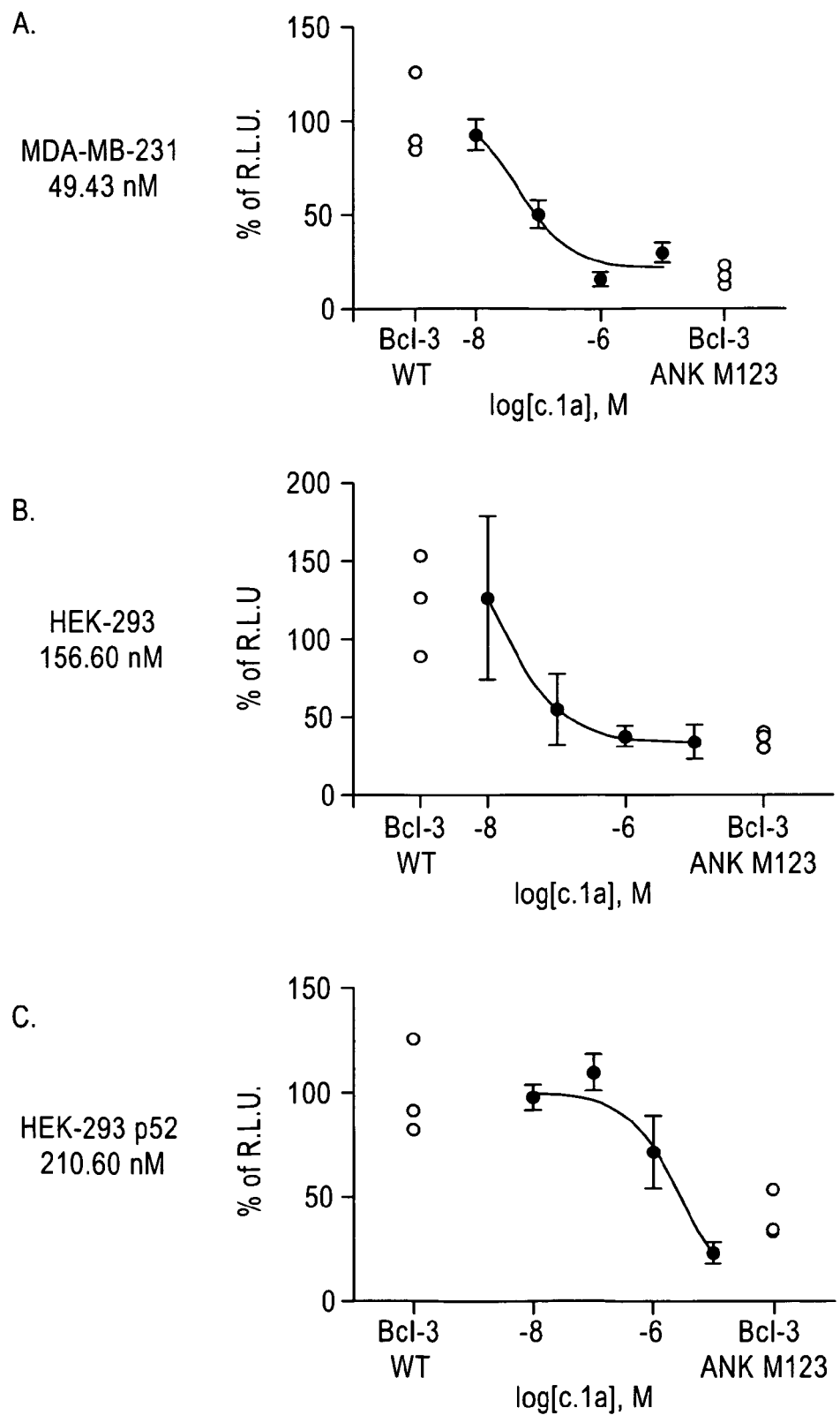
FIG. 3. Establishing the ability of Compound 1a to inhibit NF-κB signalling by NF-κB promoter-reporter (luciferase) assay. MDA-MB-231 overexpressing Bcl-3 [A], HEK-293 cells overexpressing Bcl-3 [B] and HEK-293 overexpressing Bcl-3 and p52 [C] were cultivated with Compound 1a or DMSO control in a range of molarities for 24hrs before being transfected with NF-κB luciferase reporter for 48 hrs together with controls. NF-κB activity is represented as a % of DMSO control. Error bars represent ±SEM of three independent experiments. The dose response curve was generated using GraphPad software. $IC_{50}$s for each cell line are shown inset.

The effect of Compound 1a on NF-κB activity was determined by NF-κB luciferase assay in MDA-MB-231 and HEK-293 cells overexpressing Bcl-3 and HEK-293 cells overexpressing p52. Cells were cultivated with Compound 1a over a range of molarities for 24 hrs before being transfected with NF-κB luciferase reporter plasmid for 48 hrs and analysed for NF-κB activity. The dose response curve was generated to using GraphPad software (FIG. 3). The determined $IC_{50}$ in MDA-MB-231 cells was 49.43 nM, 159.6 nM HEK-293 cells and 210.6 nM in HEK-293 p52 overexpressing cells.

C. Establishing the Effect of Compound 1a on Cell Motility

Figure 4:
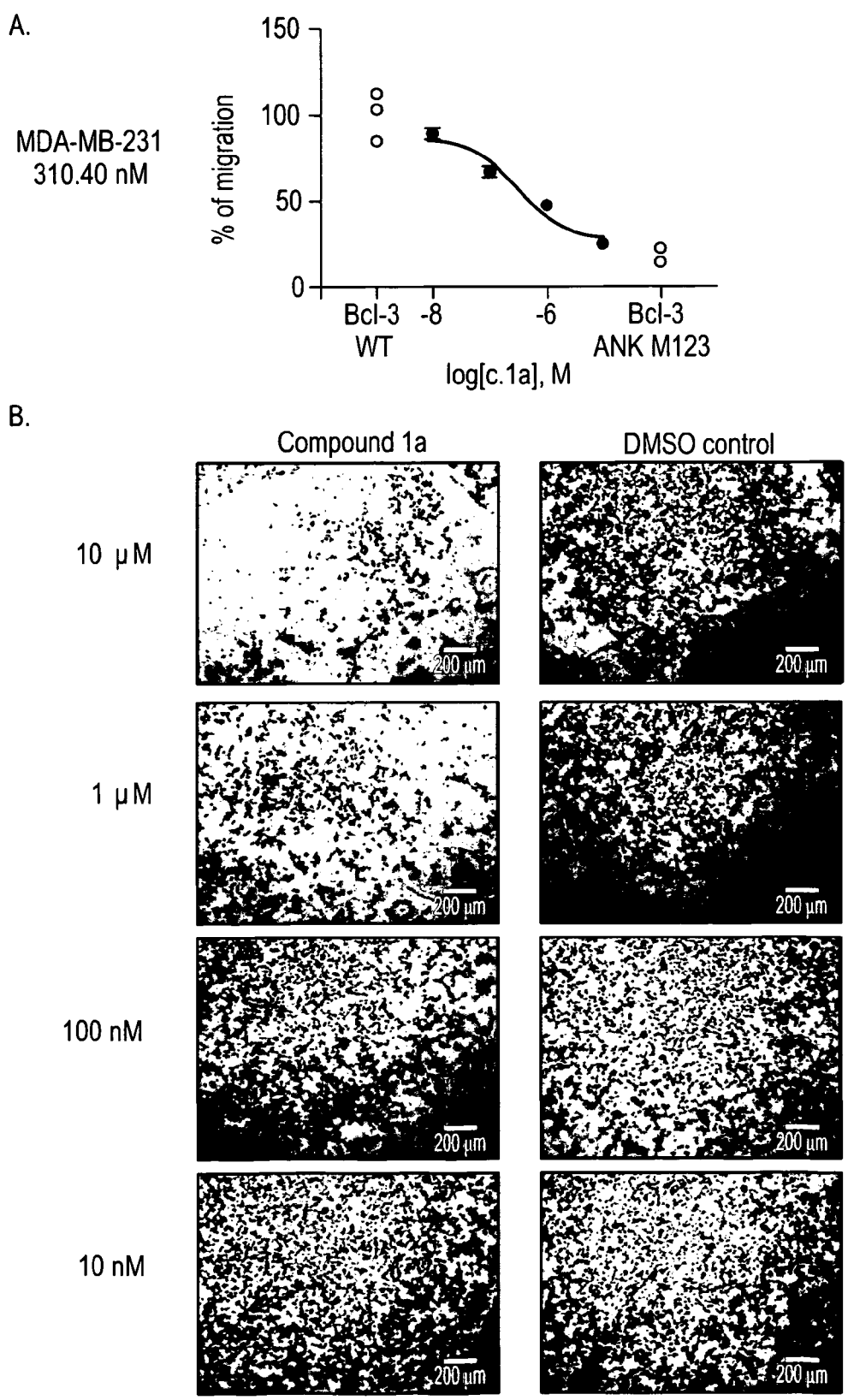
FIG. 4. Establishing the effect of Compound 1a on cell motility by Boyden Chamber assay. [A] MDA-MB-231 cells overexpressing Bcl-3 were cultivated with compound 1a (10 μM, 1 μM, 100 nM, 10 nM) or DMSO in corresponding concentration in normal adherent growth conditions for 24 hrs before being seeded onto Boyden motility chambers for 24 hrs in parallel with cells overexpressing the Bcl-3 binding mutant ANK M123. Migrated cells were counted from three fields of view of each of three replicate Boyden chambers. Error bars represent ±SEM. The dose response curve was generated using GraphPad software. The $IC_{50}$ is shown inset. [B] Representative images of migrated cells for MDA-MB-231 cells overexpressing Bcl-3 and treated with either compound 1a or DMSO. Scale bars represent 200 μm.

It was previously determined that Compound 1a significantly suppressed migration ability in MDA-MB-231 cells at 10 µM. We therefore generated a dose response curve to determine an $IC_{50}$ in this assay. MDA-MB-231 cells overexpressing Bcl-3 were cultivated with Compound 1a and DMSO control over a range of molarities for 24 hrs before being seeded onto Boyden migration chambers. The constant number of live cells present during this assay across samples was monitored by cell count. The dose response curve was generated using GraphPad software (FIG. 4). The determined $IC_{50}$ was 310.4 nM.

Example 7

Biological Evaluation of Analogues From Series 1-3

A. Cell Toxicity

Figure 5:
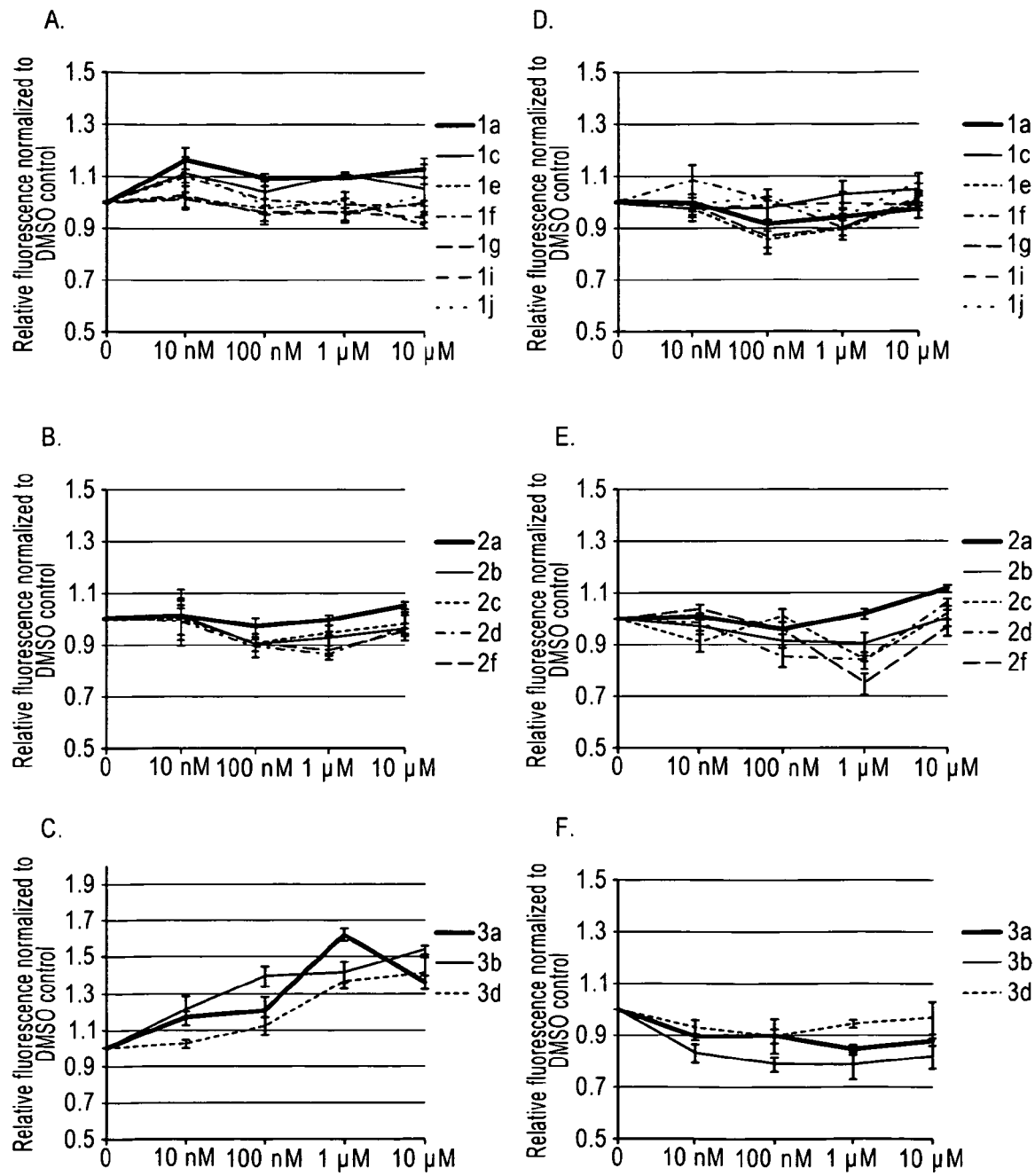
FIG. 5. Cell toxicity of series 3 compounds. MDA-MB-231 cells [A to C] and HEK-293 cells [D to F] were cultivated with compounds from series 1, 2 or 3 (10 nM, 100 nM, 1 μM and 10 μM) in adherent growth conditions. Cell viability was determined after 24 hrs by the Cell Titre Blue viability assay and resulting fluorescence was normalised against that of respective cells treated with DMSO under the same conditions. Data represent average of six wells and error bars represent ±SEM.

Selected compounds were dissolved in DMSO and diluted to a highest concentration of 10 µM (0.1% DMSO). In all assays, a DMSO control was always used. Selected compounds were tested for cell toxicity in HEK-293 and MDA-MB-231 cells before being used in cell-based assays. Cell toxicity was evaluated using the Cell Titre Blue viability assay over a range of molarities for 24 hrs Results for mono-substituted compounds 1a, 1c, 1e, 1f, 1g, 1i, 1j, 2a, 2b, 2c, 2d, 2f, 3a, 3b and 3d are shown in FIG. 5. Compounds were well tolerated in both cell lines and cell viability was above 70% even at 10 µM concentration.

Figure 11:
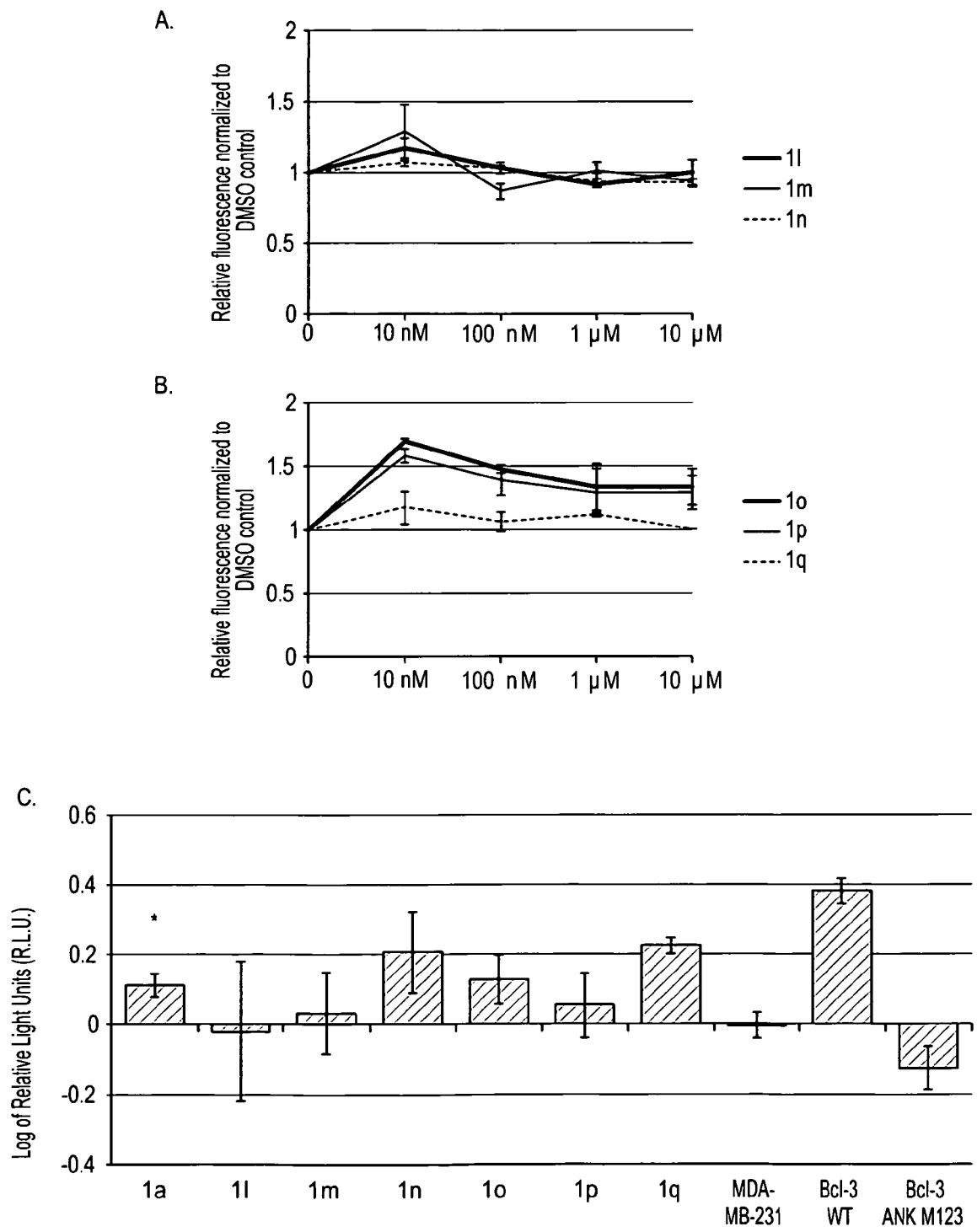
FIG. 11. Biological evaluation of di- and tri-substituted analogues [A] and [B]. MDA-MB-231 cells were cultivated with di- and tri-substituted compounds from series 1 (1l-1q) over a range of molarities in adherent growth conditions. Cell viability was determined after 24 hrs by the Cell Titre Blue viability assay and resulting fluorescence was normalised against that of respective cells treated with DMSO under the same conditions. Data represent average of six wells and error bars represent ±SEM. [C] MDA-MB-231 cells overexpressing Bcl-3 were cultivated with compounds from series 1 (1l-1q) at 1 μM concentration or DMSO control for 24 hrs before being transfected with NF-κB luciferase reporter for 48 hrs together with controls. NF-κB activity is plotted on a log scale as relative light units and normalised to the NF-κB activity of MDA-MB-231 cells. Error bars represent ±SEM of three independent transfections. (T-test, *=p<0.05 as compared to MDA-MB-231).

Results for di- and tri-substituted compounds 1l, 1m, 1n, 1o, 1p and 1q are shown in FIGS. 11A & B. Compounds were well tolerated in both cell lines and cell viability was above 90% even at 10 µM concentration.

B. NF-κB Assay

The effect of selected analogues on NF-κB activity was determined by NF-KB luciferase assay in MDA-MB-231 cells. MDA-MB-231 Bcl-3 over-expressing cells were cultivated with compounds from series 1-3 at 1 µM concentration for 24 hrs before being transfected with NF-κB luciferase reporter plasmid for 48 hrs together with controls and analysed for NF-κB activity.

Figure 6:
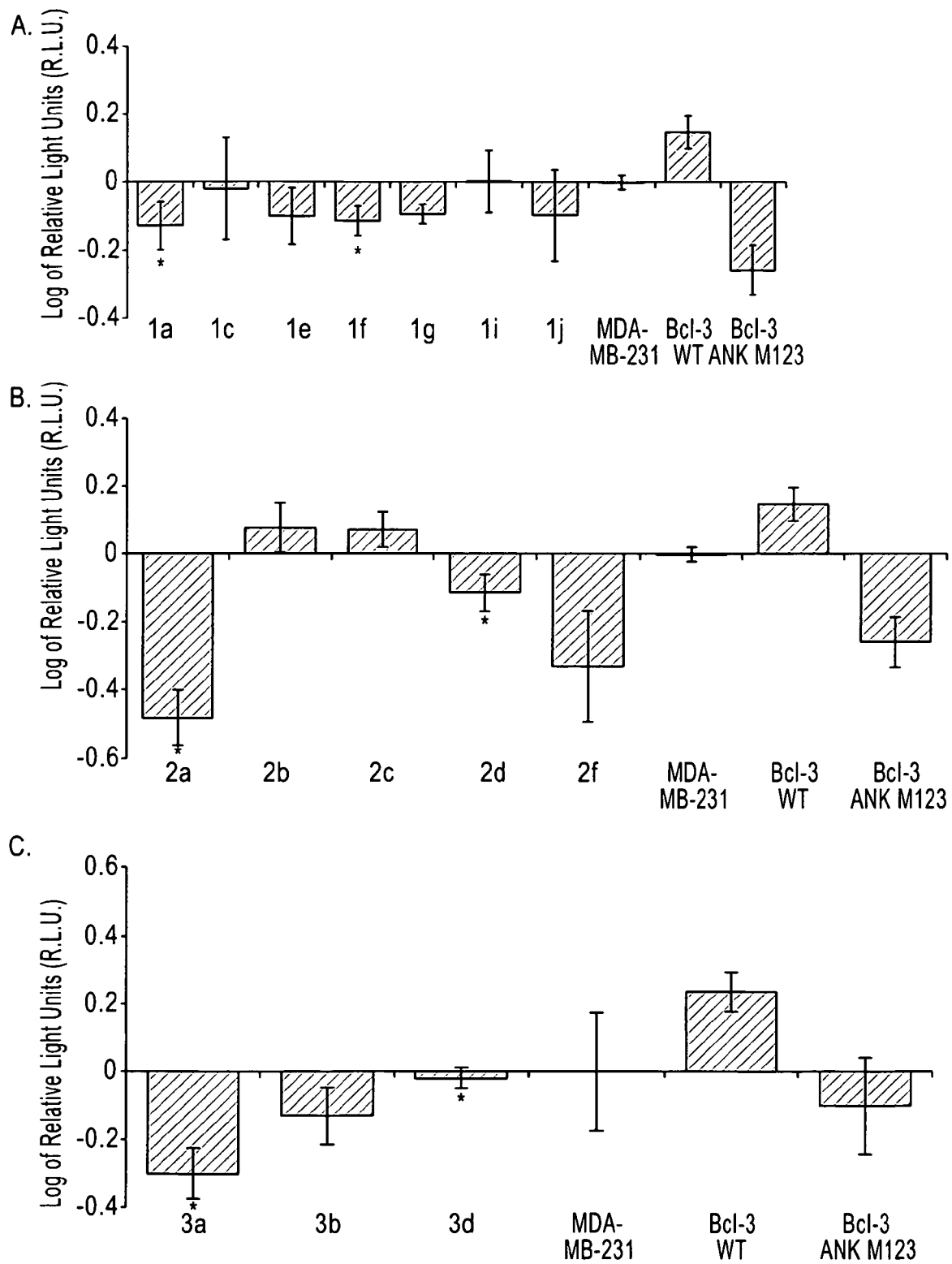
FIG. 6. NF-κB assay in MDA-MB-231 cells with series 1 to 3 compounds. MDA-MB-231 cells overexpressing Bcl-3 were cultivated with compounds from series 1 [A], 2 [B] and 3 [C] at 1 μM concentration or DMSO control for 24 hrs before being transfected with NF-κB luciferase reporter for 48 hrs together with controls. NF-κB activity is plotted on a log scale as relative light units and normalised to the NF-κB activity of MDA-MB-231 cells not overexpressing Bcl-3. Error bars represent ±SEM of three independent transfections. (T-test, *=p<0.05 as compared to MDA-MB-231 Bcl-3 WT).

Results for mono-substituted compounds 1a, 1c, 1e, 1f, 1g, 1i, 1j, 2a, 2b, 2c, 2d, 2f, 3a, 3b and 3d are shown in FIG. 6).

is It can be seen that the NF-κB activity of the mono-substituted analogues from series 1 was comparable to that of Compound 1a, with a significant decrease of in NF-KB activity observed for Compound 1a and the analogue 1f as compared to DMSO control.

From series 2 analogue 2a and 2d significantly decreased NF-κB activity as compared to Bcl-3 WT DMSO control. Analogue 2a showed comparable activity with Compound 1a with other analogues having lesser activity.

From series 3 analogue 3a had comparable effect on NF-κB activity with Compound 1a. Analogue 3c also showed significant decrease in NF-κB activity as compared to DMSO control, however not to the same level as Compound 1a.

Figure 7:
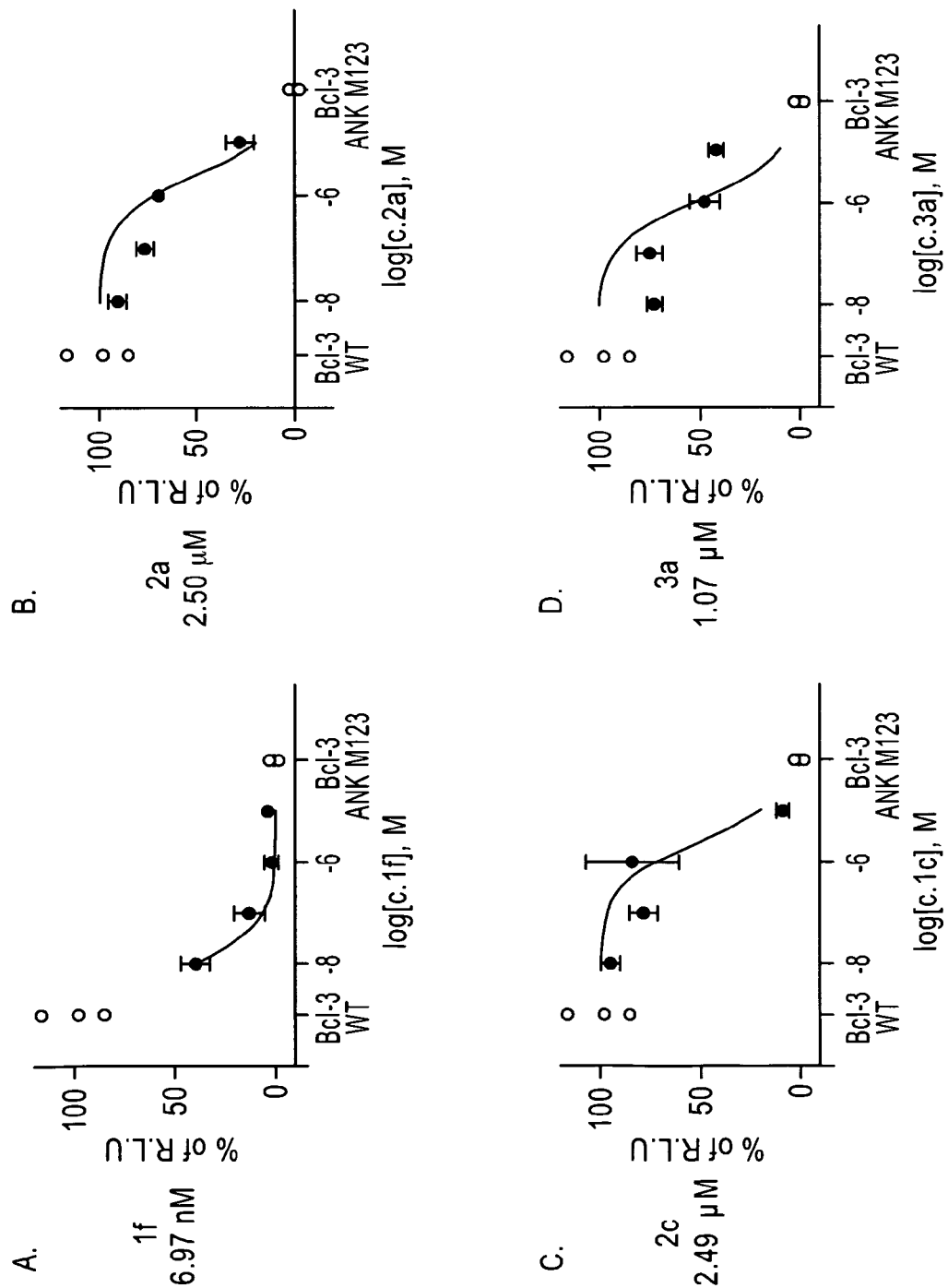
FIG. 7. Establishing the effect of selected analogues on NF-κB signalling by luciferase-reporter assay in MDA-MB-231 cells. MDA-MB-231 cells overexpressing Bcl-3 were cultivated with analogues 1f [A], 2a [B], 2c [C] and 3a [D] or DMSO control in a range of molarities for 24 hrs before being transfected with NF-κB luciferase reporter for 48 hrs together with controls. NF-κB activity is represented as a % of DMSO control. Error bars represent ±SEM of three independent transfections. The dose response curve was generated using GraphPad software. The $IC_{50}$ for each of the analogues are shown on the left of each graph.
Figure 8:
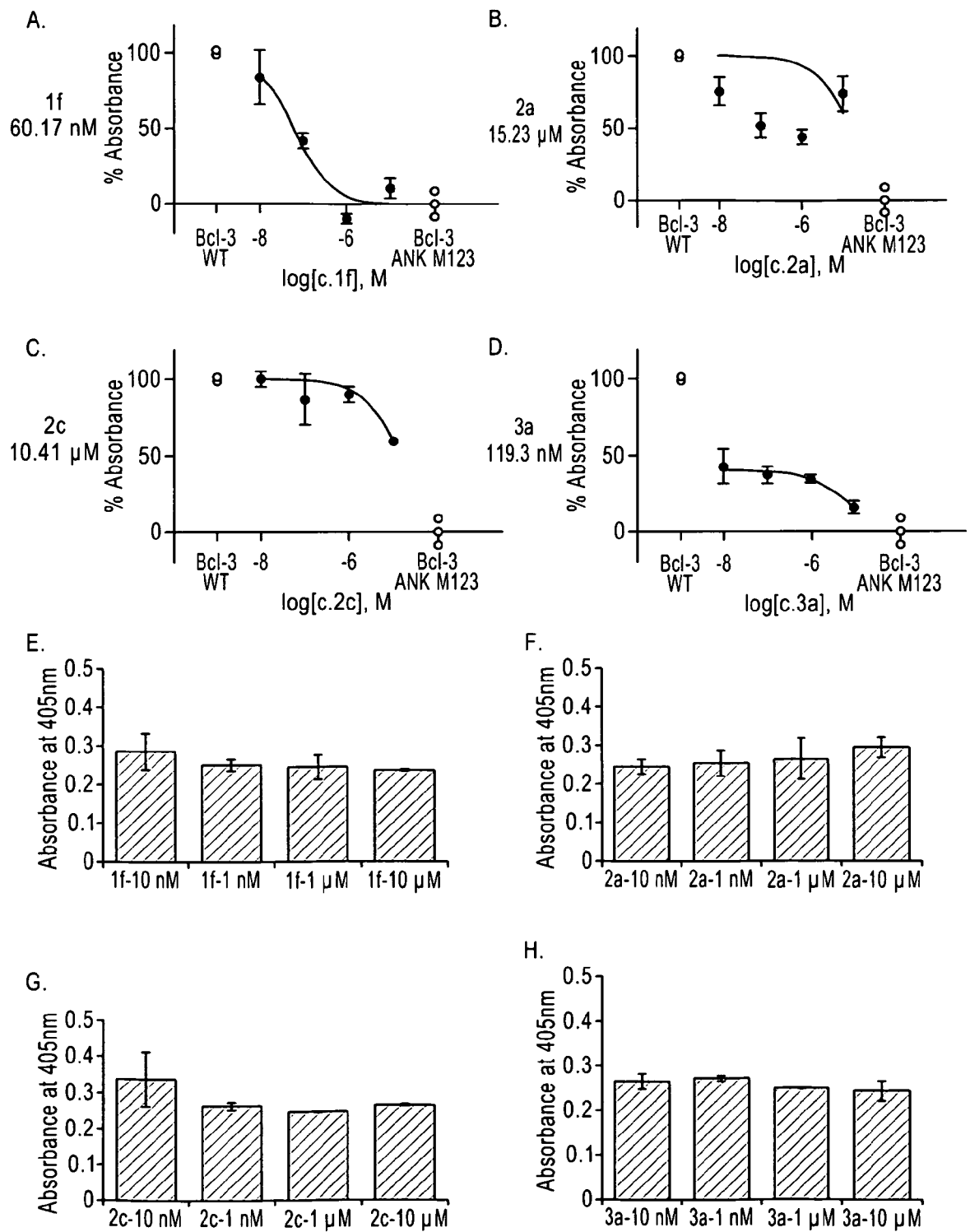
FIG. 8. Establishing the effect of selected analogues on Bcl-3 binding to p50 by Indirect Sandwich ELISA Assay. HEK-293 cells overexpressing FLAG-tagged Bcl-3 were cultivated with compound 1f [A], 2a [B], 2c [C] and 3a [D] or DMSO in a range of molarities in normal adherent growth conditions for 24 hrs. Cell lysates were prepared under non-denaturing conditions. Indirect sandwich ELISA assay was performed on FLAG coated ELISA plates using p50 antibody. Absorbance was measured at 405 nm and normalised to that of DMSO control. Error bars represent ±SEM of three independent wells. The dose response curve was generated using GraphPad software. $IC_{50}$s are shown for each analogue to the left of each graph. [E-H]. Indirect ELISA assay was performed on FLAG coated ELISA plates using Bcl-3 antibody. Absorbance was measured at 405 nm. Error bars represent ±SEM of three independent wells.

Based on the results for the series of analogues, we have established dose response curve for selected analogues from series 1 (10, from series 2 (2a and 2c) and from series 3 (3a) over a range of molarities. MDA-MB-231 Bcl-3 WT cells were cultivated with selected compounds from series 1-3 over a range of molarities for 24 hrs before being transfected with NF-κB luciferase reporter plasmid for 48 hrs together with controls and analysed for NF-κB activity (FIG. 7). We observed an improvement in the determined $IC_{50}$ for analogue 1f (6.97 nM). Other analogues showed decreased ability to suppress NF-κB activity compared with Compound 1a. The determined $IC_{50}$ for analogue 2a was 2.50 µM, 2.49 µM for analogue 2c and 1.07 µM for analogue 3a (see Table 3).

Figure 12:
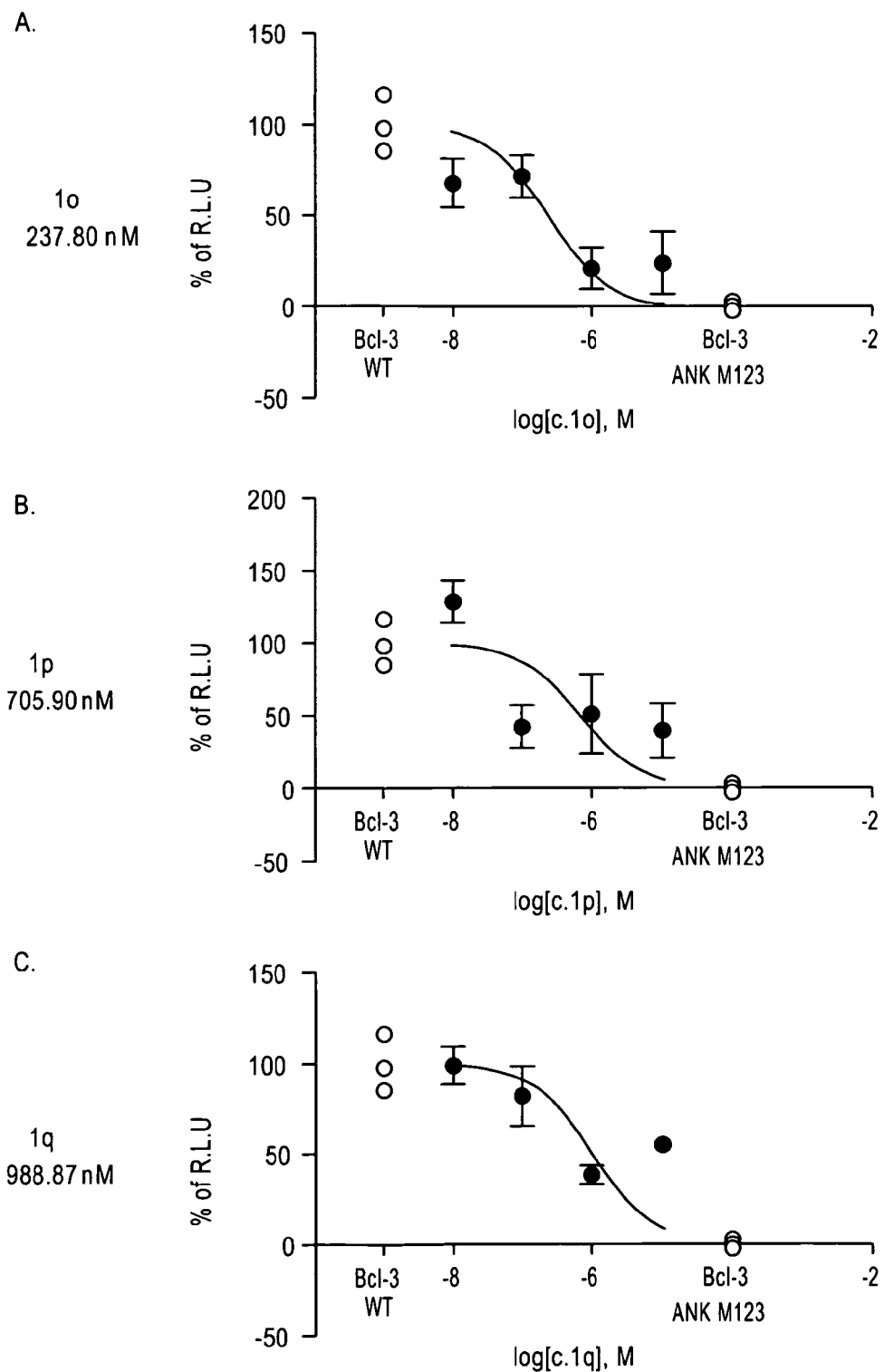
FIG. 12. Establishing the effect of selected di- and tri-substituted analogues on NF-κB activity by luciferase-reporter assay in MDA-MB-231 cells. MDA-MB-231 cells overexpressing Bcl-3 were cultivated with analogues 10 [A], 1p [B], 1q [c] or DMSO control at a range of molarities for 24 hrs before being transfected with NF-κB luciferase reporter for 48 hrs together with controls. NF-κB activity is represented as a % of DMSO control. Error bars represent ±SEM of three independent transfections. The dose response curve was generated using GraphPad software. $IC_{50}$s are shown to the left of each graph.

Results for di- and tri-substituted compounds 1l, 1m, 1n, 1o, 1p and 1q are shown in FIG. 11C (compared with Compound 1a) and FIG. 12 as well as in Table 3.

Compound 1a showed the most potent suppression of NF-κB activity as compared to Bcl-3 WT overexpressing MDA-MB-231 cells (FIG. 11C).

$IC_{50}$ values were established for three selected analogues (1o-q). All three tested analogues showed decreased ability to suppress NF-κB activity than Compound 1a. The determined $IC_{50}$ for analogue 1o was 237.80 nM, 705.90 nM for analogue 1p and 988.87 nM for analogue 1q (FIG. 12; Table 3).

TABLE 3

Comparison of IC$_{50}$ values for test compounds

| Analogue | ELISA assay (μM) | NF-κB assay (μM) | Cell motility assay (μM) |
|---|---|---|---|
| 1a | 0.3855 | 0.04543 | 0.3104 |
| 1f | 0.0617 | 0.00697 | 0.02893 |
| 2a | 15.23 | 2.5 | 1.33 |
| 2c | 10.41 | 2.49 | 3.65 |
| 3a | 0.01195 | 1.07 | 0.90 |
| 1o |  | 0.2378 |  |
| 1p |  | 0.7059 |  |
| 1q |  | 0.98887 |  |

C. Indirect Sandwich ELISA Assay

The ability to disrupt Bcl-3-p50 binding was determined by Indirect Sandwich ELISA assay for selected analogues (1f, 2a, 2c, 3a).

HEK-293 Bcl-3 WT cells were cultivated with selected compounds over a range of molarities for 24 hrs before cell lysates were obtained under non-denaturing conditions. The dose response curve for selected analogues was generated using GraphPad software (FIG. 8A-D). We observed improved IC50 as compared to Compound 1a for analogues 1f and 3a, with IC50 values 60.17 nM and 119.3 nM respectively. The IC50 could not be established for analogues from series 2, 2a and 2c, and was calculated from the dose response curve using GraphPad software with IC$_{50}$ of 15.23 μM for analogue 2a and 10.41 μM for analogue 2c.

Indirect ELISA assay was performed using Bcl-3 antibody to show an equal loading across samples treated with compounds 1f, 2a, 2c, and 3a (FIG. 8E-H).

D. Cell Motility Assay

Figure 9:
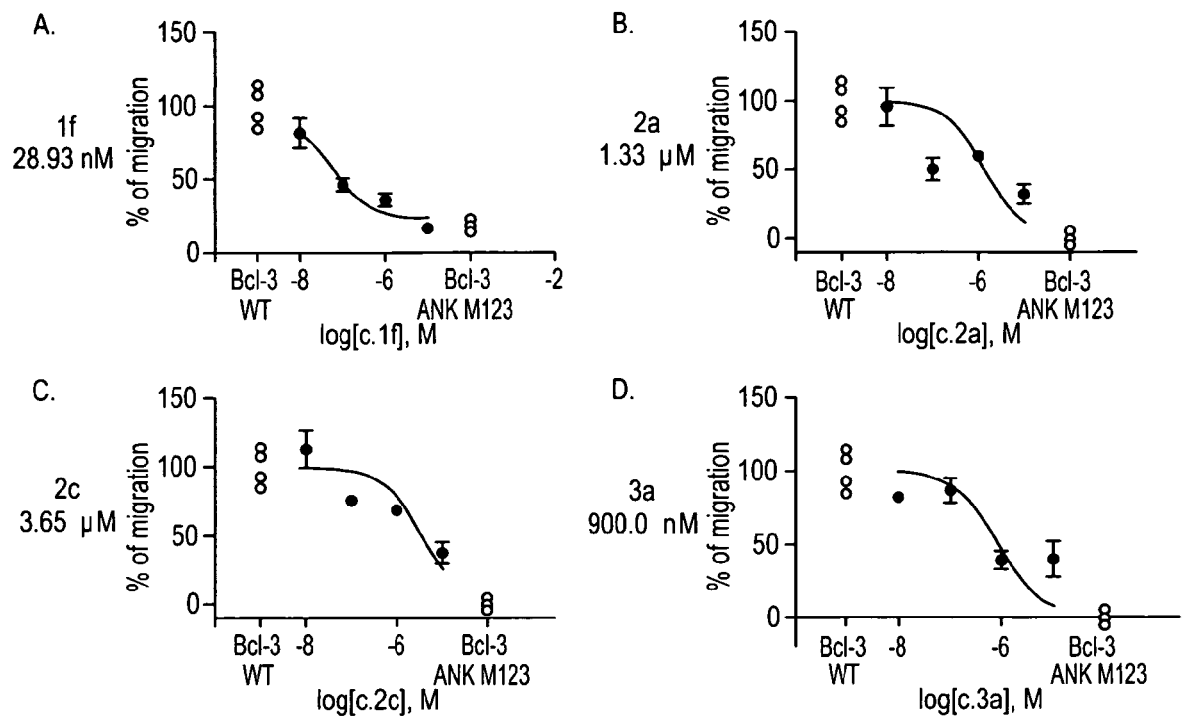
FIG. 9. Establishing $IC_{50}$ the effect of selected analogues on cell motility by Boyden chamber assay. MDA-MB-231 cells overexpressing Bcl-3 were cultivated with compounds 1f [A], 2a [B], 2c [C] and 3a [D] or DMSO in a range of molarities in normal adherent growth conditions for 24 hrs before being seeded onto Boyden motility chambers for 24 hrs in parallel with MDA-MB-231 cells expressing the Bcl-3 binding mutant ANK M123. Migrated cells were counted from three fields of view of each of three replicate Boyden chambers. Error bars represent ±SEM. The dose response curve was generated using GraphPad software. The $IC_{50}$s for each analogue are shown to the left of each graph.

As shown in Example 6, Compound 1a caused a significant decrease in cell motility with an IC$_{50}$ value of 310.4 nM. Therefore we wanted to establish whether designed analogues have similar or improved ability to suppress cell migration. MDA-MB-231 Bcl-3 over-expressing cells were cultivated with selected analogues (1f, 2a, 2c, 3a) and DMSO control over a range of molarities for 24 hrs before being seeded onto the Boyden motility chambers. Migrated cells were visualised and counted after 24 hrs. The dose response curves were generated using GraphPad software (FIG. 9). The constant number of live cells present during this assay across samples was monitored by cell count.

Consistent with results from NF-κB assay and Indirect Sandwich ELISA assay, the analogue 1f showed an improved ability to suppress cell migration, with IC50 value of 28.93 nM. Interestingly, the cell migration was suppressed below 50% even at 10 nM concentration. Other analogues showed decreased ability to suppress cell motility than Compound 1a. The determined IC50 for analogue 2a was 1.33 μM, 3.65 μM for analogue 2c and 900 nM for analogue 3a.

F. Establishing EC$_{50}$ of Analogue 1f

The activity of the analogue 1f was improved as compared to Compound 1a; therefore next we determined the toxicity of this analogue in MDA-MB-231 cell line.

Figure 10:
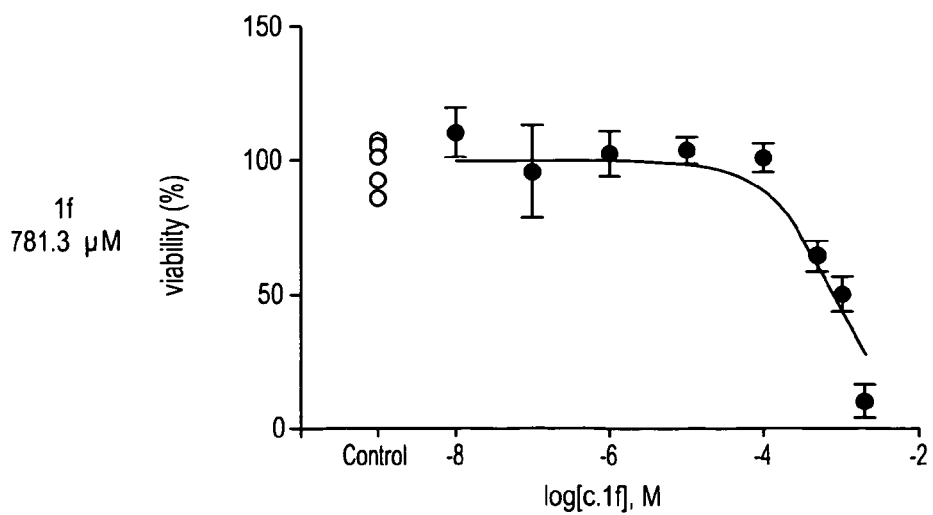
FIG. 10. Establishing the effect of analogue 1f on cell viability. MDA-MB-231 cells were cultivated with the analogue 1f over a range of molarities in adherent growth conditions. Cell viability was determined after 24 hrs by the Cell Titre Blue viability assay and resulting fluorescence was normalised against fluorescence of control cells treated with DMSO in relevant concentration. Data represent average of six wells and error bars represent ±SEM. Dose response curves were generated using GraphPad software. The $IC_{50}$ is shown to the left of the graph.

Compound 1a was dissolved in DMSO and diluted in media to a highest concentration of 2 mM. Cell toxicity was evaluated using the Cell Titre Blue viability assay over a range of molarities for 24 hrs. The effect of Compound 1a on cell viability was always normalised against DMSO control and the dose-response curve was generated using GraphPad software (FIG. 10). The determined EC$_{50}$ for analogue 1f was 781.3 μM.

SUMMARY

We have synthesised 2-[(2-fluorobenzoyl)amino]-N-(2-morpholin-4-ylethyl)benzamide (Compound 1a) and a number of novel analogues of this compound and we have shown that the compounds are inhibitors of Bcl3 since are capable of suppressing Bcl3-NFkB protein interactions and inhibiting NF-κB signalling. This indicates that the compounds will be useful for the treatment of cancer, particularly metastatic cancer.

REFERENCES

1. Biswas, D. K. & Iglehart, J. D. 2006. Linkage Between EGFR Family Receptors and Nuclear Factor Kappa B (NF-κB) Signaling in Breast Cancer. *Journal of cellular physiology*, 209, 645-652.

2. Kim, H., Hawke, N. & Baldwin, A. 2006. NF-κB and IKK as therapeutic targets in cancer. *Cell Death Diff*, 13, 738-747.

3. Au, W. Y., Horsman, D. E., Ohno, H., Klasa, R. J. & Gascoyne, R. D. 2002. Bcl-3/IgH translocation (14; 19) (q32; q13) in Non-Hodgkin's Lymphomas. *Leukemia & Lymphoma*, 43, 813-816.

4. Nishikori, M., Maesako, Y., Ueda, C., Kurata, M., Uchiyama, T. & Ohno, H. 2003. High-level expression of BCL3 differentiates t(2; 5) (p23; q35)-positive anaplastic large cell lymphoma from Hodgkin disease. *Blood*, 101, 2789-2796.

5. Cogswell, P. C., Guttridge, D. C., Funkhouser, W. K. & Baldwin, A. S. 2000. Selective activation of NF-κB subunits in human breast cancer: potential roles for NF-κB 2/p52 and for Bcl-3. *Oncogene*, 19, 1123-1131.

6. Thornburg, N. J., Pathmanathan, R. & Raab-Traub, N. 2003. Activation of Nuclear Factor-κB p50 Homodimer/Bcl-3 Complexes in Nasopharyngeal Carcinoma. *Cancer Res.*, 63, 8293-8301.

7. O'Neil, B., Buzkova, P., Farrah, H., Kashatus, D., Sanoff, H., Goldberg, R., Baldwin, A. & Funkhouser, W. 2007. Expression of nuclear factor-kappaB family proteins in hepatocellular carcinomas. *Oncology*, 72, 97-104.

8. Puwada, S. D., Funkhouser, W. K., Greene, K., Deal, A., Chu, H., Baldwin, A. S., Tepper, J. E. & O'Neil, B. H. 2010. NF-κB and Bcl-3 Activation Are Prognostic in Metastatic Colorectal Cancer. *Clin. Transl. Res.*, 78, 181-188.

9. Cogswell, P. C., Guttridge, D. C., Funkhouser, W. K. & Baldwin, A. S. 2000. Selective activation of NF-κB subunits in human breast cancer: potential roles for NF-κB 2/p52 and for Bcl-3. *Oncogene*, 19, 1123-1131.

10. Pratt, M. A. C., Bishop, T. E., White, D., Yasvinski, G., Ménard, M. M., Niu, M. Y. & Clarke, R. 2003. Estrogen Withdrawal-Induced NF-κB Activity and Bcl-3 Expression in Breast Cancer Cells: Roles in Growth and Hormone Independence. *Mol. Cell. Biol.*, 23, 6887-6900.

11. Wakefield A, Soukupova J, Montagne A, Ranger J, French R, Muller W and Clarkson R (2012) Bcl3 selectively promotes metastasis of ERBB2-driven mammary tumours Cancer Research (epub) 10.1158/0008-5472.CAN-12-1321.

The invention claimed is:
1. A method for the treatment of cancer, the method comprising administering to a patient in need of such treatment an effective amount of a compound of general formula (Ia):

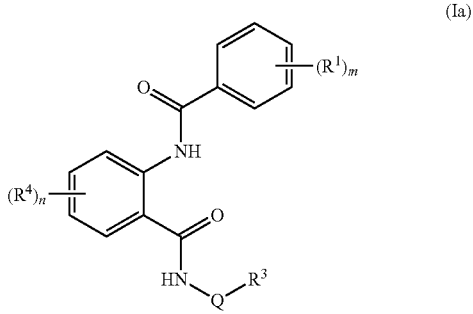

or a salt thereof, wherein:
each $R^1$ is independently halo, nitro, cyano, $C_{1-6}$ alkyl, $C_{2-6}$ alkenyl, $C_{1-6}$ haloalkyl, $OR^5$ or $N(R^5R^6)$, wherein at least one $R^1$ is fluoro;
each of $R^5$ and $R^6$ is independently hydrogen, $C_{1-6}$ alkyl or $C_{1-6}$ haloalkyl;
m is 0, 1 or 2;
Q is $(CH_2)_p$;
p is 1, 2, 3 or 4;
$R^3$ is morpholinyl, piperidinyl, piperazinyl, pyrrolidinyl, pyrazolidinyl, imidazolinyl, pyridyl, pyrrolyl, pyrimidinyl, imidazolyl or triazolyl;
each $R^4$ is independently nitro, cyano, $C_{1-6}$ alkyl, $C_{2-6}$ alkenyl, $C_{1-6}$ haloalkyl, $OR^9$ or $N(R^9R^{10})$;
each of $R^9$ and $R^{10}$ is independently hydrogen, $C_{1-6}$ alkyl or $C_{1-6}$ haloalkyl; and
n is 0, 1 or 2.

2. A method according to claim 1, wherein $R^1$ is halo, nitro, $C_{1-4}$ alkyl, $C_{1-4}$ haloalkyl or $OR^5$.

3. A method according to claim 1, wherein $R^5$ is hydrogen, or methyl or ethyl, either of which may optionally be substituted by one or more halo substituents.

4. A method according to claim 1, wherein $R^1$ is halo, nitro, methyl, trifluoromethyl, OH, methoxy or trifluoromethoxy.

5. A method according to claim 1, wherein m is 1 or 2.

6. A method according to claim 1, wherein $R^1$ is 2-fluoro.

7. A method according to claim 1, wherein at least one $R^1$ is $OR^5$.

8. A method according to claim 7, wherein $R^5$ is $C_{1-6}$ alkyl.

9. A method according to claim 8, wherein $R^5$ is methyl.

10. A method according to claim 1, wherein $R^3$ is morpholinyl.

11. A method according to claim 1, wherein p is 2 or 3.

12. A method according to claim 1, wherein $R^4$ is $C_{1-4}$ alkyl or $OR^9$.

13. A method according to claim 12, wherein $R^4$ is methyl or methoxy.

14. A method according to claim 1, wherein n is 0 or 1.

15. A method according to claim 1, comprising administering to a patient an effective amount of a compound selected from:
2-[(3-fluorobenzoyl)amino]-N-(2-morpholin-4-ylethyl) benzamide;
2-[(4-fluorobenzoyl)amino]-N-(2-morpholin-4-ylethyl) benzamide;
2-[(2-methoxybenzoyl)amino]-N-(2-morpholin-4-yl-ethyl)benzamide;
2-[(3-methoxybenzoyl)amino]-N-(2-morpholin-4-yl-ethyl)benzamide;
2-[(4-methoxybenzoyl)amino]-N-(2-morpholin-4-yl-ethyl)benzamide;
2-[(2-nitrobenzoyl)amino]-N-(2-morpholin-4-ylethyl) benzamide;
2-[(3-nitrobenzoyl)amino]-N-(2-morpholin-4-ylethyl) benzamide;
2-[(4-nitrobenzoyl)amino]-N-(2-morpholin-4-ylethyl) benzamide;
2-[(2-methylbenzoyl)amino]-N-(2-morpholin-4-ylethyl) benzamide;
2-benzamido-N-(2-morpholin-4-ylethyl)benzamide;
3,4-dimethoxy-N-(2-[(2-morpholin-4-ylethyl)carbamoyl] phenyl)benzamide;
3,5-dimethoxy-N-(2-[(2-morpholin-4-ylethyl)carbamoyl] phenyl) benzamide;
3,5-difluoro-N-(2-[(2-morpholin-4-ylethyl)carbamoyl] phenyl)benzamide;
2,6-difluoro-N-(2-[(2-morpholin-4-ylethyl) carbamoyl] phenyl)benzamide;
2,4-difluoro-N-(2-[(2-morpholin-4-ylethyl)carbamoyl] phenyl)benzamide;
2-[(2-fluorobenzoyl)amino]-N-(2-morpholin-4-ylpropyl) benzamide;
2-[(4-fluorobenzoyl)amino]-N-(pyridin-3-ylmethyl)benzamide;
2-[(4-fluorobenzoyl)amino]-N-(pyrrolidin-3-ylmethyl) benzamide;
2-[(4-fluorobenzoyl)amino]-N-(piperidin-3-ylmethyl) benzamide;
2-[(4-fluorobenzoyl)amino]-N-(piperazin-3-ylmethyl) benzamide;
N-(2-aminoethyl)-2-(2-fluorobenzamido) benzamide;
2-[(2-fluorobenzoyl)amino]-3-methyl-N-(2-morpholin-4-ylethyl)benzamide;
2-[(2-fluorobenzoyl)amino]-3-methoxy-N-(2-morpholin-4-ylethyl)benzamide;
2-fluoro-N-(2-((2-morpholinoethyl)carbamoyl)phenyl) benzamide; and
2-[(2-fluorobenzoyl) amino]-N-(2-morpholin-4-ylethyl) benzamide; or pharmaceutically or veterinarily acceptable salts thereof.

16. The method of claim 1, wherein the cancer is leukaemia or lymphoma.

17. The method of claim 1, wherein the cancer is anaplastic large cell lymphoma (ALCLs), classic Hodgkin lymphoma (cHL), non-Hodgkin's lymphoma or solid tumour cancer.

18. The method of claim 17, wherein the cancer is a solid tumour cancer selected from the group consisting of: breast cancer, melanoma, lung cancer, pancreatic cancer, oesophageal cancer, colorectal cancer, nasopharyngeal carcinoma and hepatocarcinoma.

19. The method according to claim 1, wherein the treatment comprises the treatment or prevention of metastasis in cancers.

20. The method according to claim 18, wherein the cancer is breast cancer.

21. The method according to claim 20, wherein the breast cancer is triple negative breast cancer or HER2 enriched breast cancer.

22. The method according to claim 1, wherein a compound of general formula (Ia) is administered in combination with one or more additional active agents which are useful in the treatment of cancer.

23. The method according to claim 22, wherein the one or more additional active agent is selected from: the anti-HER2 agents such as trastuzumab and pertuzurnab; the standard adjuvant therapy regimens 5-fluorouracil, doxorubicin, and cyclophosphamide (FAC); 5-fluorouracil, epirubicin, and cyclophosphamide (FEC); and doxorubicin and cyclophosphamide (AC); cyclophosphamide, methotrexate, and 5-fluorouracil (CMF); and docetaxel, doxorubicin, cyclophosphamide (TAC); and the anti-angiogenic/antimetastatic agent bevacizumab (Avastin).

* * * * *